(12) United States Patent
Berkowitz et al.

(10) Patent No.: US 7,767,388 B2
(45) Date of Patent: Aug. 3, 2010

(54) METHOD FOR MONITORING THE STEREOSELECTIVITY AND RELATIVE RATE OF ORGANIC CHEMICAL REACTIONS

(75) Inventors: David B. Berkowitz, Lincoln, NE (US); Sangeeta Dey, Lincoln, NE (US); Kannan R. Karukurichi, Lincoln, NE (US); Weijun Shen, Lincoln, NE (US)

(73) Assignee: NUtech Ventures, Lincoln, NE (US)

( * ) Notice: Subject to any disclaimer, the term of this patent is extended or adjusted under 35 U.S.C. 154(b) by 1056 days.

(21) Appl. No.: 11/434,247

(22) Filed: May 16, 2006

(65) Prior Publication Data

US 2006/0263895 A1    Nov. 23, 2006

Related U.S. Application Data

(60) Provisional application No. 60/681,157, filed on May 16, 2005.

(51) Int. Cl.
    *C12Q 1/00*    (2006.01)
(52) U.S. Cl. .......................................... 435/4; 436/164
(58) Field of Classification Search ...................... 435/4; 436/164
    See application file for complete search history.

(56) References Cited

U.S. PATENT DOCUMENTS 6,974,665 B2 *  12/2005  Berkowitz et al. ............. 435/4
2007/0099946 A1 *  5/2007  Doshan et al. ............. 514/282

FOREIGN PATENT DOCUMENTS

WO    WO 00/78997    * 12/2000

OTHER PUBLICATIONS

Schaus S. et al. Highly Selective Hydrolytic Kinetic Resolution of Terminal Epoxides . . . JACS 124(7)1307-1315, 2002.*
Schaus, S. E.; Brandes, B. D.; Larrow, J. F.; Tokunaga, M.; Hansen, K. B.; Gould, A. E.; Furrow, M. E.; Jacobsen, E. N. *J. Am. Chem. Soc.* 2002. 124, 1307-1315.

* cited by examiner

*Primary Examiner*—Ralph Gitomer
(74) *Attorney, Agent, or Firm*—Fish & Richardson P.C.

(57) ABSTRACT

A method for monitoring the stereoselectivity of at least one organic chemical reaction and the relative rate of at least one organic chemical reaction, wherein the reaction produces a product that can exist as at least two stereoisomers, is provided herein. Also disclosed are methods for identifying and preparing catalysts for the above reactions.

29 Claims, 10 Drawing Sheets

A. HLADH

B. TBADH

US 7,767,388 B2

METHOD FOR MONITORING THE STEREOSELECTIVITY AND RELATIVE RATE OF ORGANIC CHEMICAL REACTIONS

This application claims benefit to provisional application 60/681,157 filed May 16, 2005.

This invention was made with government support under CHE0317083 awarded by the National Science Foundation. The government has certain rights in the invention.

FIELD OF THE INVENTION

This invention relates to a method for the in situ monitoring of stereoselectivities and relative rates of reaction.

BACKGROUND OF THE INVENTION

Combinatorial methods have made an important impact on catalyst discovery in recent years. Notable examples include the discovery of catalysts for asymmetric acylation and Stetter-type chemistry, Pd(0) and Cu(I)-mediated allylic alkylations, Ag-based carbene insertion, $FeCl_2$-mediated epoxidation, and early transition metal-based additions to imines. These successes have spurred interest in catalyst screening. Thus, screens for active lead catalysts, based upon IR thermography fluorescence and dye formation/bleaching have been reported. However, some methods for estimating relative rates, for example, involve the alteration of the substrate by the installation of a chromophore. In some cases, the substrate is so significantly altered, that a positive result in the screen, does not translate into a positive result with the original, unperturbed substrate.

Particularly valuable screens also provide information on enantioselectivity. Such screening methods include chiral GC and HPLC, CD and ORD and methods based upon installing MS or fluorescence tags or condensations with indicators.

The most common methods for estimating enantioselectivity are time-consuming and serial in nature. They involve chiral chromatography (usually HPLC or GC), and can be automated by the use of auto-injectors, but have the disadvantages of (i) requiring reaction quenching and work-up and of (ii) offering little possibility for parallel screening. Other approaches to estimating enantiomeric excess require that the product be derivatized, in a separate kinetic resolution step, following work-up of the reaction.

A reported in sits screen that provides information on both relative rate and product ee employs an isotopically chiral $^{13}C$ NMR probe substrate. This allows obtaining information on both relative rate and enantioselectivity of the catalyst being screened, on the fly, without the need to draw aliquots. The disadvantage of that method is that it requires the stereoselective synthesis of an expensive 13-C-enriched model substrate. Furthermore, this approach placed the isotopically chiral, geminal dimethyl 'reporting group' directly adjacent to the carbonyl reaction center, thereby creating steric hindrance. This limits the suitability of the model substrate to mimic more common substrates for carbonyl addition reactions that possess sterically less hindered carbonyl groups.

As described in U.S. Pat. No. 6,974,665, the entire disclosure of which is incorporated herein by reference, enzymes can be used to assist organic chemists, using an approach termed "in situ enzymatic screening" (ISES). Enzymes are used to monitor relative rates in real time for allylic substitution catalysts run in parallel. ISES (In Situ Enzymatic Screening) is run in a bilayer, in this case, with a lower, aqueous enzymatic layer (containing ethanol dehydrogenase and aldehyde dehydrogenase) reporting (via NADH production) on the turnover of an allylic ethyl carbonate substrate in an upper organic reaction layer. The first examples of asymmetric, Ni(0)-mediated allylic amination reactions were uncovered in the process.

BRIEF SUMMARY OF THE INVENTION

One embodiment of the present invention provides a method for monitoring the stereoselectivity of at least one organic chemical reaction and the relative rate of at least one organic chemical reaction, wherein the reaction produces a product that can exist as at least two stereoisomers, the process comprising:

providing a first reaction zone containing (1) an organic phase comprising the reaction mixture for producing the product and (2) an aqueous phase adjacent to but substantially immiscible with the organic phase, the aqueous phase containing at least one first sensing agent that preferentially acts on a first stereoisomer in the product to produce a monitorable change, the product being diffusible into the aqueous layer (2).

providing a second reaction zone containing (A) an organic phase also comprising the reaction mixture for producing the product and (B) an aqueous phase adjacent to, but substantially immiscible with the organic phase, the aqueous phase containing at least one sensing agent that is different from the first sensing agent and that

[i] also preferentially acts on the first stereoisomer in the product, but with a different stereoselectivity for the stereoisomers formed in the product than the first sensing agent to produce a monitorable change,

[ii] acts at equal rates on both formed stereoisomers of the product to produce a monitorable change or,

[iii] preferentially acts on a second stereoisomer in the product to produce a monitorable change, the product being diffusible into the aqueous layer (B), conducting the reactions in the organic phases (1) and (A) to produce the products, allowing the products to diffuse into the aqueous phases (2) and (B) and react with the first and second sensing agents, monitoring the changes caused by the reactions with the first and second sensing agents and determining from the changes, the relative rate and stereoselectivity of the organic chemical reaction in the organic phases (1) and (2).

Another embodiment of the invention relates to a kit adapted for efficiently carrying out the method of the invention.

A further embodiment of the invention concerns a novel method for identifying a catalyst for an organic chemical reaction that efficiently forms a product that can exist as at least two stereoisomers and that is also stereoselective for at least one of the stereoisomers comprising:

providing a first reaction zone containing (1) an organic phase comprising the reaction mixture for producing the product, the mixture containing a candidate catalyst for the reaction and (2) an aqueous phase adjacent to, but substantially immiscible with the organic phase, the aqueous phase containing at least one first sensing agent that preferentially-acts on a first stereoisomer in the product to produce a monitorable change, the product being diffusible into the aqueous layer (2).

providing a second reaction zone containing (A) an organic phase also comprising the reaction mixture for producing the product and (B) an aqueous phase adjacent to, but substantially immiscible with the organic phase, the aqueous phase containing at least one sensing agent that is different from the first sensing agent and that

[i] also preferentially acts on the first stereoisomer in the product, but with a different stereoselectivity for the stereoisomers formed in the product than the first sensing agent to produce a monitorable change or

[ii] acts at equal rates on both formed stereoisomers of the product to produce a monitorable change or

[iii] preferentially acts on a second stereoisomer in the product to produce a monitorable change, conducting the reactions in the organic phases (1) and (A) to produce the products, allowing the products to diffuse into the aqueous phases (2) and (B) and react with the first and second sensing agents, monitoring the changes caused by the reactions with the first and second sensing agents and determining from the changes the relative rate of reaction and stereoselectivity of the catalyst.

An additional embodiment of the invention relates to a method for preparing a catalyst for an organic chemical reaction that produces a product that can exist as at least two stereoisomers and that is also stereoselective for at least one of the stereoisomers comprising preparing a candidate catalyst for said reaction and:

providing a first reaction zone containing (1) an organic phase comprising the reaction mixture for producing said product, said mixture containing a candidate catalyst for said reaction and (2) an aqueous phase adjacent to, but substantially immiscible with said organic phase, said aqueous phase containing at least one first sensing agent that preferentially acts on a first stereoisomer in said product to produce a monitorable change, said product being diffusible into said aqueous layer (2).

providing a second reaction zone containing (A) an organic phase also comprising the reaction mixture for producing said product and (B) an aqueous phase adjacent to, but substantially immiscible with said organic phase, said aqueous phase containing at least one sensing agent that is different from said first sensing agent and that

[i] also preferentially acts on the first stereoisomer in the product, but with a different stereoselectivity for the stereoisomers formed in the product than the first sensing agent to produce a monitorable change or

[ii] acts at equal rates on both formed stereoisomers of the product to produce a monitorable change or

[iii] preferentially acts on a second stereoisomer in the product to produce a monitorable change, said product being diffusible into said aqueous layer (B), conducting said reactions in said organic phases (1) and (A) to produce said products, allowing said products to diffuse into said aqueous phases (2) and (B) and react with said first and second sensing agents, monitoring the changes caused by said reactions with said first and second sensing agents and determining from said changes the relative rate and stereoselectivity of said catalyst.

DETAILED DESCRIPTION OF THE INVENTION

Figure 1:
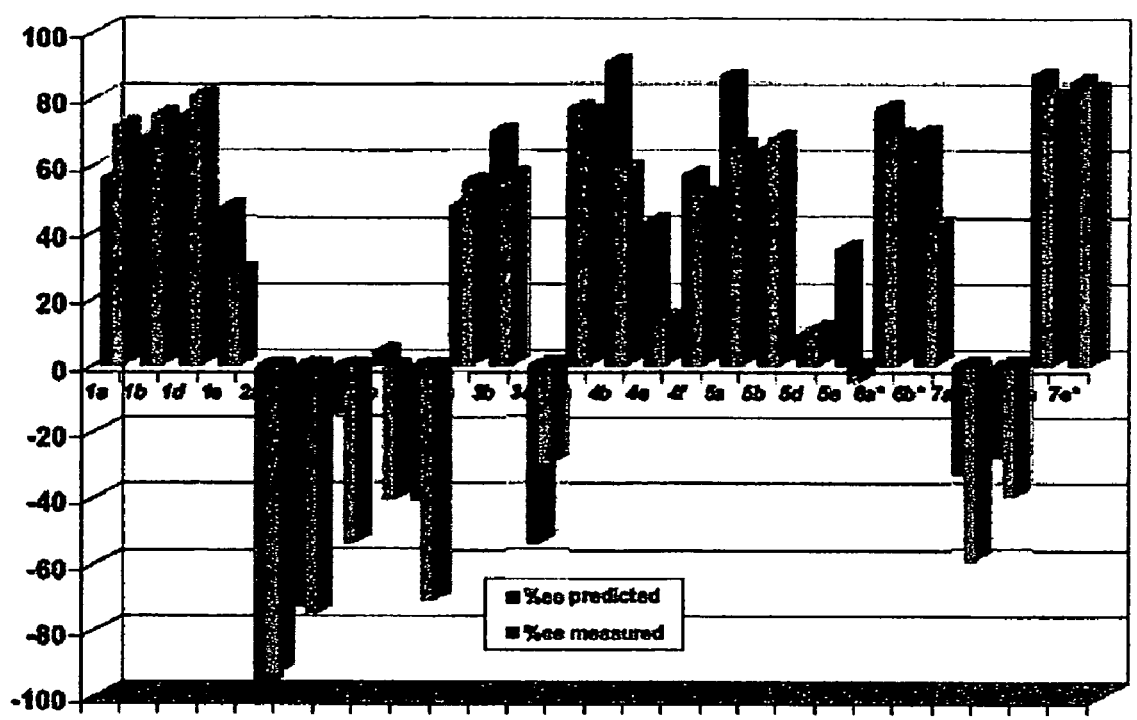
FIG. 1 shows a comparison of predicted and observed ee's for the HKR of ±propylene oxide.

The present invention is predicated on the discovery that information on both the relative rates and stereoselectivities for an array of reactions can be provided in situ by conducting the reactions in parallel and observing the effects of the products produced thereby when acted upon by different reporting agents, typically enzymes. The method of the invention differs significantly from that disclosed in U.S. Pat. No. 6,974, 665. Specifically, (i) the reporting enzymes are used to observe the reaction product directly (for example a chiral 1,2-diol), rather than a byproduct of catalyst turnover (for example EtOH). This allows use of the chirality in the reporting enzyme (chiral sensor). In addition (ii), two reporting enzymes are employed, in parallel vessels, to obtain information on stereoselectivity, as well as relative rates.

The invention permits, e.g., the screening of an array of potential catalysts for reactions of interest, in parallel, and in situ. For example, two enzymes with differing stereoselectivity for the reaction product are employed. Each enzyme provides, e.g., a spectroscopic signal (e.g. NADH or NADPH formation) that can be detected by either UV/visible absorption spectroscopy or fluorescence spectroscopy. This spectroscopic signal can be followed in real time, while the reaction is taking place.

The method of the invention utilizes techniques similar to those disclosed in U.S. Pat. No. 6,974,665. The method of the invention is utilized to distinguish the situation in which catalyst A has the same rate as catalyst B, but greater R:S selectivity, from the situation in which catalysts A and B display similar stereoselectivities, but catalyst A possesses a greater rate.

The method does not require alteration of either the reactant or the product, by installation of a chromophore or mass tag, for example. It has the further advantage of providing information in real time, without the need to draw aliquots, quench the reaction or perform a work-up.

The invention requires that the reaction to be screened yield a product that reacts with the reporting (sensing) agent, e.g., an enzyme. Potential "reporting enzymes" are screened for both their substrate specificity and stereoselectivity. All that is required is that one have two different reporting enzymes that show different stereopreferences in their reactions with the stereoisomeric organic reaction product of interest. Reporting enzymes can be used for a variety of reactions.

The method of the invention allows reliable predictions that can lead to the discovery of a number of interesting asymmetric catalysts. For example, the method has been used to screen an array of new chiral Co(III)-salen catalysts for their ability to catalyze the hydrolytic kinetic resolution (HKR) of racemic, propylene oxide and hexene oxide.

The method may be utilized in the form of a screening kit. The kit could contain, for example, separately packaged reaction vessels (e.g., cuvettes or microtitre plates), the organic and aqueous liquid compositions, catalysts, buffers, and enzymes. These compositions could be packaged with or without organic and aqueous solvents. The kit could be provided with or without catalysts. In other words, for a screening kit without catalysts, the practitioner would supply his/her own catalyst candidates or catalyst candidate library to be screened. The kit could be provided with our without a test substrate. In the latter case, the practitioner would provide his/her own test substrate for the reaction of interest.

Typically, in accordance with the method of the invention, two reaction vessels or two reaction wells containing an organic layer and an aqueous layer are placed in parallel. Each vessel contains the same organic layer and different aqueous reporting layers.

To demonstrate proof of principle for the method of the invention, the hydrolytic kinetic resolution (HKR) of (±)-propylene oxide to 1,2-propane diol was chosen, a reaction known to be catalyzed efficiently by chiral Co(III)-salen complexes. See Scheme 1. To provide an information-rich data set requires that the two reporting enzymes display different, ideally opposite stereoisomeric preferences. Preliminary screening revealed that alcohol dehydrogenase from horse liver (HLADH) and from *Thermoaniaerobium brockii* (TBADH) fulfill this criterion. The former enzyme prefers (S)-1,2-propanediol, whereas the latter favors the (R)-antipode. A focused 7×7 "salen" array was designed (Table S3) so as to explore the interplay of novel chiral diamine scaffolds (from terpenoid, amino acid, and carbohydrate skeletons) with sterically and electronically diverse "salicylaldehydes", from which the Co(III)-salen catalysts were prepared.

Figure 2:
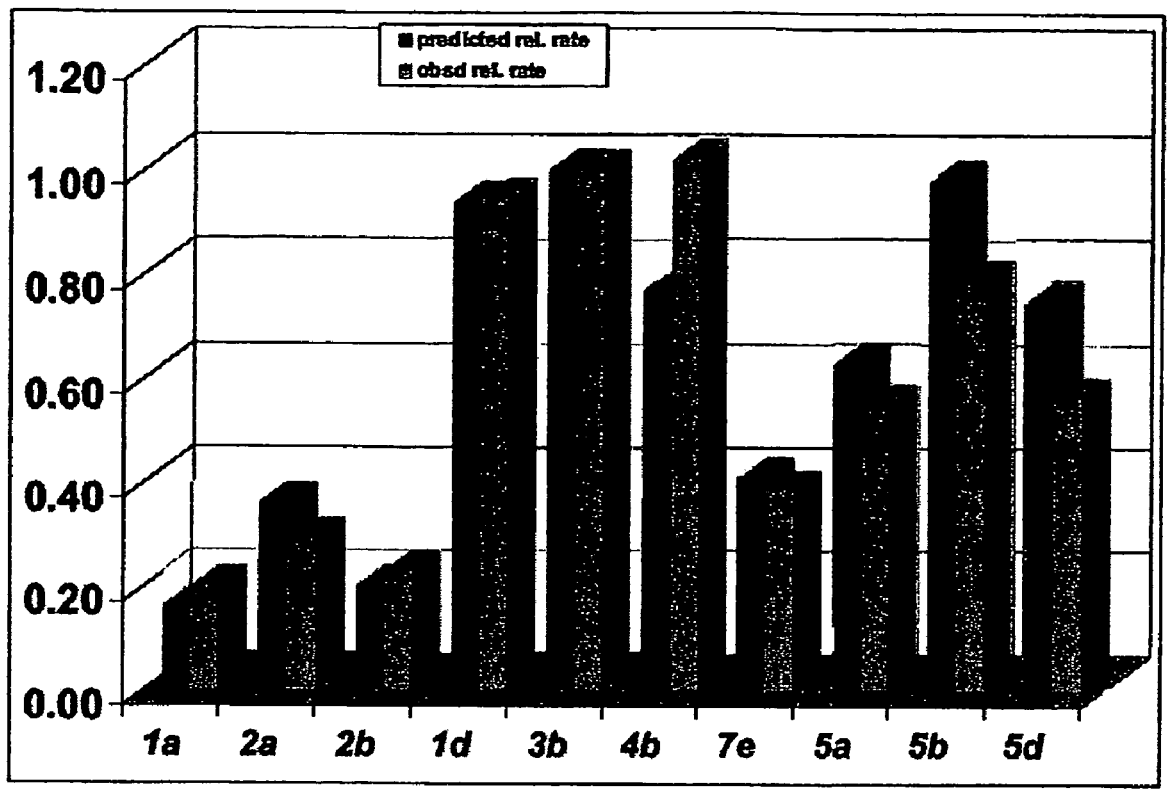
FIG. 2 shows a comparison of predicted and observed relative rates (normalized to 4b) for Co(III)-salen mediated HHR of ±propylene oxide.

In the experiment, each Co(III)-salen catalyst (at 0.25 mol %) is placed in a lower organic layer (CHCl$_3$) and expoxide, 300 μL total volume) in each of two parallel cuvettes. Aqueous reporting layers containing TBADH/NADP+ (cuvette 1) and HLADH/NAD+ (cuvette 2), respectively, are then added. The increase in absorbance at 340 nm can be followed for several such sets in parallel by UV-vis spectrophotometry. The kinetic data are then used to make the double-cuvette ISES predictions. A comparison of the predicted and measured ee's is presented in FIG. 1. Of 49 new salens targeted, 42 were obtained, and 25 gave active Co(III)-catalysts. Above a 65% ee threshold in either direction, ISES found 9 of 11 true hits (18% false negatives) and succeeded in 9 of its 12 predictions (25% false positives). Note that the measured ee's are for the HKR under the neat conditions typically used in the conventional Jacobsen method whereas the predicted ee's are for the bilayer used in double-cuvette ISES. FIG. 2 compares the relative rates of reaction predicted by ISES with those observed in a bilayer by $^1$H NMR. Observed relative rates agree with ISES predictions to within 25% in 9 of 10 cases measured, with the Co(III) salen catalyst 5d displaying slightly greater variance.

Interesting "combinatorial hits" include the finding that 2-hydroxy-1-naphthaldehyde (c) yields catalysts with very low activity, whereas 1-hydroxy-2-naphthaldehyde (d) is the best partner for beta-pinene-derived diamine 1. Furthermore, a remarkable inversion of stereoselectivity is observed for salens emanating from the new β-D-fructopyranose-based diamine 7, upon going from the 3,5-di-tert-butylsalicylaldehyde partner (a) to the sterically less encumbered 3,5-diiodo congener (e).

The following will be understood by those skilled in the art.

Although the invention is illustrated with reference to the hydrolysis of epoxides, the method of the invention is applicable for any organic chemical reaction that results in the

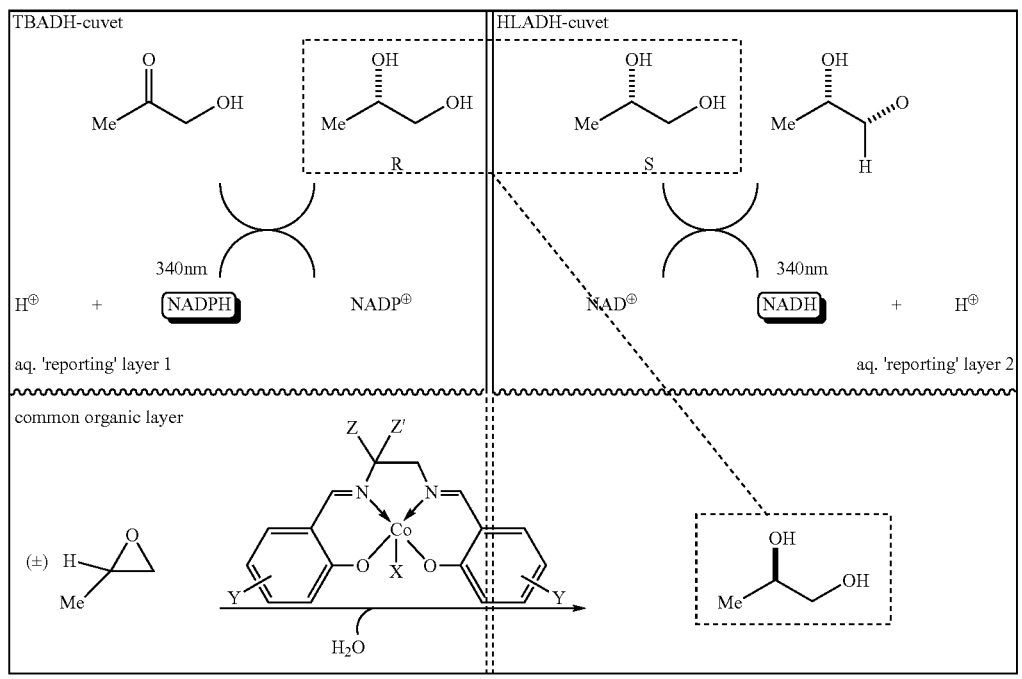

Scheme 1. Double-Cuvet ISES production of stereoisomers and particularly for such reactions that employ catalysts. In those methods wherein an alcohol is produced, the alcohol product may comprise a diol such as the 1,2-propane- and 1,2-hexane-diols exemplified below or a halohydrin, a β-azido alcohol, a β-cyanoalcohol, a β-alkoxy alcohol, a β-aryloxy alcohol, a β-thioalkyl alcohol, β-amino alcohol, the product of an aldol-type condensation, wherein a carbon acid having a proton alpha to one or more electron-withdrawing groups (e.g., nitro group, carbonyl group (aldehyde, ketone, ester, amide), cyano group, sulfonyl group, sulfinyl group, sulfoxide, phosphonate ester, isonitrile group, imine functionality) is condensed with an aldehyde and is deprotonated in the course of the condensation, the product of a Morita-Baylis-Hillman reaction, the product of a carbonyl reduction reaction or a cyanohydrin. The product may also comprise an amine wherein the sensing agents are amine dehydrogenase or amine oxidase enzymes that oxidize the product. Where the product is an aldehyde or hemiacetal the sensing agents in aqueous phases (2) and (B) may be aldehyde or alcohol dehydrogenase enzymes that oxidize said product.

Moreover, any suitable reaction medium, i.e., solvent and reaction adjuvants as well as aqueous medium may also be employed in the practice of the invention. Although the invention is illustrated employing enzymes as sensing agents, any suitable such agent that preferentially reacts with a specific stereoisomer in the reaction product to produce a monitorable change in the aqueous medium may be utilized. Suitable enzymes include alcohol, amine or aldehyde oxidases or dehydrogenases, it being understood that one may couple the oxidase reaction with the (Horseradish) Peroxidase (HRP) reaction, wherein the hydrogen peroxide byproduct from the oxidase reaction leads to the oxidation of a dye co-substrate for the peroxidase enzyme, producing an observable signal. The monitorable change in the aqueous medium may also comprise any effect that is measurable by suitable and appropriate monitoring techniques. In addition, the method of the invention is applicable for the evaluation of suitable known candidate catalysts as well as for the preparation of novel catalysts for reactions that produce mixtures of stereoisomers. By the term, "relative rate" of organic chemical reaction is meant the relative rate of the reaction with reference to a "standard" reaction, i.e., another reaction under investigation or a reaction known in the art.

All reactions were conducted under argon atmosphere using flame or oven-dried glassware, unless otherwise indicated. Methylene chloride was distilled from $CaH_2$. Toluene, THF, and $Et_2O$ were distilled from sodium benzophenone ketyl. Methanol was distilled from Mg, and ethanol from nadiethyl phthalate. Alcohol dehydrogenase from equine liver (HLADH, EC 1.1.1.1), alcohol dehydrogenase from *Thermoanaerobium brockii* (TBADH, EC 1.1.1.2), β-NAD+ (sodium salt), β-NADP+ (sodium salt), 3,5-Di-tert-butylsalicylaldehyde (a), 3-tert-butylsalicylaldehyde (b), 2-hydroxy-1-naphthaldehyde (c), cobalt(II)-acetate tetrahydrate, 1-hydroxy-2-naphthaldehyde (d), 3,5-diiodosalicylaldehyde (e), 4-benzyloxysalicylaldehyde (f) and 8-hydroxy-1,1,7,7-tetramethyljulolidinyl-9-carboxaldehyde (g) were purchased.

Flash chromatography was performed using Merck silica gel 60 (230-400 mesh). 1H NMR spectra were recorded on Bruker-DRX-Avance-400 MHz, 500 MHz and 600 MHz instruments with chemical shifts reported relative to residual $CHC_{13}$ (7.25 ppm) and $CH_2Cl_2$ (5.2 ppm). Proton-decoupled $^{13}C$ NMR spectra were acquired on Bruker-DRX-Avance-400 MHz, 500 MHz and 600 MHz instruments with chemical shifts reported relative to $CHCl_3$ (77.0 ppm). Optical rotation @589 nm was measured at 19° C. in an Autopol polarimeter.

IR spectra were obtained using a Nicolet Avatar 360 FTIR spectrometer. Mass spectra were acquired at the Nebraska Center for Mass Spectrometry (University of Nebraska-Lincoln). Enzyme assays and ISES were done in a Shimadzu UV-2101PC spectrophotometer equipped with a CPS-260 six cell positioner and thermoelectric temperature control (set at 25° C. for all experiments reported), or a Shimadzu 2401 spectrophotometer, equipped with a 12-cell changer and water-jacketed cell holder for temperature control. Enantiomeric excesses were determined using a Chiralcel OD (0.46 mm×25 cm) chiral column.

General Procedure A: Synthesis of Chiral 'Salen' Ligands (illustrated for 2a). [See Table S3 below.]

An oven-dried RB flask was charged with (1S)-phenyl-1,2-ethylenediamine (250 mg, 1.83 mmol) and 3,5-di-tert-butylsalicylaldehyde (861 mg, 3.67 mmol) and freshly distilled ethanol (2 mL). The reaction mixture was stirred at 45° C. for 1 d whereupon, in most cases, the salen product crystallized out. The reaction temperature and time varied, as indicated in the individual procedures. In the case of 2a, the product could be obtained in pure form (823 mg, 79%) by simple trituration with cold ethanol. If further purification was required, recrystallization or column chromatography was used.

N,N'-Bis(3',5'-di-tert-butylsalicylidene[1R-(1α,2α,5α)]-2-amino-7,7-dimethyl-2-bicyclo[3.3.1]heptaneethanamine (1a)

Diamine 1 was prepared from commercially available (1S)-(−)-β-pinene as described. General Procedure A was followed. Diamine 1 (43.3 mg, 0.32 mmol) and 3,5-di-tert-butylsalicylaldehyde (150 mg, 0.64 mmol) were heated at 40-50° C. for 5 h, filtered and triturated (cold EtOH), to produce clean 1a (140 mg, 92%): [α]19 D+14.2 (c 3.54, $CH_2Cl_2$); 1H NMR (400 MHz, $CDCl_3$) δ 1.23 (d, J=10 Hz, 1H), 1.23 (s, 3H), 1.26 (s, 9H), 1.26 (s, 9H), 1.36 (s, 3H), 1.43 (s, 9H), 1.43 (s, 9H), 1.92-1.97 (m, 3H), 2.03 (app t, J=11, 10 Hz, 1H), 2.17-2.26 (m, 2H), 2.28-2.32 (m, 1H), 2.42 (t, J=5.5 Hz, 1H), 3.70 (d, J=8 Hz, 1H), 3.91 (d, J=8 Hz, 1H), 6.98 (d, J=2 Hz, 1H), 7.04 (d, J=2 Hz, 1H), 7.32 (d, J=2 Hz, 1H), 7.33 (d, J=2 Hz, 1H), 8.25 (s, 1H), 8.264 (s, 1H), 13.62 (br s, 1H), 14.36 (br s, 1H); 13C NMR (100 MHz, $CDCl_3$) δ 23.9, 25.6, 25.8, 28.2, 28.6, 29.5, 31.47, 31.49, 34.1, 35.0, 35.1, 38.5, 40.0, 48.6, 67.2, 68.8, 117.8, 117.8, 126.0, 126.4, 126.6, 126.9, 136.5, 136.5, 139.6, 139.9, 158.1, 158.6, 162.69, 167.71; HRMS (FAB, 3-NOBA) calcd for $C_{40}H_{61}N_2O_2$ (M+H)+ 601.4733, obsd. 601.4710.

N,N'-Bis(3'-tert-butylsalicylidene)-[1R-(1α,2α,5α)]-2-amino-7,7-dimethyl-2-bicyclo[3.3.1]heptaneethanamine (1b)

General Procedure A was followed. Diamine 1 (101 mg, 0.60 mmol) and 3-tertbutyl-2-hydroxybenzaldehyde (214 mg, 1.20 mmol), and chromatographic purification (5% $Et_3N$ hexenes), produced compound 1b (180 mg, 61%): [α]19 D +2.66 (c 4.65, $CH_2Cl_2$); 1H NMR (400 MHz, $CDCl_3$) δ 1.05 (d, J=10.8 Hz, 1H), 1.23 (s, 21H), 1.35 (s, 3H) 1.89-2.06 (m, 3H), 2.13-2.31 (m, 3H), 2.41 (app t, J=5.6, 5 Hz, 1H), 3.76 (d, J=12 Hz, 1H), 3.86 (d, J=12 Hz, 1H), 6.84 (t, J=8 Hz, 2H), 7.10 (dd, J=9.0, 2 Hz, 2H), 7.29 (dt, J=9.2 Hz, 2H), 8.13 (s, 1H), 8.17 (s, 1H), 13.12 (s, 1H), 13.63 (s, 1H); 13C NMR (100 MHz, $CD_2C_{12}$) δ 23.8, 25.7, 28.2, 28.5, 31.39, 31.41, 33.9, 38.4, 40.0, 46.3, 48.3, 47.6, 68.9, 116.4, 166.5, 117.8, 117.9, 127.9, 129.4, 129.7, 140.9, 141.2, 158.7, 159.2, 161.8, 167.1; HRMS (FAB, 3-NOBA) calcd for $C_{32}H_{45}O_2N_2$ (M+H)+ 489.3481, obsd 489.3492.

N,N'-Bis(2'-hydroxy-1'-naphthylidene)-[1R-(1α,2α,5α)]-2-amino-7,7-dimethyl-2-bicyclo[3.3.1]heptane-ethanamine (1c)

General Procedure A was followed. Diamine 1 (98 mg, 0.58 mmol) and 2-hydroxy-1-naphthaldehyde (201 mg, 1.16 mmol) were heated at 75° C. for 5 h. Filtration, followed by recrystallization from absolute ethanol provided 1c (230 mg, 84%): [α]19D −58.4 (c 2.92, $CH_2Cl_2$); 1H NMR (400 MHz, $CDCl_3$) δ 1.21 (d, J=10.3 Hz, 1H), 1.24 (s, 3H), 1.43 (s, 3H), 2.07 (app d, J=6.5 Hz, 3H), 2.20-2.33 (m, 2H), 2.39-2.44 (m, 1H), 2.61 (app t, J=5 Hz, 1H), 3.83 (d, J=13 Hz, 1H), 3.92 (d, J=13.0 Hz, 1H), 6.74 (d, J=9 Hz, 1H), 6.85 (d, J=9 Hz, 1H), 7.04 (app t, J=7.5 Hz, 1H), 7.11 (app t, J=7.4 Hz, 1H), 7.17 (app t, J=7.5 Hz, 1H), 7.21 (dt, J=8.1 Hz, 1H), 7.36 (d, J=8 Hz, 1H), 7.44 (d, J=7 Hz, 1H), 7.45 (d, J=9 Hz, 1H), 7.53 (d, J=9 Hz, 2H), 7.58 (d, J=8 Hz, 1H), 8.46 (s, 1H), 8.61 (s, 1H), 14.69 (br s, 2H); 13C NMR (100 MHz, $CDCl_3$) δ 23.7, 25.2, 27.3, 28.1, 28.7, 38.4, 40.2, 47.0, 64.5, 65.5, 106.3, 107.4, 117.7, 118.2, 122.5, 122.9, 122.94, 124.8, 126.0, 126.5, 127.8, 127.9, 128.8, 133.0, 133.7, 136.9, 147.6, 154.9, 161.2, 172.9, 177.2; HRMS (FAB, 3-NOBA) calcd for $C_{32}H_{33}N_2O_2$ (M+H)+ 477.2542, obsd 477.2530.

N,N'-Bis(1'-hydroxy-2'-naphthylidene)-[1R-(1α,2α,5α)]-2-amino-7,7-dimethyl-2-bicyclo[3.3.1]heptane-ethanamine (1d)

General Procedure A was followed. Diamine 1 (87.5 mg, 0.52 mmol) and 1-hydroxy-2-naphthaldehyde (179 mg, 1.04 mmol) were heated at reflux overnight to give crude salen as an oil. $SiO_2$ column chromatography (0%→30% EtOAc-hexenes) afforded pure salen 1d (185 mg, 73%): [α]19 D −355 (c 0.81, $CH_2Cl_2$); 1H NMR (400 MHz, $CDCl_3$) δ 1.24 (d, J=10.3 Hz, 1H), 1.26 (s, 3H), 1.45 (s, 3H) 2.09 (app d, 3H), 2.21-2.33 (m, 2H), 2.44 (m, J=5, 4.7 Hz, 1H), 3.81 (d, J=13 Hz, 1H), 3.86 (d, J=13 Hz, 1H), 6.68 (d, J=9.8 Hz, 1H), 6.73 (d, J=9.8 Hz, 1H), 6.78 (d, J=9.8 Hz, 1H), 6.83 (d, J=9.8 Hz, 1H), 7.39-7.62 (m, 6H), 7.67 (d, J=10 Hz, 1H), 7.81 (s, 1H), 8.43 (s, 1H), 8.45 (s, 1H), 13.93 (s, 1H), 14.02 (d, J=10 Hz, 1H); 13C NMR (100 MHz, $CDCl_3$) δ 23.7, 25.1, 26.9, 28.0, 28.6, 38.3, 40.1, 46.9, 63.7, 65.0, 108.6, 109.8, 114.7, 116.1, 124.8, 125, 125.2, 127.26, 127.34, 127.4, 128.2, 129.8, 129.9, 130.3, 137, 137.6, 158.4, 164.3, 172.2, 177.1; HRMS (FAB, 3-NOBA) calcd for $C_{32}H_{33}O_2N_2$ (M+H)+ 477.2542, obsd 477.2531.

N,N'-Bis(3',5'-diiodosalicylidene)-[1R-(1α,2α,5α)]-2-amino-7,7-dimethyl-2-bicyclo[3.3.1]heptaneethanamine(1e)

The title salen was obtained, following General Procedure A. Diamine 1 (36.4 mg, 0.22 mmol) and 3,5-diiodosalicylaldehyde (164 mg, 0.44 mmol) were heated at 40-50° C. for 5 h. Recrystallization from ethanol at −20° C. afforded pure 1e (136 mg, 91%): [α]19 D −24.8 (c 3.05, $CH_2Cl_2$); 1H NMR (400 MHz, $CD_2Cl_2$) δ 0.98 (d, J=10 Hz, 1H), 1.20 (s, 3H), 1.36 (s, 3H), 1.91-2.42 (m, 7H), 3.84 (d, J=13 Hz, 1H), 3.92 (d, J=13 Hz, 1H), 7.44 (s, 1H), 7.48 (s, 1H), 7.92 (s, 1H), 8.02 (s, 3H), 14.32 (br s, 1H), 15.31 (br s, 1H); 13C NMR (100 MHz, $CD_2Cl_2$) δ 23.9, 25.8, 26.2, 28.3, 28.9, 38.9, 40.5, 48.2, 67.9, 67.8, 77.6, 79.6, 87.9, 90.2, 119.2, 120.2, 140.6, 141.1, 149.3, 149.4, 160.6, 161.4, 164.0, 165.8; HRMS (FAB, 3-NOBA) calcd for $C_{24}H_{25}N_2O_2I_4$ (M+H)+ 880.8095, obsd 880.8121.

N,N'-Bis(4'-benzyloxysalicylidene)-[1R-(1α,2α,5α)]-2-amino-7,7-dimethyl-2-bicyclo[3.3.1]heptane-ethanamine (1f)

The target salen was obtained following General Procedure A. Diamine 1 (167 mg, 0.54 mmol) and 4-benzyloxysalicylaldehyde (246 mg, 1.08 mmol) were heated at 40-50° C. for 5 h. Recrystallization from ethanol yielded pure salen 1f (105 mg; 100%): [α]19 D −16.1 (c 2.93, $CH_2Cl_2$); 1H NMR (400 MHz, $CDCl_3$) δ 1.08 (d, J=10.4 Hz, 1H), 1.19 (s, 3H), 1.35 (s, 3H), 1.91-2.04 (m, 3H), 2.08-2.22 (m, 2H), 2.28-2.31 (m, 1H), 2.39 (app t, J=5 Hz, 1H), 3.79 (d, J=14 Hz, 1H), 3.81 (d, J=12 Hz, 1H), 5.03 (s, 3H), 5.04 (s, 3H), 6.33 (dd, J=9.2 Hz, 1H), 6.40 (s, 1H), 6.34-6.42 (m, 2H), 6.48 (d, J=2 Hz, 1H), 6.98 (app t, J=9 Hz, 2H), 7.30-7.42 (m, 10H), 7.90 (s, 1H), 8.02 (s, 1H), 13.7 (br s, 1H), 14.61 (br s, 1H); 13C NMR (100 MHz, $CDCl_3$) δ 23.7, 25.4, 26.1, 28.0, 28.2, 28.4, 38.2, 39.9, 47.6, 66.3, 67.6, 69.8, 69.9, 102.0, 102.5, 106.7, 107, 111.7, 112.3, 127.5, 128, 128.1, 128.5, 128.6, 132.8, 133.3, 136.3, 136.4, 160.1, 162.7, 163.3, 164.9, 165.8, 168.6; HRMS (FAB, 3-NOBA) calcd for $C_{38}H_{41}O_4N_2$ (M+H)+589.3066, obsd 589.3047.

N,N'-Bis(8'-hydroxy-1',1',7',7'-tetramethyljulolidine-9'-methylidene)-[1R-(1α,2α,5α)]-2-amino-7,7-dimethyl-2-bicyclo[3.3.1]heptane-ethanamine (1g)

General Procedure A was followed. Diamine 1 (55 mg, 0.33 mmol) and 8-hydroxy-1,1,7,7-tetramethyljulolidine-9-carboxaldehyde (180 mg, 0.66 mmol) were stirred for 24 h to obtain crude salen. Column chromatography (2% $Et_3N$ hexenes) afforded pure 1 g (130 mg, 65%): [α]19 D+63.6 (c 3.55, $CH_2Cl_2$); 1H NMR (400 MHz, $CDCl_3$) δ 1.18 (s, 4H), 1.21 (s, 12H), 1.32 (s, 3H) 1.49 (s, 12H), 1.69-1.74 (m, 8H), 1.93-1.97 (m, 3H), 2.35 (app d, J=4 Hz, 1H), 3.09 (br s, 4H), 3.17 (app t, J=6 Hz, 4H), 3.58 (d, J=12 Hz, 1H), 3.75 (d, J=12 Hz, 1H), 6.76 (s, 1H), 6.77 (s, 1H), 7.93 (s, 1H), 7.97 (s, 1H), 13.91 (br s, 1H), 14.63 (br s, 1H); 13C NMR (100 MHz, $CDCl_3$) δ 23.9, 25.8, 26.1, 28.2, 28.6, 28.7, 31.2, 31.3, 31.7, 32.2, 32.3, 36.7, 36.8, 38.3, 40.2, 40.2, 40.3, 46.3, 47.0, 47.1, 47.4, 47.5, 48.6, 65.8, 68.2, 108.9, 108.93, 114.8, 114.9, 127.7, 128.1, 145.7, 145.9, 160.5, 161.0, 163.7, 166.0; HRMS (FAB, 3-NOBA) $C_{44}H_{63}O_2N_4$ (M+H)+ 679.4951, obsd 679.4974.

N,N'-Bis(3',5'-di-tert-butylsalicylidene)-(1S)-phenyl-1,2-ethylenediamine (2a)

(1S)-Phenyl-1,2-ethylenediamine 2,3 was prepared from L-(+)-α-phenylglycine (Janssen Chimica, 99%). General Procedure A was followed. (1S)-phenyl-1,2-ethylenediamine (250 mg, 1.83 mmol) and 3,5-di-tertbutylsalicylaldehyde (861 mg, 3.67 mmol) were stirred at 45° C. for 24 h to obtain 2a. Trituration with ethanol provided pure salen (823 mg, 79%): [α]19 D+80.0 (c 0.97, $CH_2Cl_2$); 1H NMR (400 MHz, $CDCl_3$) δ 1.27 (s, 9H), 1.28 (s, 9H), 1.44 (s, 9H), 1.46 (s, 9H), 3.97 (dd, J=12.3, 8.9 Hz, 1H), 4.15 (dd, J=12.3, 4.1 Hz, 1H), 4.71 (dd, J=8.9, 4.1 Hz, 1H), 7.04 (d, J=2.5 Hz, 1H), 7.05 (d, J=2.5 Hz, 1H), 7.32 (t, J=7.3 Hz, 1H), 7.36 (d, J=2.5 Hz, 1H), 7.37 (d, J=2.5 Hz, 1H), 7.39 (d, J=7.3 Hz, 1H), 7.41 (d, J=7.3 Hz, 1H), 7.48 (d, J=7.3 Hz, 2H), 8.35 (s, 1H), 8.44 (s, 1H), 13.59 (br s, 1H), 13.62 (br s, 1H); 13C NMR (100 MHz, $DCl_3$) δ 29.40, 29.44, 31.42, 31.44, 34.1, 35.0, 66.5, 73.9, 117.76, 117.83, 126.1, 126.4, 127.1, 127.2, 127.7, 128.8, 136.5, 136.6, 140.0, 140.1, 140.9, 157.9, 158.1, 167.1, 167.9; HRMS (FAB, 3-NOBA) calcd for $C_{38}H_{53}O_2N_2$ (M+H)+ 569.4108, obsd 569.4091.

N,N'-Bis(3'-tert-butylsalicylidene)-(1S)-phenyl-1,2-ethylenediamine (2b)

The title salen was obtained from (1S)-phenyl-1,2-ethylenediamine (219 mg, 1.61 mmol) and 3-tert-butylsalicylaldehyde (516 mg, 2.89 mmol) by following General Procedure A, and stirring at 45° C. for 72 h. Following filtration, trituration with ice-cold ethanol provided pure 2b (515 mg, 78%): [α]19 D +43.9 (c 1.03, CH$_2$Cl$_2$); 1H NMR (400 MHz, CDCl$_3$), δ 1.40 (s, 9H), 1.43 (s, 9H), 3.97 (dd, J=12.3, 8.6 Hz, 1H), 4.13 (dd, J=12.3, 4.5 Hz, 1H), 4.70 (dd, J=8.6, 4.5 Hz, 1H), 6.75 (dd, J=7.6, 2.9 Hz, 1H), 6.77 (dd, J=7.6, 2.9 Hz, 1H), 1H, 7.03 (dd, J=7.6, 1.5 Hz, 1H), 7.06 (dd, J=7.6, 1.5 Hz, 1H), 7.27-7.32 (m, 3H), 7.40 (t, J=7.5 Hz, 2H), 7.46 (d, J=7.3 Hz, 2H), 8.29 (s, 1H), 8.42 (s, 1H), 13.74 (br s, 1H), 13.76 (br s, 1H); 13C NMR (100 MHz, CDCl$_3$) δ 29.28, 29.34, 34.8, 66.3, 73.9, 117.8, 118.0, 118.5, 118.6, 127.1, 127.8, 128.8, 129.5, 129.7, 129.9, 130.2, 137.2, 137.3, 140.6, 160.2, 160.4, 166.6, 167.5; HRMS (FAB, 3-NOBA) calcd for C$_{30}$H$_{37}$O$_2$N$_2$ (M+H)+ 457.2856, obsd 457.2841.

N,N'-Bis(2'-hydroxy-1'-naphthylidene)-(1S)-phenyl-1,2-ethylenediamine (2c)

General Procedure A was followed to obtain the title compound from (1S)-phenyl-1,2-ethylenediamine (253 mg, 1.86 mmol) and 2-hydroxy-1-naphthaldehyde (576 mg, 3.35 mmol), after stirring at 45° C. for 10 h. Trituration with cold ethanol afforded the pure salen 2c (689 mg, 93%): [α]19 D +34.4 (c 1.02, CH$_2$Cl$_2$); 1H NMR (400 MHz, CDCl$_3$) δ 4.03 (dd, J=12.9, 8.3 Hz, 1H), 4.21 (dd, J=12.9, 4.5 Hz, 1H), 4.84 (dd, J=8.3, 4.5 Hz, 1H), 6.90 (d, J=9.2 Hz, 1H), 7.04 (d, J=9.1 Hz, 1H), 7.17-7.25 (m, 2H), 7.32-7.45 (m, 5H), 7.50-7.55 (m, 3H), 7.61 (d, J=8.9 Hz, 2H), 7.69 (d, J=9.1 Hz, 1H), 7.76 (d, J=8.4 Hz, 1H), 7.88 (d, J=8.4 Hz, 1H), 8.77 (s, 1H), 9.12 (s, 1H), 14.60 (br s, 1H), 15.15 (br s, 1H); 13C NMR (100 MHz, CDCl$_3$) δ 62.1, 72.1, 107.4, 108.1, 118.4, 118.9, 121.1, 123.0, 123.2, 126.6, 126.9, 127.2, 127.79, 127.83, 128.4, 129.2, 132.8, 133.2, 135.7, 136.6, 139.2, 160.5, 161.2, 167.4, 172.2; HRMS (FAB, 3-NOBA) calcd for C$_{30}$H$_{25}$N$_2$O$_2$ (M+H)+ 445.1917, obsd 445.1905.

N,N'-Bis(1'-hydroxy-2'-naphthylidene)-(1S)-phenyl-1,2-ethylenediamine (2d)

Salen 2d was obtained following General Procedure A from (1S)-phenyl-1,2-ethylenediamine (197 mg, 1.45 mmol) and 1-hydroxy-2-naphthaldehyde (498 mg, 3.89 mmol), with stirring at 45° C. for 16 h. Purification was achieved by trituration with cold ethanol to give pure 2d (542 mg, 84%): [α]19 D+688 (c 0.75, CH$_2$Cl$_2$); 1H NMR (400 MHz, CDCl$_3$) δ 3.96 (dd, J=13.1, 8.4 Hz, 1H), 4.11 (dd, J=13.1, 4.6 Hz, 1H), 4.75 (dd, J=8.4, 4.6 Hz, 1H), 6.84 (d, J=8.8 Hz, 1H), 6.89 (d, J=8.8 Hz, 1H), 7.04 (s, 2H), 7.33-7.37 (m, 1H), 7.40-7.58 (m, 9H), 7.65 (d, J=7.9 Hz, 1H), 7.88 (s, 1H), 8.25 (s, 1H), 8.39 (d, J=8.3 Hz, 1H), 8.42 (d, J=8.8 Hz, 1H), 13.82 (br s, 1H), 14.46 (br s, 1H); 13C NMR (100 MHz, CDCl$_3$) δ 60.6, 70.9, 109.7, 110.6, 115.8, 117.1, 124.2, 124.9, 125.1, 125.3, 126.8, 127.3, 127.4, 127.5, 128.4, 129.1, 129.3, 129.9, 136.4, 137.0, 138.8, 163.5, 164.5, 166.7, 172.3; HRMS (FAB, 3-NOBA) calcd for C$_{30}$H$_{25}$N$_2$O$_2$ (M+H)+ 445.1917, obsd 445.1925.

N,N'-Bis(3',5'-diiodosalicylidene)-(1S)-phenyl-1,2-ethylenediamine (2e)

The title salen was obtained from (1S)-phenyl-1,2-ethylenediamine (105 mg, 0.77 mmol) and 3,5-diiodosalicylaldehyde (520 mg, 1.38 mmol), following General Procedure A, with stirring at 45° C. for 24 h. Trituration with cold ethanol afforded pure 2e (567 mg, 96%): [α]19 D +46.6 (c 1.00, CH$_2$Cl$_2$); 1H NMR (400 MHz, CDCl$_3$) δ 3.97 (dd, J=12.5, 8.7 Hz, 1H), 4.17 (dd, J=12.5, 4.3 Hz, 1H), 4.72 (dd, J=8.7, 4.3 Hz, 1H), 7.31-7.41 (m, 5H), 7.44 (d, J=2.0 Hz, 1H), 7.48 (d, J=2.0 Hz, 1H), 8.02 (d, J=2.0 Hz, 1H), 8.03 (d, J=2.0 Hz, 1H) 8.05 (s, 1H), 8.18 (s, 1H), 14.25 (br s, 1H), 14.36 (br s, 1H); 13C NMR (100 MHz, CDCl$_3$) δ 65.3, 73.2, 79.5, 79.9, 87.0, 87.5, 119.6, 119.8, 126.8, 128.4, 129.1, 138.9, 140.0, 140.2, 148.9, 160.0, 160.5, 164.0, 165.0; HRMS (FAB, 3-NOBA) calcd for C$_{22}$H$_{17}$O$_2$N$_2$I$_4$ (M+H)+ 848.7470, obsd 848.7496.

N,N'-Bis(4'-benzyloxysalicylidene)-(1S)-phenyl-1,2-ethylenediamine (2f)

Following General Procedure A, salen 2f was obtained From (1S)-phenyl-1,2-ethylenediamine (212 mg, 1.56 mmol) and 4-benzyloxy-2-hydroxybenzaldehyde (630 mg, 2.76 mmol), with stirring at 45° C. for 24 h. Purification was achieved by trituration with cold ethanol, yielding pure 2f (710 mg, 92%): [α]19 D +119 (c 0.96, CH$_2$Cl$_2$); 1H NMR (400 MHz, CDCl$_3$) δ 3.88 (dd, J=12.4, 8.3 Hz, 1H), 4.06 (dd, J=12.4, 4.3 Hz, 1H), 4.61 (dd, J=8.3, 4.3 Hz, 1H), 5.05 (d, J=5.2 Hz, 4H), 6.44-6.56 (m, 4H), 7.06 (d, J=8.6 Hz, 1H), 7.10 (d, J=8.6 Hz, 1H), 7.30-7.45 (m, 15H), 8.12 (s, 1H), 8.28 (s, 1H), 13.65 (brs, 1H), 13.78 (br s, 1H); 13C NMR (1.00 MHz, CDCl$_3$) δ 65.7, 69.87, 69.90, 73.4, 101.96, 101.99, 106.98, 107.04, 112.4, 112.6, 126.9, 127.43, 127.44, 127.7, 128.0, 128.5, 128.8, 132.8, 133.0, 136.32, 136.33, 140.6, 162.49, 162.54, 163.5, 164.4, 164.9, 165.6; HRMS (FAB, 3-NOBA) calcd for C$_{36}$H$_{33}$N$_2$O$_4$ (M+H)+ 557.2441, obsd 557.2434.

N,N'-Bis(8'-hydroxy-1',1',7',7'-tetramethyljulolidinyl-9'-methylidene)-(1S)-phenyl-1,2-ethylenediamine (2g)

Salen 2g was obtained from (1S)-phenyl-1,2-ethylenediamine (126 mg, 0.93 mmol) and 8-hydroxy-1,1,7,7-tetramethyljulolidinyl-9-carboxaldehyde (455 mg, 1.67 mmol), following General Procedure A, after stirring at 45° C. for 24 h, filtration, and washing with cold ethanol. Subsequent recrystallization from ethanol afforded the pure salen (304 mg, 57%): [α]19 D +272 (c 0.91, CH$_2$Cl$_2$); 1H NMR (400 MHz, CDCl$_3$) δ 1.18 (s, 9H), 1.20 (s, 3H), 1.46 (s, 3H), 1.47 (s, 3H), 1.49 (s, 3H), 1.68 (t, J=5.5 Hz, 4H), 1.71-1.75 (m, 4H), 3.09 (t, J=5.5 Hz, 4H), 3.14-3.18 (m, 4H), 3.76 (dd, J=12.1, 8.5 Hz, 1H), 3.97 (dd, J=12.1, 4.3 Hz, 1H), 4.52 (dd, J=8.5, 4.3 Hz, 1H), 6.75 (s, 1H), 6.78 (s, 1H), 7.23-7.26 (m, 1H), 7.34 (t, J=7.5 Hz, 2H), 7.41 (d, J=7.5 Hz, 2H), 7.98 (s, 1H), 8.13 (s, 1H), 13.89 (br s, 1H), 13.92 (br s, 1H); 13C NMR (100 MHz, CDCl$_3$) δ 18.4, 28.47, 28.54, 31.1, 31.2, 31.7, 32.2, 36.6, 40.1, 46.95, 46.98, 47.3, 58.4, 65.8, 73.5, 108.7, 108.8, 114.66, 114.73, 121.5, 121.7, 127.1, 127.2, 127.6, 127.9, 128.5, 142.0, 145.6, 145.7, 160.0, 161.2, 165.4, 165.7; HRMS (FAB, 3-NOBA) calcd for C$_{42}$H$_{55}$N$_4$O$_2$ (M+H)+ 647.4325, obsd 647.4303.

N,N'-Bis(3',5'-di-tert-butylsalicylidene)-(1S)-benzyl-1,2-ethylenediamine (3a)

Salen 3a was obtained by following General Procedure A, from (1S)-benzyl-1,2-ethylenediamine4 (235 mg, 1.57 mmol) and 3,5-di-tert-butylsalicylaldehyde (660 mg, 2.82 mmol, 1.8 equiv.), with heating at 45° C. for 24 h. Filtration and trituration (cold ethanol) provided clean 3a (486 mg, 59%): [α]19 D+42.0 (c 1.15, CH$_2$Cl$_2$); 1H NMR (400 MHz, CDCl$_3$) δ 1.25 (s, 9H), 1.28 (s, 9H), 1.43 (s, 9H), 1.45 (s, 9H), 3.02 (dd, J=13.5, 7.4 Hz, 1H), 3.12 (dd, J=13.5, 5.3 Hz, 1H), 3.75 (m, 2H), 3.95 (dd, J=11.5, 2.6 Hz, 1H), 6.94 (d, J=2.2 Hz, 1H), 7.04 (d, J=2.2 Hz, 1H), 7.21-7.31 (m, 5H), 7.38 (s, 2H), 8.14 (s, 1H), 8.34 (s, 1H), 13.62 (br s, 1H), 13.66 (br s, 1H); 13C NMR (100 MHz, CDCl$_3$) δ 29.37, 29.41, 31.40, 31.43, 34.04, 34.06, 35.0, 41.0, 63.8, 71.4, 117.6, 117.8, 126.0, 126.1, 126.5, 126.98, 127.00, 128.5, 129.6, 136.4, 136.5, 138.1, 139.9, 140.0, 157.98, 158.04, 166.6, 167.7; HRMS (FAB, 3-NOBA) calcd for C$_{39}$H$_{55}$O$_2$N$_2$ (M+H)+ 583.4264, obsd 583.4278.

N,N'-Bis(3'-tert-butylsalicylidene)-(1S)-benzyl-1,2-ethylenediamine (3b)

The title compound was obtained following General Procedure A beginning with (1S)-benzyl-1,2-ethylenediamine (251 mg, 1.67 mmol) and 3-tert-butylsalicylaldehyde (536 mg, 3 mmol, 1.8 equiv.). After heating for 48 h, at 45° C., the precipitate was filtered and triturated with cold ethanol to yield pure 3b (553 mg, 78%): [α]19 D +70.4 (c 1.13, CH$_2$Cl$_2$); 1H NMR (400 MHz, CDCl$_3$) δ 1.42 (s, 9H), 1.44 (s, 9H), 3.02 (dd, J=13.5, 7.5 Hz, 1H), 3.13 (dd, J=13.5, 5.1 Hz, 1H), 3.71-3.78 (m, 2H), 3.97 (br d, J=8.6 Hz, 1H), 6.74 (t, J=15.4, 7.7 Hz, 1H), 6.78 (t, J=15.4, 7.7 Hz, 1H), 6.95 (dd, J=7.5, 1.4 Hz, 1H), 7.06 (dd, J=7.5, 1.3 Hz, 1H), 7.19-7.22 (m, 3H), 7.25-7.31 (m, 4H), 8.08 (s, 1H), 8.33 (s, 1H), 13.79 (br s, 1H), 13.84 (br s, 1H); 13C NMR (100 MHz, CDCl$_3$) δ 29.27, 29.31, 34.8, 40.9, 63.8, 71.3, 117.7, 117.8, 118.4, 118.5, 126.5, 128.5, 129.4, 129.5, 129.6, 129.8, 137.1, 137.3, 137.9, 160.3, 160.4, 166.2, 167.4; HRMS (FAB, 3-NOBA) calcd for C$_{31}$H$_{39}$O$_2$N$_2$ (M+H)+ 471.3012, obsd 471.3018.

N,N'-Bis(2'-hydroxy-1'-naphthylidene)-(1S)-benzyl-1,2-ethylenediamine (3c)

Salen 3c was obtained from (1S)-benzyl-1,2-ethylenediamine (260 mg, 1.73 mmol) and 2-hydroxy-1-naphthaldehyde (537 mg, 3.1 mmol, 1.8 equiv.), following General Procedure A, with heating for 20 h at 45° C. Filtration and washing with cold ethanol provided pure salen (500 mg, 70%): [α]19 D −10.8 (c 1.02, CH$_2$Cl$_2$); $^1$H NMR (400 MHz, CDCl$_3$) δ 3.09 (dd, J=13.7, 8.0 Hz, 1H), 3.19 (dd, J=13.7, 5.4 Hz, 1H), 3.80 (dd, J=12.8, 7.9 Hz, 1H), 3.89-3.95 (m, 1H), 4.06 (dd, J=12.8, 3.7 Hz, 1H), 6.93 (d, J=9.2 Hz, 1H), 6.99 (d, J=9.2 Hz, 1H), 7.16-7.27 (m, 5H), 7.28-7.39 (m, 4H), 7.56 (app t, J=7.1 Hz, 2H), 7.63 (dd, J=7.9, 1.2 Hz, 3H), 7.81 (d, J=8.4 Hz, 1H), 8.67 (s, 1H), 8.82 (s, 1H), 14.62 (br s, 1H), 14.78 (br s, 1H); 13C NMR (100 MHz, CDCl$_3$) δ 40.4, 59.4, 68.8, 107.4, 107.5, 118.3, 118.6, 121.7, 122.90, 122.92, 122.95, 126.6, 126.9, 127.0, 127.6, 127.8, 128.7, 128.9, 129.0, 129.5, 132.9, 133.1, 135.7, 136.5, 136.8, 160.45, 160.50, 168.9, 172.2; HRMS (FAB, 3-NOBA) calcd for C$_{31}$H$_{27}$N$_2$O$_2$ (M+H)+ 459.2073, obsd 459.2060.

N,N'-Bis(3',5'-di-tert-butylsalicylidene)-(1S)-benzyl-1,2-ethylenediamine (3a)

Salen 3a was obtained following General Procedure A with (1S)-benzyl-1,2-ethylenediamine (235 mg, 1.57 mmol) and 3,5-di-tert-butylsalicylaldehyde (660 mg, 2.82 mmol, 1.8 equiv.) and heating at 45° C. for 24 h. Filtration and trituration (cold ethanol) afforded clean 3a (486 mg, 59%): [α]19 D +42.0 (c 1.15, CH$_2$Cl$_2$); 1H NMR (400 MHz, CDCl$_3$) δ 1.25 (s, 9H), 1.28 (s, 9H), 1.43 (s, 9H), 1.45 (s, 9H), 3.02 (dd, J=13.5, 7.4 Hz, 1H), 3.12 (dd, J=13.5, 5.3 Hz, 1H), 3.75 (m, 2H), 3.95 (dd, J=11.5, 2.6 Hz, 1H), 6.94 (d, J=2.2 Hz, 1H), 7.04 (d, J=2.2 Hz, 1H), 7.21-7.31 (m, 5H), 7.38 (s, 2H), 8.14 (s, 1H), 8.34 (s, 1H), 13.62 (br s, 1H), 13.66 (br s, 1H); 13C NMR (100 MHz, CDCl$_3$) δ 29.37, 29.41, 31.40, 31.43, 34.04, 34.06, 35.0, 41.0, 63.8, 71.4, 117.6, 117.8, 126.0, 126.1, 126.5, 126.98, 127.00, 128.5, 129.6, 136.4, 136.5, 138.1, 139.9, 140.0, 157.98, 158.04, 166.6, 167.7; HRMS (FAB, 3-NOBA) calcd for C$_{39}$H$_{55}$O$_2$N$_2$ (M+H)+ 583.4264, obsd 583.4278.

N,N'-Bis(3'-tert-butylsalicylidene)-(1S)-benzyl-1,2-ethylenediamine (3b)

To obtain the title compound, General Procedure A was followed, beginning from (1S)-benzyl-1,2-ethylenediamine (251 mg, 1.67 mmol) and 3-tert-butylsalicylaldehyde (536 mg, 3 mmol, 1.8 equiv.). After heating for 48 h, at 45° C., the precipitated was filtered and triturated with cold ethanol to yield pure 3b (553 mg, 78%): [α]19 D +70.4 (c 1.13, CH$_2$Cl$_2$); (400 MHz, CDCl$_3$) δ 1.42 (s, 9H), 1.44 (s, 9H), 3.02 (dd, J=13.5, 7.5 Hz, 1H), 3.13 (dd, J=13.5, 5.1 Hz, 1H), 3.71-3.78 (m, 2H), 3.97 (br d, J=8.6 Hz, 1H), 6.74 (t, J=15.4, 7.7 Hz, 1H), 6.78 (t, J=15.4, 7.7 Hz, 1H), 6.95 (dd, J=7.5, 1.4 Hz, 1H), 7.06 (dd, J=7.5, 1.3 Hz, 1H), 7.19-7.22 (m, 3H), 7.25-7.31 (m, 4H), 8.08 (s, 1H), 8.33 (s, 1H), 13.79 (br s, 1H), 13.84 (br s, 1H); 13C NMR (100 MHz, CDCl$_3$) δ 29.27, 29.31, 34.8, 40.9, 63.8, 71.3, 117.7, 117.8, 118.4, 118.5, 126.5, 128.5, 129.4, 129.5, 129.6, 129.8, 137.1, 137.3, 137.9, 160.3, 160.4, 166.2, 167.4; HRMS (FAB, 3-NOBA) calcd for C$_{31}$H$_{39}$O$_2$N$_2$ (M+H)+ 471.3012, obsd 471.3018.

N,N'-Bis(2'-hydroxy-1'-naphthylidene)-(1S)-benzyl-1,2-ethylenediamine (3c)

Salen 3c was obtained from (1S)-benzyl-1,2-ethylenediamine (260 mg, 1.73 mmol) and 2-hydroxy-1-naphthaldehyde (537 mg, 3.1 mmol, 1.8 equiv.), following General Procedure A, with heating for 20 h at 45° C. Filtration and washing with cold ethanol provided pure salen (500 mg, 70%): [α]19 D −10.8 (c 1.02, CH$_2$Cl$_2$); 1H NMR (400 MHz, CDCl$_3$) δ 3.09 (dd, J=13.7, 8.0 Hz, 1H), 3.19 (dd, J=13.7, 5.4 Hz, 1H), 3.80 (dd, J=12.8, 7.9 Hz, 1H), 3.89-3.95 (m, 1H), 4.06 (dd, J=12.8, 3.7 Hz, 1H), 6.93 (d, J=9.2 Hz, 1H), 6.99 (d, J=9.2 Hz, 1H), 7.16-7.27 (m, 5H), 7.28-7.39 (m, 4H), 7.56 (app t, J=7.1 Hz, 2H), 7.63 (dd, J=7.9, 1.2 Hz, 3H), 7.81 (d, J=8.4 Hz, 1H), 8.67 (s, 1H), 8.82 (s, 1H), 14.62 (br s, 1H), 14.78 (br s, 1H); 13C NMR (100 MHz, CDCl$_3$) δ 40.4, 59.4, 68.8, 107.4, 107.5, 118.3, 118.6, 121.7, 122.90, 122.92, 122.95, 126.6, 126.9, 127.0, 127.6, 127.8, 128.7, 128.9, 129.0, 129.5, 132.9, 133.1, 135.7, 136.5, 136.8, 160.45, 160.50, 168.9, 172.2; HRMS (FAB, 3-NOBA) calcd for C$_{31}$H$_{27}$N$_2$O$_2$ (M+H)+ 459.2073, obsd 459.2060.

N,N'-Bis(1'-hydroxy-2'-naphthylidene)-(1S)-benzyl-1,2-ethyl enediamine (3d)

Salen 3d was obtained from (1S)-benzyl-1,2-ethylenediamine (266 mg, 1.77 mmol) and 1-hydroxy-2-naphthaldehyde (549 mg, 3.19 mmol, 1.8 equiv.), following General Procedure A, with heating for 10 h at 45° C. Filtration, followed by washing with cold ethanol provided the pure product (630 mg, 86%): [α]19D +816 (c 0.23, CH$_2$Cl$_2$); 1H NMR (400 MHz, CDCl$_3$) δ 3.05 (dd, J=13.7, 8.1 Hz, 1H), 3.15 (dd, J=13.7, 5.4 Hz, 1H), 3.71 (dd, J=12.8, 8.0 Hz, 1H), 3.77-3.83 (m, 1H), 3.95 (dd, J=12.8, 3.5 Hz, 1H), 6.89 (dd, J=8.6, 6.2 Hz, 2H), 6.93 (dd, J=8.7, 4.3 Hz, 2H), 7.18-7.32 (m, 5H), 7.40-7.65 (m, 6H), 7.81 (s, 1H), 7.94 (s, 1H), 8.39 (d, J=7.5

Hz, 1H), 8.41 (d, J=7.7 Hz, 1H), 13.85 (br s, 1H), 14.11 (br s, 1H); 13C NMR (100 MHz, CDCl$_3$) δ 40.5, 58.3, 68.2, 109.8, 110.0, 116.0, 116.6, 124.4, 124.8, 125.20, 125.24, 127.0, 127.30, 127.32, 127.35, 127.46, 128.3, 128.8, 129.4, 129.58, 129.9, 136.60, 136.63, 137.0, 163.7, 163.8, 168.5, 172.2; HRMS (FAB, 3-NOBA) calcd for C$_{31}$H$_{27}$N$_2$O$_2$ (M+H)+ 459.2073, obsd 459.2086.

N,N'-Bis(3',5'-diiodosalicylidene)-(1S)-benzyl-1,2-ethylenediamine (3e)

Salen 3e was synthesized from (1S)-benzyl-1,2-ethylenediamine (214 mg, 1.437 mmol) and 3,5-diiodosalicylaldehyde (960 mg, 2.57 mmol, 1.8 equiv.), following General Procedure A, with heating for 24 h at 45° C. Filtration and washing with cold ethanol provided pure 3e (840 mg, 76%): [=]19 D +43.9 (c 1.41, CH$_2$Cl$_2$); 1H NMR (400 MHz, CDCl$_3$) δ 2.93 (dd, J=13.6, 8.1 Hz, 1H), 3.10 (dd, J=13.6, 4.4 Hz, 1H), 3.71-3.80 (m, 2H), 4.03. (br d, J=10.2 Hz, 1H), 7.11 (br d, J=7.0 Hz, 1H), 7.19-7.30 (m, 4H), 7.45 (d, J=2.0 Hz, 1H), 7.72 (s, 1H), 7.99 (d, J=2.0 Hz, 1H), 8.01 (d, J=2.0 Hz, 1H), 8.08 (s, 1H), 14.31 (br s, 1H), 14.36 (br s, 1H); 13C NMR (100 MHz, CDCl$_3$) δ 40.7, 63.1, 70.9, 79.4, 79.6, 87.3, 87.5, 119.5, 119.6, 127.0, 128.7, 129.4, 136.7, 139.9, 140.0, 148.8, 148.9, 160.3, 160.6, 163.8, 164.9; HRMS (FAB, 3-NOBA) calcd for C$_{23}$H$_{19}$O$_2$N$_2$I$_4$ (M+H)+862.7625, obsd 862.7643.

N,N'-Bis(4'-benzyloxysalicylidene)-(1S)-benzyl-1,2-ethylenedi amine (3f)

Salen 3f was obtained from (1S)-benzyl-1,2-ethylenediamine (256 mg, 1.71 mmol) and 4-benzyloxy-2-hydroxybenzaldehyde (701 mg, 3.07 mmol, 1.8 equiv.), following General Procedure A, with heating at 45° C. for 24 h. Purification was achieved by trituration (cold ethanol) to give clean salen (867 mg, 99%): [a]19 D+99.5 (c 0.84, CH$_2$Cl$_2$); 1H NMR (400 MHz, CDCl$_3$) δ 2.96 (dd, J=13.5, 7.8 Hz, 1H), 3.09 (dd, J=13.5, 4.4 Hz, 1H), 3.62-3.68 (m, 2H), 3.89 (d, J=8.8 Hz, 1H), 5.05 (s, 4H), 6.43 (dd, J=8.6, 2.3 Hz, 1H), 6.46 (dd, J=8.6, 2.3 Hz, 1H), 6.52 (dd, J=3.8, 2.4 Hz, 2H), 6.96 (d, J=8.6 Hz, 1H), 7.08 (d, J=8.6 Hz, 1H), 6.96-7.44 (m, 15H), 7.91 (s, 1H), 8.15 (s, 1H), 13.72 (br s, 2H); 13C NMR (100 MHz, CDCl$_3$) δ 40.8, 63.0, 69.9, 70.8, 101.9, 102.0, 106.9, 107.0, 112.4, 112.5, 126.5, 127.5, 128.0, 128.4, 128.6, 129.5, 132.7, 132.8, 136.35, 136.37, 137.8, 162.4, 162.6, 163.8, 164.5, 164.6, 165.5; HRMS (FAB, 3-NOBA) calcd for C$_{37}$H$_{35}$N$_2$O$_4$ (M+H)+ 571.2597, obsd 571.2578.

N,N'-Bis(1'-hydroxy-2'-naphthylidene)-(1S)-benzyl-1,2-ethylenediamine (3d)

Salen 3d was obtained from (1S)-benzyl-1,2-ethylenediamine (266 mg, 1.77 mmol) and 1-hydroxy-2-naphthaldehyde (549 mg, 3.19 mmol, 1.8 equiv.), following General Procedure A, with heating for 10 h at 45° C. Filtration, followed by washing with cold ethanol provided the pure product (630 mg, 86%): [α]19 D +816 (c 0.23, CH$_2$Cl$_2$); 1H NMR (400 MHz, CDCl$_3$) δ 3.05 (dd, J=13.7, 8.1 Hz, 1H), 3.15 (dd, J=13.7, 5.4 Hz, 1H), 3.71 (dd, J=12.8, 8.0 Hz, 1H), 3.77-3.83 (m, 1H), 3.95 (dd, J=12.8, 3.5 Hz, 1H), 6.89 (dd, J=8.6, 6.2 Hz, 2H), 6.93 (dd, J=8.7, 4.3 Hz, 2H), 7.18-7.32 (m, 5H), 7.40-7.65 (m, 6H), 7.81 (s, 1H), 7.94 (s, 1H), 8.39 (d, J=7.5 Hz, 1H), 8.41 (d, J=7.7 Hz, 1H), 13.85 (br s, 1H), 14.11 (br s, 1H); 13C NMR (100 MHz, CDCl$_3$) δ 40.5, 58.3, 68.2, 109.8, 110.0, 116.0, 116.6, 124.4, 124.8, 125.20, 125.24, 127.0, 127.30, 127.32, 127.35, 127.46, 128.3, 128.8, 129.4, 129.58, 129.9, 136.60, 136.63, 137.0, 163.7, 163.8, 168.5, 172.2; HRMS (FAB, 3-NOBA) calcd for C$_{31}$H$_{27}$N$_2$O$_2$ (M+H)+ 459.2073, obsd 459.2086.

N,N'-Bis(3',5'-di-tert-butylsalicylidene)-(1S)-(α-naphthylmethyl)-1,2-ethylenediamine (4a)

The requisite diamine, (1S)-(α-naphthylmethyl)-1,2-ethylenediamine (4), was prepared as its dihydrochloride salt, from 3-(α-naphthyl)-L-alanine (Chem-Impex International, 98.5%). 54a was obtained following General Procedure A from (1S)-(α-naphthylmethyl)-1,2-ethylenediamine dihydrochloride (150 mg, 0.549 mmol), 3,5-di-tert-butylsalicylaldehyde (172 mg, 1.1 mmol) and NEt3 (153 μL, 1.1 mmol), and heating at 70° C. for 1 h, followed by stirring another 5 h at room t. Filtration and trituration with ice-cold ethanol provided pure salen (329 mg, 95%): [α]19 D −36.4 (c 1.26, CH$_2$Cl$_2$); 1H NMR (500 MHz, CDCl$_3$) δ 1.21 (s, 9H), 1.26 (s, 9H), 1.41 (s, 9H), 1.44 (s, 9H), 3.34 (dd, J=13.9, 7.7Hz, 1H), 3.65 (dd, J=13.9, 5.2 Hz, 1H), 3.82 (dd, J=11.7, 4.2 Hz, 1H), 3.90 (m, 1H), 4.0 (dd, J=12, 4.2 Hz, 1H), 6.83 (d, J=2.4 Hz 1H), 7.04 (d, J=2.4 Hz, 1H), 7.33 (m, 4H), 7.47 (dt, J=6.8, 1.1 Hz, 1H), 7.52 (dt, J=6.8, 1.5 Hz, 1H), 7.72 (d, J=7.9 Hz, 1H), 7.85 (d, J=7.7 Hz, 1H), 7.96 (s, 1H), 8.06 (d, J=8.3 Hz, 1H), 8.36 (s, 1H), 13.6 (br s, 1H), 13.7 (br s, 1H); 13C NMR (100 MHz, CDCl$_3$) δ 29.4, 29.44, 31.4, 31.44, 34.02, 34.08, 34.98, 35.0, 37.9, 64.2, 70.4, 77.2, 117.6, 117.8, 123.7, 125.4, 125.6, 126.0, 126.1, 126.1, 127.0, 127.1, 127.4, 128.2, 128.8, 131.9, 133.9, 134.1, 136.4, 136.6, 139.9, 140.0, 157.9, 158.1, 166.6, 167.8; HRMS (FAB, 3-NOBA) calcd for $C_{43}H_{57}N_2O_2$ (M+H)+ 633.442, obsd 633.4440.

N,N'-Bis(3'-tert-butylsalicylidene)-(1S)-(α-naphthylmethyl)-1,2-ethylenediamine (4b)

Salen 4b was obtained from (1S)-(α-naphthylmethyl)-1,2-ethylenediamine (145 mg, 0.728 mmol) and 3-tertbutylsalicylaldehyde (260 mg, 1.46 mmol), following General Procedure A, heating for 2 h at 70° C., followed by stirring for 6 h at rt. Washing with ice-cold ethanol afforded the pure salen (309 mg, 82%): [α]19 D −24.1 (c 1.31, $CH_2Cl_2$); 1H NMR (500 MHz, $CDCl_3$) δ 1.43 (s, 9H); 1.45 (s, 9H), 3.34 (dd, J=13.9, 7.9 Hz, 1H), 3.69 (dd, J=13.8, 4.8 Hz, 1H), 3.86 (dd, J=11.5, 7.1 Hz, 1H); 3.90 (m, 1H), 4.03 (dd J=11.6, 4.4 Hz, 1H), 6.69 (t, J=7.6 Hz, 1H), 6.78 (t, J=7.6 Hz, 1H), 6.83 (d, J=7.5 Hz, 1H), 7.08 (d, J=7.6 Hz, 1H), 7.3 (m, 4H), 7.47 (t, J=7 Hz, 1H), 7.52 (t, J=8.2 Hz, 1H), 7.72 (d, J=8 Hz, 1H), 7.85 (d, J=8 Hz, 1H), 7.89 (s, 1H), 8.07 (d, J=8.3 Hz, 1H), 8.38 (s, 1H), 13.8 (s, 1H); 13.9 (s, 1H); 13C NMR (100 MHz, $CDCl_3$) δ 29.3, 29.3, 34.8, 34.81, 37.8, 64.2, 70.4, 117.7, 117.8, 118.3, 118.5, 123.7, 125.3, 125.6, 126.2, 127.5, 128.2, 128.9, 129.4, 129.6, 129.81, 129.84, 131.9, 133.95, 133.97, 137.15, 137.4, 160.3, 160.4, 166.2, 167.5; HRMS (FAB, 3-NOBA) calcd for $C_{35}H_{41}N_2O_2$ (M+H)+ 521.3168, obsd. 521.3157.

N,N'-Bis(2'-hydroxy-1'-naphthylidene)-(1S)-(α-naphthylmethyl)-1,2-ethylenediamine (4c)

Salen 4c was obtained from (1S)-(α-naphthylmethyl)-1,2-ethylenediamine dihydrochloride (150 mg, 0.549 mmol), 2-hydroxy-1-naphthaldehyde (189 mg, 1.1 mmol) and NEt3 (1.1 mmol), following General Procedure A, with heating for 1 h at 70° C. and stirring for another 6 h at room t. Filtration and crystallization from hot EtOH provided clean 4c (103 mg, 37%): [α]19 D −75.4 (c 1.00, $CH_2Cl_2$); 1H NMR (500 MHz, $CDCl_3$) δ 3.44 (dd, J=13.8, 7.8 Hz, 1H), 3.72 (dd, J=14, 5.1 Hz, 1H), 3.89 (m, 1H), 4.1 (m, 2H), 6.92 (d, J=9.2 Hz, 1H), 6.98 (d, J=9.1 Hz, 1H), 7.15 (t, J=9.6 Hz, 1H), 7.17 (t, J=8.7 Hz, 1H), 7.25 (m, 2H), 7.37 (m, 3H), 7.48 (m, 2H), 7.54 (m, 3H), 7.62 (m, 3H), 7.73 (d, J=7.3 Hz, 1H), 7.81 (d, J=8.4 Hz, 1H), 7.87 (d, J=8 Hz, 1H), 8.06 (d, J=8.4 Hz, 1H), 8.5 (s, 1H), 8.8 (s, 1H), 14.7 (br s, 1H); 14.9 (br s, 1H); 13C NMR (100 MHz, $CDCl_3$) δ 37.4, 59.5, 67.6, 107.3, 107.4, 118.3, 118.5, 121.6, 122.8, 123.19, 125.37, 125.7, 126.4, 126.49, 126.7, 127.5, 127.7, 127.8, 128.3, 128.7, 128.9, 129, 131.5, 132.7, 132.77, 133.1, 133.9, 135.7, 136.5, 160.4, 160.5, 168.9, 172.1; HRMS (FAB, 3-NOBA) calcd for $C_{35}H_{29}N_2O_2$ (M+H)+ 509.2229, obsd 509.2244.

N,N'-Bis(3',5'-diiodosalicylidene)-(1S)-(α-naphthylmethyl)-1,2-ethylenediamine (4e)

Salen 4e was obtained following General Procedure A, from (1S)-(α-naphthylmethyl)-1,2-ethylenediamine dihydrochloride (150 mg, 0.549 mmol), 3,5-diiodosalicylaldehyde (410 mg, 1.1 mmol) and $NEt_3$ (153 μL, 1.1 mmol), heating for 30 min at 70° C., followed by 4 h stirring at room t. Purification was achieved by trituration with cold ethanol to give the final product (415 mg, 83%): [α]19 D −35.9 (c 1.02, $CH_2Cl_2$); 1H NMR (500 MHz, $CDCl_3$) δ 3.29 (dd, J=14, 8.5 Hz, 1H), 3.62 (dd, J=14.5 Hz, 1H), 3.85 (dd, J=12.3, 8.1 Hz, 1H), 3.98 (m, 1H), 4.1 (dd, J=12.4, 2.9 Hz, 1H), 7.18 (d, J=2 Hz, 1H), 7.21 (d, J=6.8 Hz, 1H), 7.33 (t, J=7.1 Hz, 1H), 7.46 (d, J=2 Hz, 1H), 7.52 (m, 2H), 7.74 (d, J=8.2 Hz, 1H), 7.86 (d, J=1H), 7.93 (d, J=8.3 Hz, 1H), 7.98 (d, J=2 Hz, 1H), 8.01 (d, J=2 Hz, 1H), 8.11 (s, 1H), 14.3 (s, 1H), 14.4 (s, 1H); 13C NMR (125 MHz, $CDCl_3$) δ 37.8, 63.3, 69.7, 79.4, 79.5, 87.2, 87.5, 119.4, 119.6, 123.1, 125.4, 125.9, 126.5, 128.0, 128.2, 129.1, 131.6, 132.6, 134, 139.9, 140.0, 148.7, 148.9, 160.3, 160.6, 163.8, 164.9; HRMS (FAB, 3-NOBA) calcd for $C_{27}H_{21}N_2O_2I_4$ (M+H)+ 912.7782, obsd 912.7801.

N,N'-Bis(4'-benzyloxysalicylidene)-(1S)-(α-naphthylmethyl)-1,2-ethylenediamine (4f)

The title salen was accessed from (1S)-(α-naphthylmethyl)-1,2-ethylenediamine (110 mg, 0.549 mmol) and 4-benzyloxysalicylaldehyde (251 mg, 1.10 mmol), following General Procedure A, heating for 2 h at 70° C., followed by stirring for 6 h at rt. Filtration and trituration with cold ethanol gave clean 4f (272 mg, 80%): [α]19 D −27.6 (c 1.12, $CH_2Cl_2$); 1H NMR (500 MHz, $CDCl_3$) δ 3.29 (dd, J=13.9, 8.1 Hz, 1H), 3.62 (dd, J=13.9, 5 Hz, 1H), 3.76 (dd, J=12, 7.2 Hz, 1H), 3.83 (m, 1H), 3.96 (dd, J=12, 3.5 Hz, 1H), 5.03 (s, 2H), 5.04 (s, 2H), 6.35 (d, J=2.4 Hz, 1H), 6.37 (d, J=2.4 Hz, 1H), 6.43 (d, J=2.4 Hz, 1H), 6.45 (d, J=2.4 Hz, 1H), 6.49 (d, J=2.3 Hz, 1H), 6.84 (d, J=8.6 Hz, 1H), 7.07 (d, J=8.6 Hz, 1H), 7.26 (d, J=7.2 Hz, 1H), 7.35 (m, 1H), 7.47 (t, J=6.9 Hz, 1H), 7.53 (dt, J=8.4, 1.3 Hz, 1H), 7.71 (d, J=7.4 Hz, 1H), 7.72 (s, 1H), 7.85 (d, J=7.7 Hz, 1H), 8.01 (d, J=8.3 Hz, 1H), 8.2 (s, 1H), 13.7 (brs, 2H); 13C NMR (100 MHz, $CDCl_3$) δ 37.8, 63.5, 69.7, 69.9, 101.9, 102.0, 106.8, 107.0, 112.3, 112.5, 123.5, 125.4, 125.6, 126.2, 127.4, 127.5, 128.1, 128.2, 128.6, 128.9, 131.8, 132.7, 132.75, 133.8, 133.9, 136.36, 136.38, 162.4, 162.6, 163.8, 164.49, 164.52, 165.7; HRMS (FAB, 3-NOBA) calcd for $C_{41}H_{37}N_2O_4$ (M+H)+ 621.2753, obsd. 621.2733.

N,N'-Bis(8'-hydroxy-1',1',7',7'-tetramethyljulolidinyl-9'-methylidene)-(1S)-α-naphthylmethyl-1,2-ethylenediamine (4g)

A modest precipitate was obtained from (1S)-(α-naphthylmethyl)-1,2-ethylenediamine (150 mg, 0.549 mmol), 8-hydroxy-1,1,7,7-tetramethyljulolidinyl-9-carboxaldehyde (300 mg, 1.1 mmol) and NEt3 (2.2 mmol), following General Procedure A, heating for 1 h at 70° C., followed by stirring for 5 h at room t. Trituration with cold ethanol yielded clean salen 4g (117 mg, 30%): [α]19 D−74.9 (c 0.71, $CH_2Cl_2$); 1H NMR (400 MHz, $CDCl_3$) δ 1.12 (s, 3H), 1.15 (s, 3H), 1.20 (s, 3H), 1.22 (s, 3H), 1.45 (s, 3H), 1.47 (s, 3H), 1.49 (s, 3H), 1.5 (s, 3H), 1.70 (m, 8H), 3.15 (m, 10H), 3.70 (m, 2H), 3.82 (dd, J=11.3, 4.7 Hz, 1H), 6.6 (s, 3H), 6.8 (s, 3H), 7.29 (t, J=6.1 Hz, 1H), 7.33 (t, J=7.1 Hz, 1H), 7.45 (t, J=6.7 Hz, 1H), 7.49 (t, J=8.3 Hz, 1H), 7.67 (s, 1H), 7.68 (d, J=8.7 Hz, 1H), 7.82 (d, J=7.8 Hz, 1H), 8.07 (d, J=5 Hz, 1H), 8.07 (s, 1H), 14 (br s, 1H), 14.1 (br s, 1H); 13C NMR (100 MHz, $CDCl_3$) δ 28.46, 28.53, 31.1, 31.14, 31.6, 31.7, 32.19, 32.2, 36.6, 38, 40.1, 46.9, 47.3, 63.8, 70.0, 108.5, 108.7, 114.6, 114.8, 121.43, 121.6, 124.0, 125.4, 125.9, 126.9, 127.5, 127.6, 128.1, 128.6, 131.9, 133.8, 134.8, 145.4, 145.7, 160.3, 161.0, 164.8, 165.8; HRMS (FAB, 3-NOBA) calcd for $C_{47}H_{59}N_4O_2$ (M+H)+ 711.4638, obsd 711.4619.

N,N'-Bis(3',5'-di-tert-butylsalicylidene)-(1S)-(β-naphthylmethyl)-1,2-ethylenediamine (5a)

The requisite diamine, (1S)-(2-naphthylmethyl)-1,2-ethylenediamine (5), was prepared from 3-(β-naphthyl)-L-alanine (Chem-Impex International, 98.5%). 5a was obtained from (1S)-(β-naphthylmethyl)-1,2-ethylenediamine (145 mg, 0.728 mmol) and 3,5-di-tert-butylsalicylaldehyde (343 mg, 1.46 mmol), following General Procedure A, with stirring overnight at 50° C. Filtration, followed by washing with ice-cold ethanol, provided the pure product (320 mg, 85%): [α]19 D +5.69 (c 1.23, $CH_2Cl_2$); 1H NMR (500 MHz, $CDCl_3$) δ 1.22 (s, 3H), 1.27 (s, 3H), 1.43 (s, 3H), 1.45 (s, 3H), 3.19 (dd, J=13.5, 7.6 Hz, 1H), 3.27 (dd, J=13.5, 5.4 Hz, 1H), 3.73 (dd, J=11.8, 7.7 Hz, 1H), 3.86 (m, 1H), 3.97 (dd, J=11.9, 3.6 Hz, 1H), 6.9 (br s, 1H), 7.04 (br d, J=1.7 Hz, 1H), 7.35 (m, 3H), 7.43 (m, 2H), 7.67 (br s, 1H), 7.77 (m, 3H), 8.15 (br s, 1H), 8.33 (br s, 1H), 13.6 (br s, 2H); 13C NMR (100 MHz, $CDCl_3$) δ 29.38, 29.42, 31.38, 31.44, 34.02, 34.07, 35.0, 41.1, 63.8, 71.3, 77.2, 117.6, 117.8, 125.5, 125.97, 126.0, 126.16, 127.0, 127.6, 127.9, 128.1, 128.2, 132.2, 133.5, 135.6, 136.4, 136.6, 139.9, 140.0, 157.97, 158.05, 166.6, 167.7; HRMS (FAB, 3-NOBA) calcd for $C_{43}H_{57}N_2O_2$ (M+H)+ 633.4420, obsd 633.4413.

N,N'-Bis(3'-tert-butylsalicylidene)-(1S)-(β-naphthylmethyl)-1,2-ethylenediamine (5b)

The title salen was obtained by following General Procedure A, from (1S)-(β-naphthylmethyl)-1,2-ethylenediamine (145 mg, 0.728 mmol) and 3-tert-butylsalicylaldehyde (260 mg, 1.46 mmol), after heating overnight at 50° C. Precipitation was induced by the addition of a small amount of water. Filtration and trituration with ethanol yielded pure 5b (399 mg, 87%): [α]19 D +11.0 (c 1.98, $CH_2Cl_2$); 1H NMR (500 MHz, $CDCl_3$) δ 1.41 (s, 3H), 1.44 (s, 3H), 3.19 (dd, J=13.6, 7.8 Hz, 1H), 3.28 (dd, J=13.6, 5.5 Hz, 1H), 3.76 (dd, J=12.1, 7.6 Hz, 1H), 3.86 (m. 1H), 3.98 (dd, J=12.1, 3.6 Hz, 1H), 6.7 (t, J=7.6 Hz, 1H), 6.77 (t, J=7.6 Hz, 1H), 6.91 (d, J=6.7 Hz, 1H), 7.05 (d, J=6.7 Hz, 1H), 7.27 (dd, J=7.7, 1.5 Hz, 1H), 7.29 (dd, J=7.7, 1.5 Hz, 1H), 7.33 (dd, J=8.3, 1.6 Hz, 1H), 7.42 (m, 2H), 7.67 (s, 1H), 7.76 (m, 3H), 8.12 (s, 1H), 8.32 (s, 1H), 13.8 (br s, 2H); 13C NMR (125 MHz, $CDCl_3$) δ 29.3, 29.35, 34.8, 41.1, 63.8, 71.2, 117.76, 117.83, 118.4, 118.5, 125.5, 126.0, 127.56, 127.6, 127.86, 128.1, 128.2, 129.5, 129.52, 129.8, 129.9, 132.3, 133.5, 135.4, 137.2, 137.4, 160.3, 160.4, 166.2, 167.4; HRMS (FAB, 3-NOBA) calcd for $C_{35}H_{41}N_2O_2$ (M+H)+ 521.3168, obsd 521.3150.

N,N'-Bis(2'-hydroxy-1'-naphthylidene)-(1S)-β-naphthylmethyl)-1,2-ethylenediamine (5c)

Salen 5c was obtained following General Procedure A, stirring overnight at 50° C., from (1S)-(β-naphthylmethyl)-1,2-ethylenediamine (145 mg, 0.728 mmol) and 2-hydroxy-1-naphthaldehyde (252 mg, 1.46 mmol). Purification by trituration with ethanol yielded a bright yellow solid (332 mg, 90%): [α]19 D −7.30 (c 0.61, $CH_2Cl_2$); 1H NMR (500 MHz, DMSO-d6) δ 3.23 (dd, J=13.8, 8.5 Hz, 1H), 3.34 (m, 1H), 4.02 (dd, J=13.1, 3.3 Hz, 1H), 4.41 (m, 1H), 6.74 (d, J=9.3 Hz, 1H), 6.81 (d, J=9.2 Hz, 1H), 7.18 (app q, J=7.7 Hz, 2H), 7.32 (t, J=7.6 Hz, 1H), 7.39 (t, J=7.6 Hz, 1H), 7.48 (m, 2H), 7.62 (d, J=7.8 Hz, 2H), 7.71 (d, J=9.3 Hz, 1H), 7.72 (d, J=9.3 Hz, 1H), 7.84 (m, 4H), 8.02 (d, J=8.4 Hz, 1H), 9.07 (s, 1H), 9.2 (s, 1H), 14.4 (br s, 1H), 14.6 (br s, 1H); 13C NMR (100 MHz, DMSO-d6) δ 56.1, 65.0, 106.4, 106.6, 118.7, 118.8, 122.4, 122.5, 123.1, 124.2, 125.5, 125.8, 126.05, 127.3, 127.4, 127.6, 127.6, 127.7 127.8, 128.7, 131.8, 133.0, 133.3, 133.8, 135.0, 136.1, 136.7, 160.3, 160.7, 172.1, 174.8; HRMS (FAB, 3-NOBA) calcd for $C_{35}H_{29}N_2O_2$ (M+H)+ 509.2229, obsd 509.2242.

N,N'-Bis(1'-hydroxy-2'-naphthylidene)-(1S)-(β-naphthylmethyl)-1,2-ethylenediamine (5d)

The target salen was obtained following General Procedure A, with stirring overnight at 50° C., starting from (1S)-(β-naphthylmethyl)-1,2-ethylenediamine (145 mg, 0.728 mmol) and 1-hydroxy-2-naphthaldehyde (252 mg, 1.45 mmol). Filtration and washing with cold ethanol provided pure 5d was (323 mg, 87%): [α]19 D +536 (c 1.29, $CH_2Cl_2$); 1H NMR (500 MHz, $CDCl_3$) δ 3.22 (dd, J=13.8, 7.9 Hz, 1H), 3.3 (dd, J=13.8, 5.3 Hz, 1H), 3.75 (dd, J=12.8, 7.7 Hz, 1H), 3.91 (m, 1H), 3.97 (dd, J=12.8, 3.6 Hz, 1H), 6.84 (t, J=8.7 Hz, 2H), 6.91 (dd, J=8.35, 1.3 Hz, 2H), 7.33 (dd, J=8.35, 1.3 Hz, 1H), 7.44 (m, 3H), 7.53 (m, 3H), 7.59 (t, J=8.3 Hz, 2H), 7.68 (br s, 1H), 7.77 (m, 3H), 7.85 (br s, 1H), 7.94 (br s, 1H), 8.14 (t, J=8.8 Hz, 1H), 13.9 (br s, 1H), 14.2 (br s, 1H); 13C NMR (125 MHz, $CDCl_3$) δ 40.6, 58.6, 68.2, 109.8, 110.1, 116.03, 116.63, 124.4, 124.8, 125.2, 125.2, 125.8, 126.3, 127.29, 127.3, 127.35, 127.4, 127.46, 127.58, 127.6, 128.2, 128.3, 128.5, 129.4, 129.8, 132.4, 133.5, 134.2, 136.6, 137, 163.8, 163.9, 168.2, 171.8; HRMS (FAB, 3-NOBA) calcd for $C_{35}H_{29}N_2O_2$ (M+H)+ 509.2229, obsd 509.2210.

N,N'-Bis(3',5'-diiodosalicylidene)-(1S)-(β-naphthylmethyl)-1,2-ethylenediamine (5e)

Following General Procedure A, 5e was obtained from (1S)-(β-naphthylmethyl)-1,2-ethylenediamine (145 mg, 0.728 mmol) and 3,5-diiodosalicylaldehyde (547 mg, 1.46 mmol), with stirring overnight at 50° C. Filtration and further purification by trituration (cold ethanol) provided clean salen (571 mg, 85%): [α]19D+7.52 (c 1.05, $CH_2Cl_2$); 1H NMR (400 MHz, $CDCl_3$) δ 3.1 (dd, J=13.6, 8.4 Hz, 1H), 3.26 (dd, J=13.6, 5.1 Hz, 1H), 3.78 (dd, J=12.4, 8 Hz, 1H), 3.89 (m, 1H), 4.06 (dd, J=12.3, 2.7 Hz, 1H), 7.23 (d, J=2 Hz, 1H), 7.25 (m, 1H), 7.44 (m, 3H), 7.58 (br s, 1H), 7.76 (m, 4H), 7.99 (d, J=2 Hz, 1H), 8.01 (d, J=2 Hz, 1H), 8.07 (br s, 1H), 14.4 (br s, 2H); 13C NMR (100 MHz, $CDCl_3$) δ 40.9, 63.1, 70.8, 77.2, 79.5, 79.6, 87.2, 87.5, 119.4, 119.6, 125.8, 126.3, 127.3, 127.5, 127.6, 128.1, 128.4, 132.3, 133.4, 134.2, 134.2, 139.9, 139.95, 148.7, 148.8, 160.2, 160.5, 163.8, 164.9; HRMS (FAB, 3-NOBA) calcd for $C_{27}H_{21}N_2O_2I_4$ (M+H)+ 912.7782, obsd 912.7769.

N,N'-Bis(4'-benzyloxysalicylidene)-(1S)-(β-naphthylmethyl)-1,2-ethylenediamine (5f)

Salen 5f was obtained by heating overnight at 50° C., following General Procedure A, starting from (1S)-(β-naphthylmethyl)-1,2-ethylenediamine (145 mg, 0.728 mmol) and 4-benzyloxysalicylaldehyde (334 mg, 1.46 mmol). Trituration of the precipitated salen with ethanol provided pure salen (413 mg, 91%): [α]19 D +23.8 (c 1.72, $CH_2Cl_2$); 1H NMR (400 MHz, $CDCl_3$) δ 3.11 (dd, J=14.8 Hz, 1H), 3.24 (dd, J=14, 5.2 Hz, 1H), 3.67 (dd, J=12, 7.4 Hz, 1H), 3.75 (m, 1H), 3.92 (dd, J=12, 3.2 Hz, 1H), 5.03 (s, 3H), 5.04 (s, 3H), 6.38 (dd, J=8.6, 2.4 Hz, 1H), 6.43 (dd, J=8.6, 2.4 Hz, 1H), 6.50 (m, 2H), 6.91 (d, J=8.6 Hz, 1H), 7.06 (d, J=8.6 Hz, 1H), 7.4 (m, 13H), 7.63 (br s, 1H), 7.76 (m, 3H), 7.92 (br s, 1H), 8.15 (br s, 1H), 13.7 (br s, 2H); 13C NMR (125 MHz, $CDCl_3$) δ 41.0, 63.2, 69.9, 70.9, 102, 102.1, 106.9, 107.1, 112.4, 112.5, 125.5, 126.04, 127.48, 127.55, 127.6, 127.8, 128.07, 128.1, 128.6, 132.2, 132.7, 132.8, 133.5, 135.4, 136.44, 136.43, 162.5, 162.6, 163.8, 164.5, 164.6, 165.64; HRMS (FAB, 3-NOBA) calcd for $C_{41}H_{36}N_2O_4$ (M+H)+ 621.2753, obsd. 621.2772.

N,N'-Bis(8'-hydroxy-1',1',7',7'-tetramethyljulolidinyl-9'-methylidene)-(1S)-(β-naphthylmethyl)-1,2-ethylenediamine (5g)

Salen 5g was obtained following General Procedure A, from (1S)-(β-naphthylmethyl)-1,2-ethylenediamine (145 mg, 0.728 mmol) and 8-hydroxy-1,1,7,7-tetramethyljulolidinyl-9-carboxaldehyde (400 mg, 1.46 mmol), after heating overnight at 50° C. Filtration and trituration with cold ethanol provided a pure sample (444 mg, 86%): [α]19 D +143 (c 1.54, $CH_2Cl_2$); 1H NMR (400 MHz, $CDCl_3$) δ 1.15 (s, 6H), 1.2 (s, 3H), 1.22 (s, 3H), 1.46 (s, 3H), 1.48 (s, 6H), 1.51 (s, 3H), 1.70 (m, 8H), 3.15 (m, 10H), 3.6 (dd, J=12, 7.1 Hz, 1H), 3.67 (m, 1H), 3.78 (dd, J=12, 1 Hz, 1H), 6.67 (s, 3H), 6.8 (s, 3H), 7.3 (dd, J=8.4, 1.3 Hz, 1H), 7.41 (m, 2H), 7.65 (s, 1H), 7.75 (m, J=8.9 Hz, 3H), 7.87 (s, 1H), 8.02 (s, 1H), 14 (br s, 2H); 13C NMR (100 MHz, $CDCl_3$) δ 28.47, 28.53, 31.1, 31.2, 31.65, 31.7, 32.2, 36.6, 40.13, 41.13, 47.0, 47.35, 63.2, 71, 77.2, 108.6, 108.7, 114.7, 114.8, 121.5, 121.6, 125.2, 125.7, 127.5, 127.56, 127.61, 127.65, 127.8, 128.1, 128.2, 132.1, 133.5, 136.3, 145.5, 145.7, 160.3, 161.15, 164.8, 165.7; HRMS (FAB, 3-NOBA) calcd for $C_{47}H_{59}N_4O_2$(M+H)+ 711.4638, obsd 711.4669.

N,N'-Bis(3',5'-di-tert-butylsalicylidene)-3-O-methyl-4,5-O-isopropylidene-1,2-dideoxy-Dfructopyranosyl-1,2-diamine (6a & 7a)

Diamines 6/7 were obtained as an anomeric mixture (favoring the β-anomer ~9:1 in $CDCl_3$) in three steps [$Tf_2O$, pyridine; (ii) $NaN_3$, DMF; (iii) $H_2$, $PtO_2$] from the known D-fructose derivative, 2-azido-2-deoxy-3-O-methyl-4,5-O-isopropylidene-β-Dfructopyranose. General Procedure A was followed. With heating overnight at 50° C., anomeric diamines 6/7 (162 mg, 0.700 mmol) and 3,5-di-tert-butylsalicylaldehyde (328 mg, 1.40 mmol) $SiO_2$ 14 column chromatography (0→20% Et2O-hexenes), provided both the β-anomer 7a (260 mg, 56%, elutes first) and the α-anomer 6a (87 mg, 19%). β-Anomer (7a): [α]19 D –120 (c 1.00, $CH_2Cl_2$); 1H NMR (600 MHz, $CDCl_3$) δ 1.3 (s, 9H), 1.31 (s, 9H), 1.34 (s, 3H), 1.43 (s, 9H), 1.44 (s, 9H), 1.57 (s, 3H), 3.68 (s, 3H), 3.75 (d, J=12 Hz, 1H), 3.8 (d, J=6 Hz, 1H), 3.93 (dd, J=12, 3.2 Hz, 1H), 3.96 (dd, J=12, 2.3 Hz, 1H), 4.04 (br d, J=12 Hz, 1H), 4.16 (m, 1H), 4.29 (app t, J=6 Hz, 1H), 7.08 (d, J=2 Hz, 1H), 7.16 (d, J=2 Hz, 1H), 7.38 (d, J=2 Hz, 1H), 7.42 (d, J=2 Hz, 1H), 8.36 (s, 1H), 8.61 (s, 1H), 13.4 (s, 1H), 13.6 (s, 1H); 13C NMR (150 MHz, $CDCl_3$) δ 25.8, 27.6, 29.45, 29.49, 31.48, 31.5, 34.13, 34.16, 35.08, 35.11, 60.6, 61.9, 65.1, 73.1, 76.4, 79.9, 90.5, 109.3, 117.7, 118.0, 126.1, 127, 127.2, 127.8, 136.8, 137, 140.0, 140.3, 157.9, 158.3, 165.6, 169.0; HRMS (FAB, 3-NOBA) calcd for $C_{40}H_{60}O_6N_2$ (M+H)+ 665.4530, obsd 665.4551.

α-Anomer (6a): [α]19 D +54.2 (c 4.70, $CH_2Cl_2$); 1H NMR (600 MHz, $CDCl_3$) δ 1.3 (s, 9H), δ 1.31 (s, 9H), 1.33 (s, 3H), 1.43 (s, 9H), 1.43 (s, 9H), 1.44 (s, 3H), 3.58 (d, J=7 Hz, 1H), 3.72 (m, 5H), 4.06 (d, J=13 Hz, 1H), 4.12 (dd, J=12, 5, Hz, 1H), 4.42 (m, 2H), 7.07 (d, J=2 Hz, 1H), 7.18 (d, J=2 Hz, 1H), 7.37 (d, J=2 Hz, 1H), 7.41 (d, J=2 Hz, 1H), 8.34 (s, 1H), 8.63 (s, 1H), 13.3 (s, 1H), 13.6 (br s, 1H); 13C NMR (150 MHz, $CDCl_3$) δ 24.6, 26.9, 29.4, 29.5, 31.5, 34.1, 34.13, 35.04, 35.07, 61.0, 62.8, 71.8, 76.2, 84.5, 91.1, 109.6, 117.7, 117.9, 126.1, 127.2, 127.5, 136.7, 136.8, 140.0, 140.3, 157.9, 158.3, 162.5, 169.0; HRMS (FAB, 3-NOBA) calcd for $C_{40}H_{60}O_6N_2$ (M+H)+ 665.4530, obsd 665.4515.

N,N'-Bis(3'-tert-butylsalicylidene)-3-O-methyl-4,5-O-isopropylidene-1,2-dideoxy-Dfructopyranosyl-1,2-diamine (6b & 7b)

A mixture of diastereomeric salens was obtained from anomeric diamines 6/7 (130 mg, 0.560 mmol) and 3-tert-butylsalicylaldehyde (200 mg, 1.12 mmol), by heating overnight at 50° C., following General Procedure A. Purification by silica gel column chromatography (0→20% Et2O-hexenes), yielded both the β-anomer 7b (170 mg, 55%, elutes first) and the α-anomer 6b (26 mg, 8%).

β-Anomer (7b): [α]19 D –157 (c 2.40, $CH_2Cl_2$); 1H NMR (600 MHz, $CDCl_3$) δ 1.35 (s, 3H), 1.43 (s, 9H), 1.45 (s, 9H), 1.58 (s, 3H), 3.68 (s, 3H), 3.77 (br d, J=12 Hz, 1H), 3.82 (d, J=7 Hz, 1H), 3.92-3.96 (dd, J=13, 3 Hz, 1H), 3.96-4.01 (dd, J=13 Hz, 1H), 4.06 (br d, J=12 Hz, 1H), 4.17-4.2 (m, 1H), 4.32 (app t, J=7 Hz, 1H), 6.81 (app t, J=7 Hz, 1H), 6.84 (app t, J=7 Hz, 1H), 7.13 (d, J=8 Hz, 1H), 7.20 (d, J=8 Hz, 1H), 7.33 (d, J=8 Hz, 1H), 7.37 (d, J=8 Hz, 1H), 8.37 (s, 1H), 8.62 (s, 1H), 13.6 (s, 1H), 13.8 (s, 1H); 13C NMR (150 MHz, $CDCl_3$) δ 25.8, 27.6, 29.3, 29.4, 34.8, 34.9, 60.6, 61.9, 64.9, 73.0, 76.2, 79.7, 90.5 109.5, 117.8, 117.9, 118.5, 118.8, 129.6, 129.9, 130.2, 130.9, 137.6, 137.7, 160.6, 160.7, 165.3, 168.6; HRMS (FAB, 3-NOBA) calcd for $C_{32}H_{44}O_6N_2$ (M+H)+ 553.3279, obsd 553.3277.

α-Anomer (6b): [α]19 D +62.2 (c 1.28, CH2Cl2) 1H NMR (600 MHz, $CDCl_3$) δ 1.31 (s, 3H), 1.41 (s, 9H), 1.43 (s, 9H), 3.61 (d, J=7 Hz, 1H), 3.68-3.71 (m, 5H), 4.06 (br d, J=13 Hz, 1H), 4.10 (dd, J=12.5 Hz, 1H), 4.38-4.43 (m, 2H), 6.78 (app t, J=8 Hz, 1H), 6.82 (app t, J=8 Hz, 1H), 7.09 (dd, J=8, 1.5 Hz, 1H), 7.18 (dd, J=8, 1.5Hz, 1H), 7.31 (dd, J=8, 1.5 Hz, 1H), 7.34 (dd, J=8, 1.5 Hz, 1H), 8.32 (s, 1H), 8.61 (s, 1H), 13.5 (s, 1H), 13.9 (br s, 1H); 13C NMR (150 MHz, $CDCl_3$) δ 24.5, 26.8, 29.3, 15 29.4, 34.8, 34.9, 60.9, 62.6, 62.9, 71.7, 75.8, 83.9, 91.1, 109.6, 117.8, 118.1, 118.4, 118.6, 129.6, 129.9, 130.8, 137.4, 137.6, 160.2, 160.6, 162.2, 168.7; HRMS (FAB, 3-NOBA) calcd for $C_{32}H_{44}O_6N_2$ (M+H)+ 553.3279, obsd 553.3298.

N,N'-Bis(2'-hydroxy-1'-naphthylidene)-3-O-methyl-4,5-O-isopropylidene-1,2-dideoxy-Dfructopyranosyl-1,2-diamine (6c & 7c)

General Procedure A was followed, starting from anomeric diamines 6/7 (162 mg, 0.700 mmol) and 2-hydroxy-1-naphthaldehyde (241 mg, 1.40 mmol), with heating overnight at 50° C. Separation of the product mixture by SiO2 column chromatography (0→55% Et2O-hexenes), provided both the β-anomer 7c (170 mg, 45%, elutes first) and the α-anomer 6c (15 mg, 4%).

β-Anomer (7c): [α]19 D –174 (c 1.05, $CH_2Cl_2$); 1H NMR (600 MHz, $CDCl_3$) δ 1.3 (s, 3H), 1.56 (s, 3H), 3.66 (d, J=7 Hz, 1H), 3.71 (s, 3H), 3.84-3.90 (dd, J=13, 3 Hz, 1H), 3.87-3.93 (br d, J=13 Hz, 1H), 4.03-4.09 (dd, J=13 Hz, 3 Hz, 1H), 4.05-4.12 (br d, J=13 Hz, 1H), 4.19 (m, 1H), 4.36 (app t, J=6 Hz, 1H), 6.85 (d, J=9 Hz, 1H), 6.91 (d, J=9 Hz, 1H) 7.17 (dd, J=8, 1 Hz, 1H), 7.22 (dd, J=8 Hz, 1Hz), 7.32 (dd, J=8 Hz, 1 Hz, 1H), 7.36 (dd, J=7, 1 Hz, 1H), 7.54 (app t, J=7 Hz, 2H), 7.61 (d, J=9 Hz, 1H), 7.64 (d, J=9 Hz, 7.76 (d, J=8 Hz, 1H), 7.81 (d, J=8 Hz, 1H), 8.68 (br d, J=6 Hz, 1H), 8.98 (d, J=6 Hz, 1H), 14.3 (br s, 1H), 14.5 (d, J=6 Hz, 1H); 13C NMR (150 MHz, $CDCl_3$) δ 25.7, 27.7, 59.9, 60.0, 61.6, 72.5, 75.9, 77.2, 79.2, 88.5, 107.2, 108, 109.5, 118, 118.8, 119.1, 122.7, 122.9, 123.3, 124.3, 126.3, 126.7, 127.9, 128.0, 128.9, 129.0, 133.3, 133.4, 137.3, 137.5, 156.5, 160.2, 172.4, 175.8; HRMS (FAB, 3-NOBA) calcd for $C_{32}H_{32}O_6N_2$ (M+H)+ 541.2340, obsd 541.2321.

α-Anomer (6c): 1H NMR (400 MHz, CDCl$_3$) δ 1.27 (s, 3H), 1.34 (s, 3H), 3.65-3.75 (m, 5H), 3.81 (dd, J=12, 6.3 Hz, 1H), 4.05 (br d, J=13 Hz, 1H), 4.20 (dd, J=12, 4.7 Hz, 1H), 4.36 (app t, J=6.9 Hz, 1H), 4.45 (m, 1H), 6.83 (d, J=9.4 Hz, 1H), 7.1 (d, J=9.0 Hz, 1H), 7.29 (app t, J=7.4 Hz, 1H), 7.35 (app t, J=7.6 Hz, 1H), 7.46 (app t, J=7.6 Hz, 1H), 7.52 (d, J=7.8 Hz, 1H), 7.6 (d, J=9.4 Hz, 1H), 7.68 (d, J=7.9 Hz, 1H), 7.75 (d, J=8.3 Hz, 1H) (d, J=9.1 Hz, 1H), 8.06 (d, J=8.5 Hz, 1H), 8.6 (br s, 1H), 9.4 (s, 1H), 14.1 (br s, 1H), 14.8 (s, 1H); 13C NMR (150 MHz, CDCl$_3$) δ 24.4, 26.6, 57.1, 60.7, 62.8, 71.5, 74.9, 83.2, 90.5, 106.8, 108.3, 109.8, 117.9, 119.5, 120.1, 122.8, 123.3, 124.9, 126.2, 127.5, 127.8, 127.9, 128.9, 129.1, 133, 133.8, 135.2, 137.8, 157.6, 159.4, 164.4, 174.8, 177.3; HRMS (FAB, 3-NOBA) calcd for C$_{32}$H$_{32}$O$_6$N$_2$ (M+H)+ 541.2339, obsd 541.2330.

N,N'-Bis(1'-hydroxy-2'-naphthylidene)-3-O-methyl-4,5-O-isopropylidene-1,2-dideoxy-β-Dfructopyranosyl-1,2-diamine (7d)

General Procedure A was followed, beginning from anomeric diamines 6/7 (162 mg, 0.700 mmol) and 1-hydroxy-2-naphthaldehyde (241 mg, 1.40 mmol), with overnight heating at 50° C. SiO2 column chromatography (35% EtOAc-hexenes), yielded pure 7d (188 mg, 50%): [α]19 D −846 (c 0.97, CH$_2$Cl$_2$); 1H NMR (600 MHz, CDCl$_3$) δ 1.33 (s, 3H), 1.53 (s, 3H), 3.65 (d, J=6.8 Hz, 1H), 3.72 (s, 3H), 3.76 (br d, J=13 Hz, 1H), 3.87 (dd, J=13, 3 Hz, 1H), 3.98 (br d, J=13 Hz, 1H), 4.05 (dd, J=13.3 Hz, 1H), 4.2 (m, 1H), 4.39 (app t, J=7 Hz, 1H), 6.79 (d, J=9 Hz, 1H), 6.86 (d, J=9 Hz, 2H), 6.90 (d, J=9 Hz, 1H), 7.41-7.45 (m, 2H), 7.53-7.59 (m, 4H), 7.77 (d, J=16 5 Hz, 1H), 8.10 (d, J=7 Hz, 1H), 8.43 (dd, J=8, 4.8 Hz, 1H), 13.41 (br s, 1H), 13.70 (d, J=7 Hz, 1H); 13C NMR (150 MHz, CDCl$_3$) δ 25.7, 27.6, 59.5, 60.0, 61.9, 72.5, 76, 79.1, 88.3, 109.7, 109.8, 110.6, 115.7, 116.8, 125.0, 125.2, 125.3, 125.4, 127.2, 127.3, 127.7, 127.9, 128.2, 129.2, 130.2, 130.2, 137.2, 137.4, 159.4, 163.4, 171.9, 174.8; HRMS (FAB, 3-NOBA) calcd for C$_{32}$H$_{32}$N$_2$O$_6$ (M+H)+ 541.2340, obsd 541.2320.

N,N'-Bis(3',5'-diiodosalicylidene)-3-O-methyl-4,5-O-isopropylidene-1,2-dideoxy-β-Dfructopyranosyl-1,2-diamine (7e)

Salen 7e was obtained following General Procedure A, heating overnight at 50° C., from anomeric diamines 6/7 (162 mg, 0.700 mmol) and 3,5-diiodosalicylaldehyde (241 mg, 1.40 mmol), with subsequent SiO2 column chromatography (25-50% Et$_2$O-hexenes) (212 mg, 32%): [α]19 D −82.7 (c 0.83, CH2Cl2); 1H NMR (400 MHz, CDCl$_3$) δ 1.33 (s, 3H), 1.54 (s, 3H), 3.57 (s, 3H), 3.81-3.90 (m, 2H), 4.04 (d, J=12.3 Hz, 1H), 4.16-4.19 (m, 1H), 4.29 (app t, J=6.3 Hz, 1H), 7.48 (d, J=2 Hz, 1H), 7.62 (d, J=2 Hz, 1H), 8.04 (d, J=2 Hz, 1H), 8.06-8.07 (m, 2H), 8.33 (s, 1H), 14.10 (s, 1H), 14.30 (br s, 1H); 13C NMR (150 MHz, CDCl$_3$) δ 25.2, 27.2, 60.4, 62.7, 63.9, 72.1, 75, 79, 79.1, 79.9, 87.3, 88.2, 90.2, 109.7, 119.6, 119.8, 140.1, 140.9, 149.1, 149.2, 160.2, 161.4, 162.0, 166.1; HRMS (FAB, 3-NOBA) calcd for C$_{24}$H$_{24}$N$_2$O$_6$I$_4$ (M+H)+ 944.7893, obsd 944.7869.

N,N'-Bis(4'-benzyloxysalicylidene)-3-O-methyl-4,5-O-isopropylidene-1,2-dideoxy-β-Dfructopyranosyl-1,2-diamine (7f)

Salen 7f was obtained following General Procedure A, heating overnight at 50° C., from anomeric diamines 6/7 (162 mg, 0.700 mmol) and 4-benzyloxysalicylaldehyde (319 mg, 1.40 mmol), with subsequent SiO2 column chromatography (25→50% EtOAc-hexenes) (230 mg, 48%): [α]19 D −188 (c 1.00, CH$_2$Cl$_2$); 1H NMR (600 MHz, CDCl$_3$) δ 1.32 (s, 3H), 1.54 (s, 3H), 3.61 (s, 3H), 3.67 (d, J=13 Hz, 1H), 3.7 (d, J=7 Hz, 1H), 3.9 (d, J=3 Hz, 1H), 3.97 (d, J=13 Hz, 1H), 4.15-4.17 (m, 1H), 4.27 (t, J=7 Hz, 1H), 5.06 (s, 1H), 5.07 (s, 1H), 6.45 (dd, J=9, 2 Hz, 1H), 6.49-6.52 (m, 3H), 7.1 (d, J=9 Hz, 1H), 7.19 (d, J=8 Hz, 1H), 7.31 (app t, J=7 Hz, 2H), 7.38 (app t, J=7 Hz, 4H), 7.41 (d, J=7 Hz, 2H), 8.2 (s, 1H), 8.4 (s, 1H), 13.5 (m, 2H); 13C NMR (150 MHz, CDCl$_3$) δ 25.5, 27.5, 60.3, 62.0, 653.7, 69.9, 70.0, 72.6, 76.0, 79.5, 89.9, 102.1, 107.1, 107.3, 109.2, 112.5, 127.4, 127.5, 128, 128.1, 128.5, 128.6, 132.9, 133.6, 136.3, 136.4, 162.9, 163.0, 164.2, 165.5, 166.5; HRMS (FAB, 3-NOBA) calcd for C$_{38}$H$_{40}$O$_8$N$_2$ (M+H)+ 653.2863, obsd 653.2875.

General Procedure B: Synthesis of Cobalt-(III)-Salen Complexes.

To a stirred solution of 'salen' ligand (7e) (43 mg, 0.045 mmol, 1 equiv.) in 5 mL CH$_2$Cl$_2$, a methanolic (2 mL) solution of cobalt (II) acetate tetrahydrate (11.4 mg, 45 µmol, 1.0 equiv.), was added via cannula, under Ar. The Co(II)-salen complex precipitated out as a red solid. After filtration, the Co(II) complex was taken up in CH$_2$Cl$_2$ or toluene (2 mL) and stirred with acetic acid (>10 equiv.) or 3,5-dinitrobenzoic acid (1 equiv.) open to the air. The oxidation was followed by TLC, formation of a greenish-brown spot of lower Rf {Co-(III) complex} from the visibly red, higher Rf spot characteristic of the Co-(II) salen. When TLC indicated the completion of the reaction (2-12 h), the solvent was evaporated, and the Co(III)-salen complex further dried in vacuo. The Co(III) carboxylate complexes so prepared were used for HKR experiments, under ISES (bilayer) conditions or under neat 'Jacobsen' (conventional) conditions.

TABLE S1

MS characterization of Co(III)-salen catalysts.

| Catalyst | Molecular Formula | Calcd | obsd MS (FAB. 3-NOBA) |
|---|---|---|---|
| 1b | C$_{34}$H$_{45}$N$_2$O$_4$Co | 545.3 | 545.2 |
| 1c | C$_{34}$H$_{33}$N$_2$O$_4$Co | 533.2 | 533.1 |
| 1f | C$_{40}$H$_{38}$N$_2$O$_6$Co | 645.2 | 645.1 |
| 1g | C$_{46}$H$_{63}$N$_4$O$_4$Co | 735.4 | 735.3 |
| 2a | C$_{40}$H$_{53}$N$_2$O$_4$Co | 625.3 | 625.4 |
| 2b | C$_{32}$H$_{37}$N$_2$O$_4$Co | 513.2 | 513.2 |
| 2c | C$_{32}$H$_{25}$N$_2$O$_4$Co | 501.1 | 501.1 |
| 2d | C$_{32}$H$_{25}$N$_2$O$_4$Co | 501.1 | 501.1 |
| 2f | C$_{38}$H$_{33}$N$_2$O$_6$Co | 613.2 | 613.2 |
| 2g | C$_{44}$H$_{55}$N$_4$O$_4$Co | 703.3 | 703.3 |
| 3a | C$_{41}$H$_{55}$N$_2$O$_4$Co | 639.3 | 639.4 |
| 3b | C$_{33}$H$_{39}$N$_2$O$_4$Co | 527.2 | 527.2 |
| 3c | C$_{33}$H$_{27}$N$_2$O$_4$Co | 516.1 | 516.1 |
| 3d | C$_{33}$H$_{27}$N$_2$O$_4$Co | 516.1 | 516.1 |
| 3e | C$_{25}$H$_{19}$N$_2$O$_4$I$_4$Co | 918.7 | 918.7 |
| 3f | C$_{39}$H$_{35}$N$_2$O$_6$Co | 627.2 | 627.2 |
| 6a | C$_{42}$H$_{61}$N$_2$O$_8$Co | 721.4 | 721.3 |
| 6b | C$_{34}$H$_{45}$N$_2$O$_8$Co | 609.2 | 609.2 |
| 6c | C$_{34}$H$_{33}$N$_2$O$_8$Co | 597.1 | 597.0 |
| 7a | C$_{42}$H$_{61}$N$_2$O$_8$Co | 721.4 | 721.3 |
| 7b | C$_{34}$H$_{45}$N$_2$O$_8$Co | 609.2 | 609.3 |
| 7c | C$_{34}$H$_{33}$N$_2$O$_8$Co | 597.1 | 597.0 |
| 7d | C$_{34}$H$_{33}$N$_2$O$_8$Co | 597.1 | 597.2 |
| 7f | C$_{40}$H$_{41}$N$_2$O$_{10}$Co | 709.2 | 709.0 |

III. Enzyme Standardization

A. Stock Solutions. The following stock solutions were made for enzyme standardization: 220 mM β-NAD+, 220 mM β-NADP+, alcohol dehydrogenases from horse liver (0.036 nominal EtOH units/µL) and T. brockii (0.147 nominal i-PrOH units/µL) in 25 mM sodium phosphate buffer, pH 7.0 and 2M (R)-1,2-propanediol in H2O. Enzyme units were calculated by measuring the rate of formation of NAD(P)H at 340 nm (vide infra). In each case, one S.I. unit is taken as the amount of enzyme catalyzing the formation of one µmol of NAD(P)H per minute.

B. Standardization of HLADH: The assay cuvette contained the following components: 7.2 mM (33 μL of 220 mM stock) of NAD+, 2 μL of HLADH stock solution, 865 μL of 50 mM sodium pyrophosphate buffer, pH 8.8, and 200 mM (100 μL of 2M stock) of (R)-1,2-propanediol. The reaction was initiated by the addition of the (R)-1,2-propanediol, which typically gave a rate of 0.25±0.01 Abs/min at 25° C., 340 nm. This was indicative of 0.020 U of HLADH per μL of the stock solution.

C. Standardization of TBADH: The assay cuvette contained the following components: 2.2 mM (10 μL 220 mM stock) NADP+, 2 μL of TBADH stock solution, 888 μL of 50 mM sodium pyrophosphate buffer, pH 8.8, and 200 mM (100 μL of 2M stock) of (R)-1,2-propanediol. The reaction was initiated by the addition of the (R)-1,2-propanediol, which typically gave a rate of 0.275±0.001 Abs/min at 25° C., 340 nm. This was indicative of 0.022 U of TBADH per μL of the stock solution.

IV. Dehydrogenase Enantioselectivities

A. Relative Velocity (vrel) Determinations

1. HLADH: The enantioselectivity of TBADH was estimated from the ratios of the initial velocities of (R)- vs. (S)-1,2-propanediol at fixed concentrations between 4.0 and 100 mM at 25° C. Each velocity measurement was made in duplicate. The assay cuvette contained the following: 7.2 mM NAD+ (33 μL from a 220 mM stock), 0.049 U of HLADH, and various concentrations of either the (R)- or (S)-enantiomer of 1,2-propanediol. In all cases, the final volume was adjusted to 1 mL using 50 mM sodium pyrophosphate buffer, pH 8.8. The concentration of NAD+ was fixed at saturating levels here, as reported Km values for NAD+ with HLADH range from 38 to 629 μM.

2. TBADH: The enantioselectivity of TBADH was estimated from the ratios of the initial velocities of (R)- vs. (S)-1,2-propanediol at fixed concentrations between 3.0 and 80 mM at 25° C. Each velocity measurement was performed in triplicate. The assay cuvette contained the following: 2.2 mM NADP+ (10 μL from a 220 mM stock), 0.113 U of TBADH, and various concentrations of either (R) or (S)-enantiomer of 1,2-propanediol. In all cases, the final volume was adjusted to 1 mL using 50 mM sodium pyrophosphate buffer, pH 8.8. The concentration of NADP+ was fixed at saturating levels here, as reported Km value for NADP+ with TBADH is 13 μM.9

Figure 8:
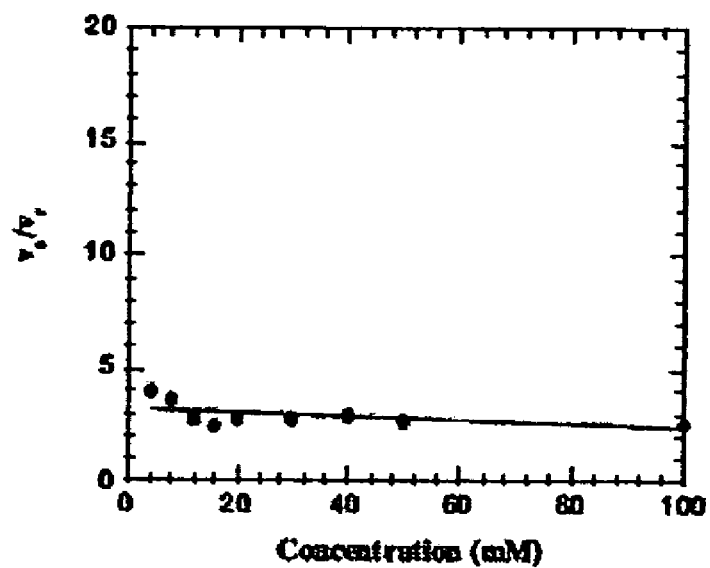
FIG. 8 shows a plot of Dehydrogenase Enantiopreferences vs. 1,2-Propanediol Concentration for HLADH.
Figure 9:
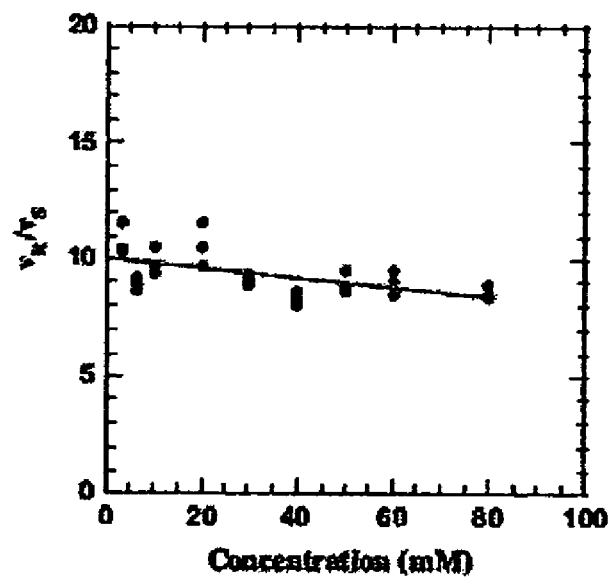
FIG. 9 shows a plot of Dehydrogenase Enantiopreferences vs. 1,2-Propanediol Concentration for TBADH.

The data are collected in FIGS. 8 and 9 and in Table S2 below. One sees that TBADH displayed a significant preference for the (R)-1,2-propanediol, and that HLADH favored the (S)-antipode, though not to the same degree. For each dehydrogenase, the relative velocities are relatively flat as a function of diol concentration [FIGS. 8 and 9]. In each case, there is a slight increase in enantioselectivity as one goes to lower concentration, indicating that each enzyme displays the same enantiomeric preference in the binding step (i.e. lower Km) as in the catalytic step (higher kcat or Vmax).

TABLE S2

Tabulated Dehydrogenase Enantioselectivities vs. Diol Concentration

| | 1,2-Propanediol Conc. (mM) | | | | | | | | |
|---|---|---|---|---|---|---|---|---|---|
| | 4 | 8 | 12 | 16 | 20 | 30 | 40 | 50 | 100 |
| $v_S/v_R$ of HLADH | 4.0 | 3.6 | 2.8 | 2.4 | 2.7 | 2.8 | 3.0 | 2.7 | 2.6 |

TABLE S2-continued

Tabulated Dehydrogenase Enantioselectivities vs. Diol Concentration

| | 1,2-Propanediol Conc. (mM) | | | | | | | | |
|---|---|---|---|---|---|---|---|---|---|
| | 3 | 6 | 10 | 20 | 30 | 40 | 50 | 60 | 80 |
| $v_R/v_S$ of TBADH | 10.8 | 8.9 | 9.9 | 10.6 | 9.1 | 8.4 | 9.0 | 9.1 | 8.6 |

Figure 3:
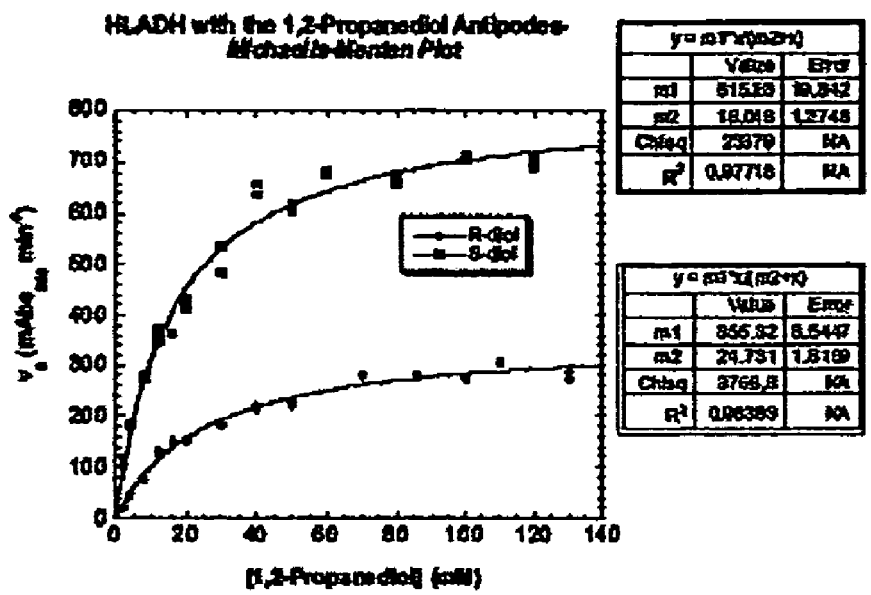
FIG. 3 shows Michaelis-Menten Kinetic Analysis: Km and Vmax Determinations–HLADH.
Figure 4:
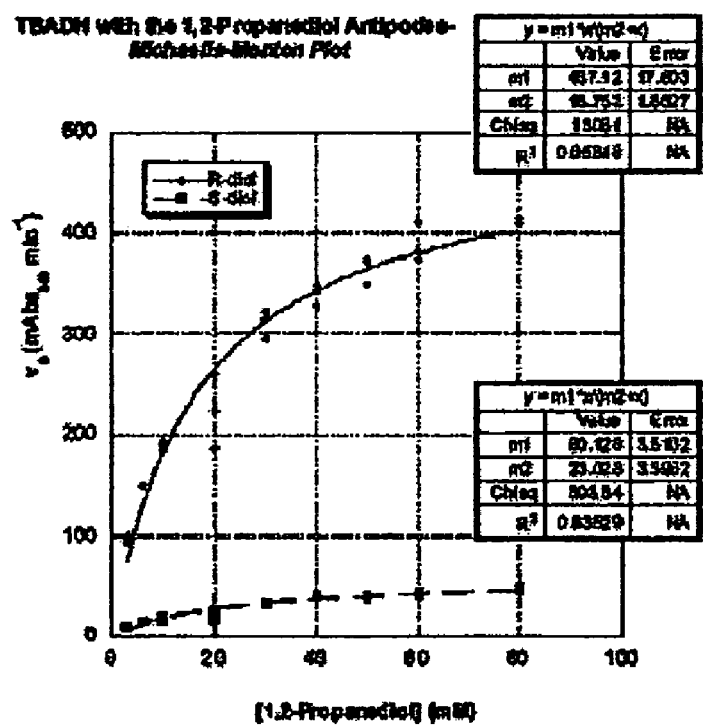
FIG. 4 shows Michaelis-Menten Kinetic Analysis: Km and Vmax Determinations–TBADH.

The flatness of each graph suggests that Km's for the two enantiomers are likely not very different with either dehydrogenase. Indeed, this was confirmed by the determination of Km's for each antipode of 1,2-propanediol for each enzyme. For each antipodal diol, the same data as were used to survey dehydrogenase enantioselectivity, as a function of diol concentration, were plotted in Michaelis-Menten fashion, as v0 vs. [S] (FIGS. 3 and 4). For each dehydrogenase, the data curve for (R)-1,2-propanediol is shown by -■-, and those for the (S)-enantiomer by -●-. In all four cases, the data were processed by linear, least squares fitting to a hyperbolic function. The resulting curve fits and best fit hyperbolic equations are presented above. For HLADH, the following steady state kinetic parameters were obtained:

(R)-1,2-propanediol–Km=25±2 mM and
Vmax=355±9 mAbs min−1 vs.

(S)-1,2-propanediol–Km=16±1 mM and
Vmax=819±20 mAbs min−1.

Translating these data into the ratio of catalytic efficiencies for the two enantiomers, one obtains [(Vmax/Km)S÷(Vmax/Km)R]=3.6. This is consistent with the trends seen in enantioselectivity vs. concentration, as the HLADH enantioselectivity tends toward ~4:1 (S:R) as one tends toward low diol concentrations (see Table S2 and FIGS. 8 and 9).

For TBADH, the following kinetic constants were obtained:

(R)-1,2-propanediol–Km=17±2 mM and
Vmax=487±18 mAbs min−1 vs.

(S)-1,2-propanediol–Km=23±4 mM and Vmax=60±4 mAbs min−1.

Here, the ratio of catalytic efficiencies for the two enantiomeric diols is dominated by the Vmax terms and yields [(Vmax/Km)R÷(Vmax/Km)S]=11. Again, one sees nice agreement with trends observed in the enantioselectivity vs. concentration data, where the enantioselectivity tends toward ~11:1 (R:S) as one tends toward low diol concentrations (see Table S2 and FIGS. 8 and 9).

V. Double Cuvette-ISES (In Situ Enzymatic Screening) Procedure

A general procedure for double cuvette-ISES to estimate both enantioselectivities and relative rates for an array of catalysts being screened in parallel is presented below. The hydrolytic kinetic resolution (HKR) of (±) propylene oxide was chosen as model reaction. An inverted bilayer with $CHC_{13}$ as the organic solvent was chosen for this study, though initial trials indicate that other solvents both more dense (alternative lower organic layers), and less dense (upper organic layer) than the aqueous reporting layer, will also work.

Typically, quartz cuvettes with one cm light paths and with nominal one mL volumes were used. For each catalyst, a two cuvette screen was performed, with cuvette A containing HLADH, as (S)-propanediol-selective reporting enzyme, and cuvette B containing TBADH, as a (R)-propanediol-selective reporting enzyme. For each cuvette, the final volume was 800

μL (300 μL of organic layer; 500 μL of aqueous layer). This experimental set-up sent the spectrophotometer light beam cleanly through the aqueous reporting layer, as control experiments established that the beam passes through 1 mL cuvettes between the 600 and 700 μL volume levels.

A. Organic Layer Composition:

Both cuvettes A and B had the following composition: 150 μL (2.15 mmol) of (±)-propylene oxide (7.2 M in organic layer), 150 μL of CHCl₃ and 0.25 mol % Co(III)-salen catalyst. The total organic layer volume was maintained as 300 μL in all catalyst screens.

B. Aqueous Layer Composition:

(i) Cuvette A: 0.35 U HLADH (17.6 μL from a stock solution (0.02 U/μL)), 7.2 mM β-NAD+(16.5 μL from a 220 mM stock) and 465.8 μL of 50 mM sodium pyrophosphate buffer, pH 8.8. The final pH was 8.6.

(ii) Cuvette B: 0.35 U TBADH (15.8 μL from a stock solution (0.022 U/μL)) of, 2.2 mM β-NADP+ (5 μL from a 220 mM stock) and 479.5 μL of 50 mM sodium pyrophosphate buffer, pH 8.8. The final pH was 8.6. The total volume of the aqueous layer was maintained as 500 μL in both cuvettes in all ISES experiments.

C. Step by Step Protocol: A catalyst stock solution (22 μmol of catalyst in 620 μL CHCl₃) was made up in a 1.5 ml microcentrifuge tube, and stored on ice, along with a stock of (±)-propylene oxide, in a separate tube. The organic layers were prepared by briefly vortexing 150 μL (5.4 μmol, 0.25 mol %) of the catalyst stock in CHCl₃ with 150 μL (2.15 mmol) of (±)-propylene oxide in iced microcentrifuge tubes. These were loaded into 1 mL quartz cuvettes using precooled (refrigerator), disposable 1 mL syringes. The aqueous layers were then layered on top of the organic layers, by syringe, down the walls of the cuvette. A reversed loading method was adapted for the catalysts made using 1-hydroxy-2-naphthaldehyde (aldehyde 'd') in order to get a clear bilayer. In particular, it was found practical for these catalysts to load the aqueous layer first. Then, the organic layer was syringed beneath the aqueous layer. Catalyst screens were routinely run in duplicate (i.e. two runs of cuvette A and two of cuvette B per screen), with ISES rates taken as the average of the two ΔO.D.340/time values obtained, for the appropriate time window (vide infra).

VI. Estimation of Enantioselectivity for Catalysts Screened

Previously, in monitoring transition metal-mediated allylic substitution chemistry, ISES conditions were found in which a reliable signal could be obtained in 10-20 min. For 'fast' catalysts, it was found that a 15 minute time window sufficed to provide meaningful ISES rates in the two reporting cuvettes, allowing for catalyst characterization. This time window was employed for all catalysts displaying rates surpassing 50 mAbs/min (fastest rate of the two reporting cuvettes). For catalysts exhibiting ISES rates ≦50 mAbs/min over the first 15 minutes, a longer observation window was chosen (35 minute total), so as to obtain a better signal. Generally, catalysts displaying ISES rates of less than 20 mAbs/min over 35 minutes were not pursued further.

The following expression was used to estimate catalyst enantioselectivity:

$$\text{Catalyst Enantioselectivity} = \frac{[R]}{[S]} = \frac{\left[\left(\frac{Sel_{E2}}{Sel_{E1}}\right) \cdot v_{E2} - v_{E1}\right]}{Sel_{E2} \cdot (v_{E1} - v_{E2})}$$

where the velocities in each of the reporting enzyme cuvettes, vE1 and vE2, respectively, were taken as the ΔAbs₃₄₀/time values (typically the average of two runs) seen over the time window.

The parameters, $Sel_{E1}$ and $Sel_{E2}$, were taken as the observed reporting enzyme enantioselectivies @ 40 mM diol concentrations (see Table S2):

SelHLADH=$E1$=vR/vS (HLADH)@40 mM=0.34

SelTBADH=$E2$=vR/vS (TBADH)@40 mM=8.4.

This approximation was chosen, based upon the following considerations. Control experiments established that under ISES conditions, 1,2-propanediol concentrations in the aqueous layer were in the range of 2-100 mM, for active catalysts over the observed time window.

The enantiomeric excesses predicted from the double cuvette-ISES data, using this equation and empirical selectivity factors, for Co(III)-salen complexes in the library, indexed by salen, are displayed in the upper number in each box in Table S3 below. For comparison purposes, ee's determined for the same catalysts under standard 'Jacobsen conditions' (neat propylene oxide, no co-solvent, 0.55 equiv. H2O, 3 h reaction time) are displayed below each prediction in the lower number.

TABLE S3

Measured vs. Predicted Enantiomeric Excesses for the Catalyst Library

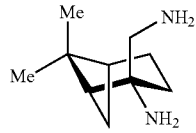

| a | b | c | d |
|---|---|---|---|
| +56 | +68 | § | +75 |
| +72 | +75 |   | +81 |

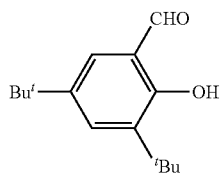

1

TABLE S3-continued
Measured vs. Predicted Enantiomeric Excesses for the Catalyst Library
| Structure | | | | |
|---|---|---|---|---|
| 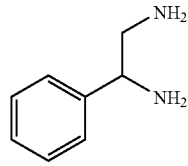<br>2 | −97<br>−93 | −73<br>−75 | § | −15<br>−54 |
| 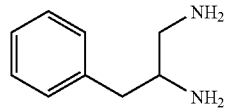<br>3 | +48<br>+55 | +70<br>+57 | § | −54<br>−30 |
| 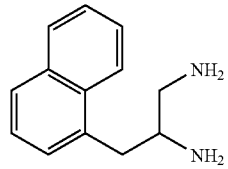<br>4 | +77<br>+76 | +91<br>+59 | § | ¶ |
| 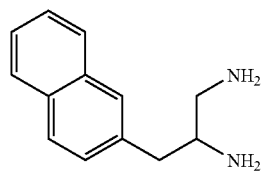<br>5 | +87<br>+66 | +65<br>+68 | § | +9<br>+11 |
| 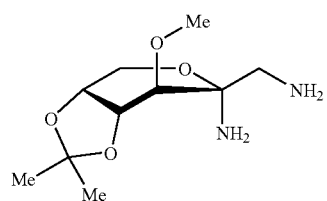<br>6 | +77*<br>+69* | +70*<br>+42* | § | ¶ |
| 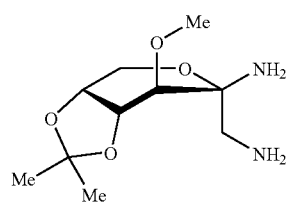<br>7 | −33*<br>−59* | −28*<br>−40* | § | § |

TABLE S3-continued

Measured vs. Predicted Enantiomeric Excesses for the Catalyst Library

| Catalyst | e | f | g |
|---|---|---|---|
| 1 (diamine with Me, Me, NH₂, NH₂) | +47↑ / +28 | § | § |
| 2 (1-phenylethane-1,2-diamine) | +4 / −41 | § | −41# / −71 |
| 3 (phenylpropane-1,2-diamine) | § | § | ¶ |
| 4 (1-naphthylpropane-1,2-diamine) | +43# / +14 | +57 / +51 | § |
| 5 (2-naphthylpropane-1,2-diamine) | +35 / −5 | § | § |
| 6 (sugar-derived diamine) | ¶ | ¶ | ¶ |

TABLE S3-continued

Measured vs. Predicted Enantiomeric Excesses for the Catalyst Library

| Structure | | | |
|---|---|---|---|
| [Structure of compound 7: diacetone-protected sugar with two NH₂ groups] 7 | +87 (+85)*<br>+81 (+83)* | § | ¶ |

Each box provides data for the Co(III)-salen acetate derived from the indicated salen. Presented are the % ee of the 1,2-propanediol product, as predicted by double-cuvette ISES (upper number), and as observed by chiral HPLC (lower number). The cuvette experiments are run in a bilayer of pH 8.6 buffer over 7.2 M epoxide in CHCl₃, containing 0.25 mol % catalyst, for 15-35 min. 'Inherent' catalyst ee's are judged by running the HKR in neat propylene oxide, containing 0.55 equiv. of H2O, also at 0.25 mol % catalyst. §These catalysts gave ISES signals <20 mAbs min−1 over 35 min. †This catalyst was tested at 0.05 mol %, as it was especially fast. #The catalysts derived from 2 g and 4e displayed ISES rates of 14.9 and 18.1 mAbs min−1, respectively, in the HLADH cuvette, over 35 min. ¶Difficulty was encountered in synthesizing appreciable quantities of these salens. *The 3,5-dinitrobenzoate counterion was employed for these Co (III) catalysts.

VII. Estimation of Relative Rates for Catalysts Screened

Figure 6:
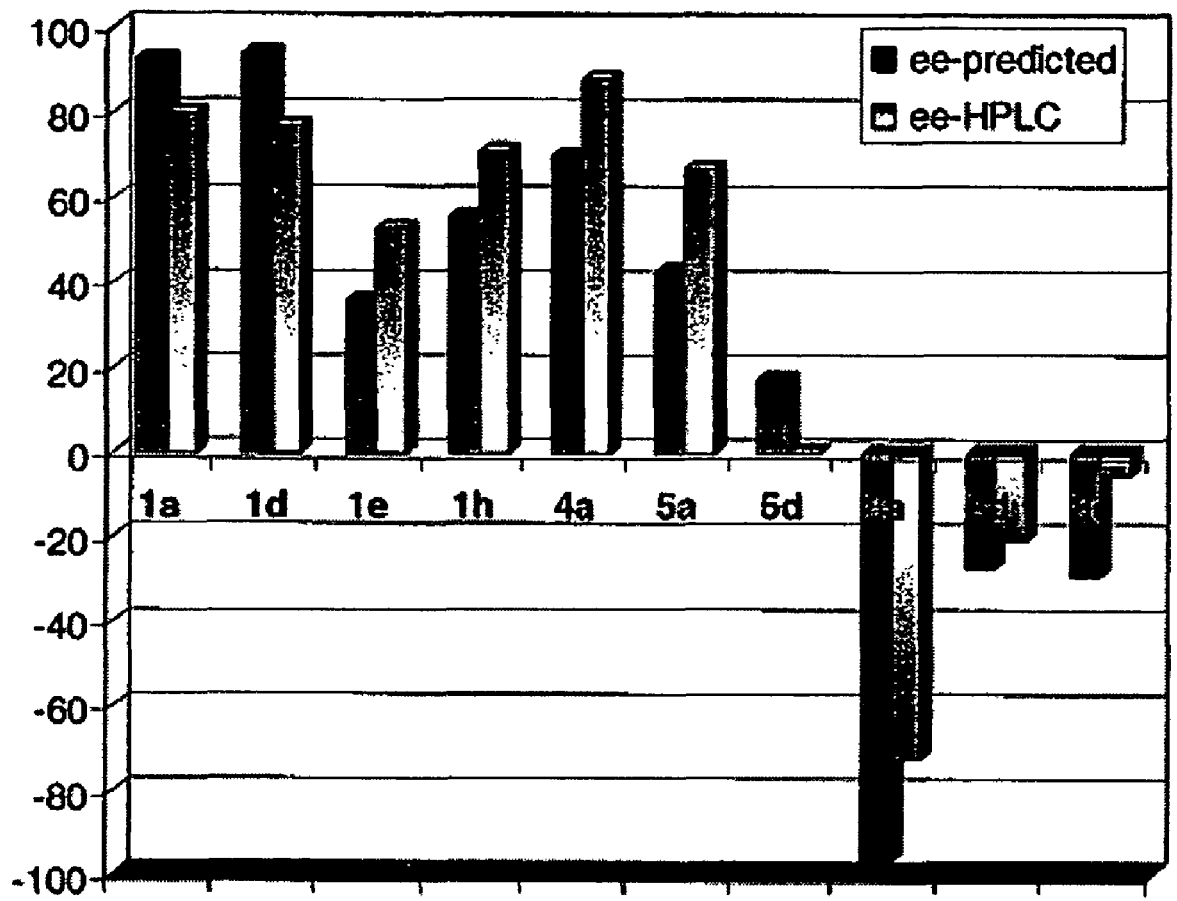
FIG. 6 shows a comparison of predicted and observed ee's for the HKR of hexane oxide.

In order to rank catalysts in terms of relative rate, ISES rates, vE1 and vE2, over the 15 minute time window, were imported into the expression for [total diol]catalyst A/[total diol]catalyst B shown below. Note that the selectivity factors used here, SelE1 and SelE2, are the same as those used in the expression for enantioselectivity just discussed (Section VI). For comparison purposes, these relative rate rankings were compared with actual rate data obtained by observing diol formation by 1H NMR (vide infra, Section IX). Since those empirical data were normalized to the rate of the catalyst derived from salen 3b, the predicted relative rates were similarly normalized. A comparison of the predicted and observed rates is presented in FIG. 6.

$$\frac{([R]^A + [S]^A)}{([R]^B + [S]^B)} = \frac{v_{E1}^A \cdot \left\{1 + \frac{\left(\frac{Sel_{E2}}{Sel_{E1}}\right) \cdot (v_{E1}^B - v_{E2}^B)}{\left[\left(\frac{Sel_{E2}}{Sel_{E1}}\right) \cdot v_{E2}^B - v_{E1}^B\right]}\right\}}{v_{E1}^B \cdot \left\{1 + \frac{\left(\frac{Sel_{E2}}{Sel_{E1}}\right) \cdot (v_{E1}^A - v_{E2}^A)}{\left[\left(\frac{Sel_{E2}}{Sel_{E1}}\right) \cdot v_{E2}^A - v_{E1}^A\right]}\right\}} \cdot \frac{\left\{1 + \frac{Sel_{E2} \cdot (v_{E1}^A - v_{E2}^A)}{\left[\left(\frac{Sel_{E2}}{Sel_{E1}}\right) \cdot v_{E2}^A - v_{E1}^A\right]}\right\}}{\left\{1 + \frac{Sel_{E2} \cdot (v_{E1}^B - v_{E2}^B)}{\left[\left(\frac{Sel_{E2}}{Sel_{E1}}\right) \cdot v_{E2}^B - v_{E1}^B\right]}\right\}}$$

wherein:
- A and B are two chiral catalysts,
- $Sel_{E1}$ or $Sel_{E2}$=$v_{rel}$(R:S) of the reporting enzyme for the diol substrate, and
- V represents the observed rate with catalyst A or B and enzyme E1 or E2.

VIII. Independent Measures of Enantioselectivity

A. Standard Jacobsen Conditions

Salens in the fully synthetic, 42 member focused library that led to catalysts with appreciable activity, as indicated by double cuvette-ISES, were also evaluated 'outside of the cuvette,' under conditions more typically employed in HKR reactions. Specifically, these Co(III)-salen catalysts were evaluated in the HKR of (±)-propylene oxide, under neat conditions, similar to those described by Jacobsen and coworkers. Reactions were arbitrarily stopped after 3 hours, to obtain the enantiopurity of the 1,2-propanediol product at relatively early reaction times, for comparison with ISES predictions.

A typical procedure follows: To the Co(III)-salen catalyst derived from 7e (5.4 mg, 5.4 µmol, 0.25 mol %) and (±)-propylene oxide (125 mg, 2.15 mmol) at 0° C., was added water (21 µL, 1.18 mmol, 0.55 equiv.). The reaction mixture was securely capped, and allowed to warm to room temperature and stirred, most commonly for a total of 3 hours. Percent conversion at 3 hours was evaluated by 1H NMR of an aliquot (cooled to 0° C. for the transfer), in CDCl₃. In most of these cases, the conversion was low enough after 3 hours, that the unreacted epoxide (bp 32° C.) was of relatively low ee, and was therefore removed by evaporation under aspirator vacuum. When the conversion was less than 5% by NMR after 3 hours, reactions were continued for longer times.

Upon termination of the reaction, the diol product was isolated by Kugelrohr distillation (~120° C.-oven temp; 0.1 torr). To determine ee, the isolated diol was derivatized using p-bromobenzoyl imidazole (2.2 equiv.) in THF in the presence of NaH (4 equiv.) at room temperature for 5 min. The bis(p-bromobenzoate) esters obtained following sequential washes with 1 N HCl and saturated sodium bicarbonate, were of sufficient purity to be used directly for chiral HPLC analysis (Chiralcel OD, 99% hexene/i-PrOH).

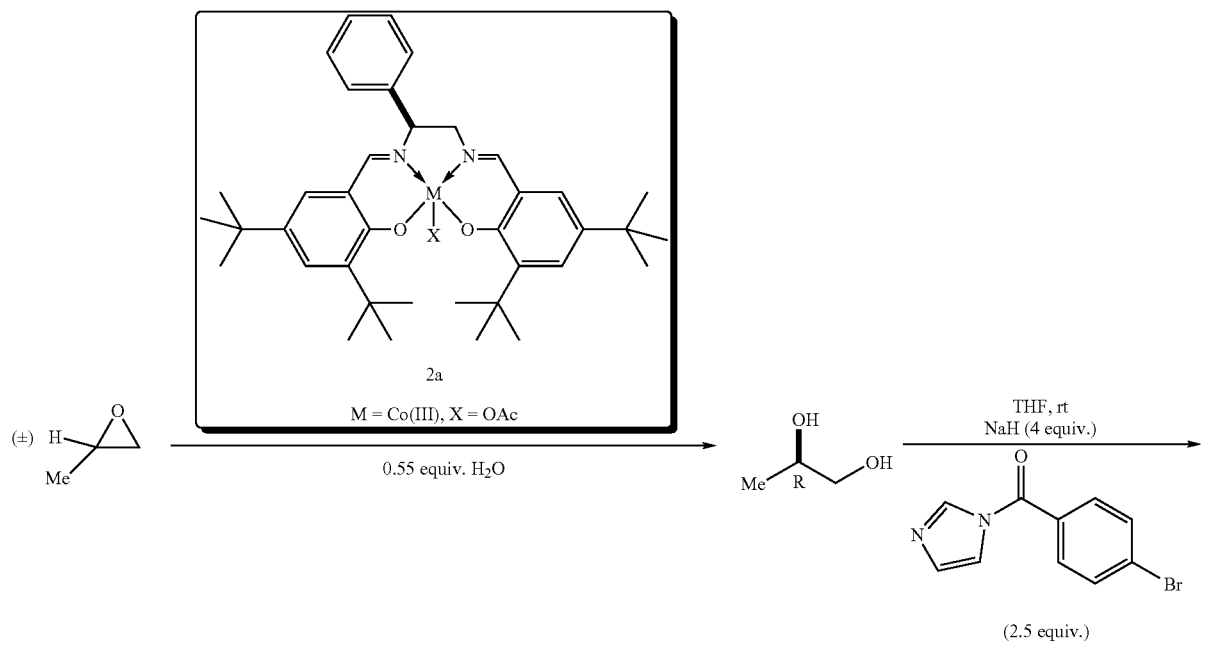
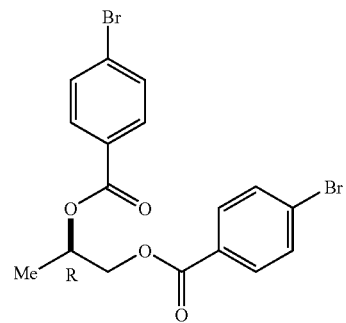
Solvent: i-PrOH/hexane (1:99); Flow Rate = 1 mL/min
Retention Time: 13.9 (R) and 15.8 (S)
Integration: 161.7:5.56 (93% ee)

-continued
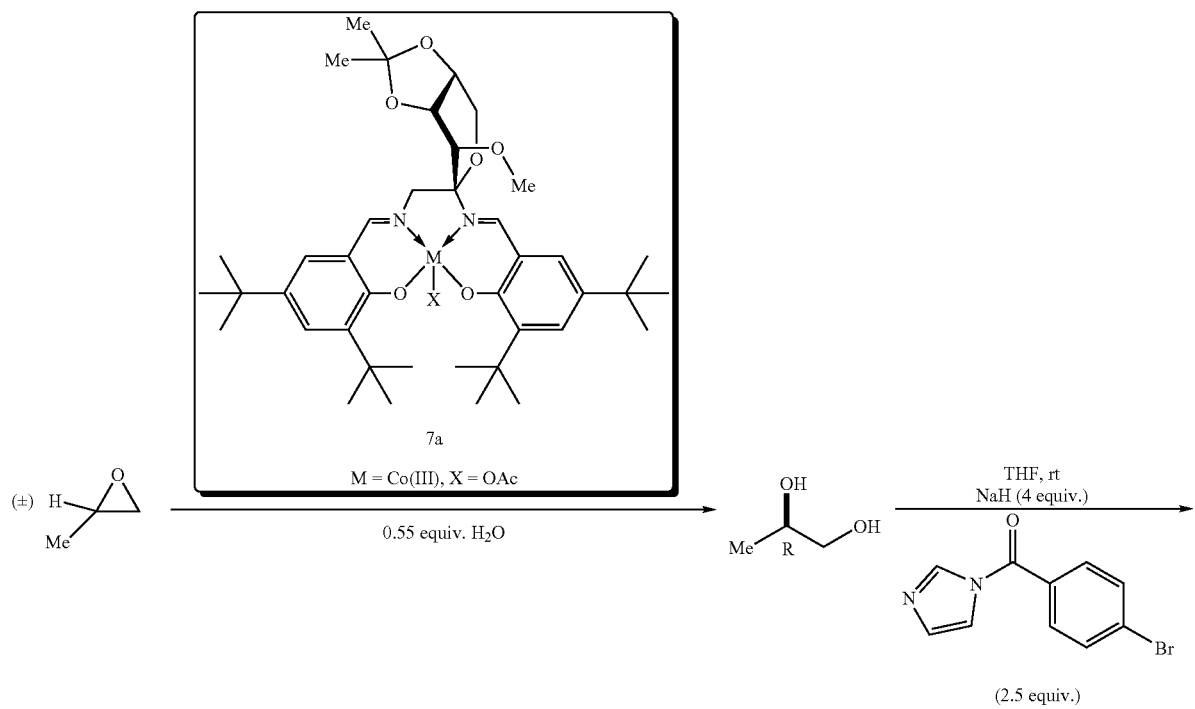
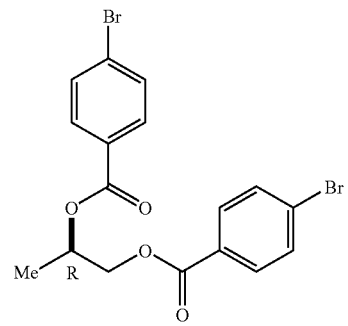
Solvent: i-PrOH/hexane (1:99); Flow Rate = 1 mL/min
Retention Time: 14.1 (R) and 16.1 (S)
Integration: 376.6:135.6 (47% ee)

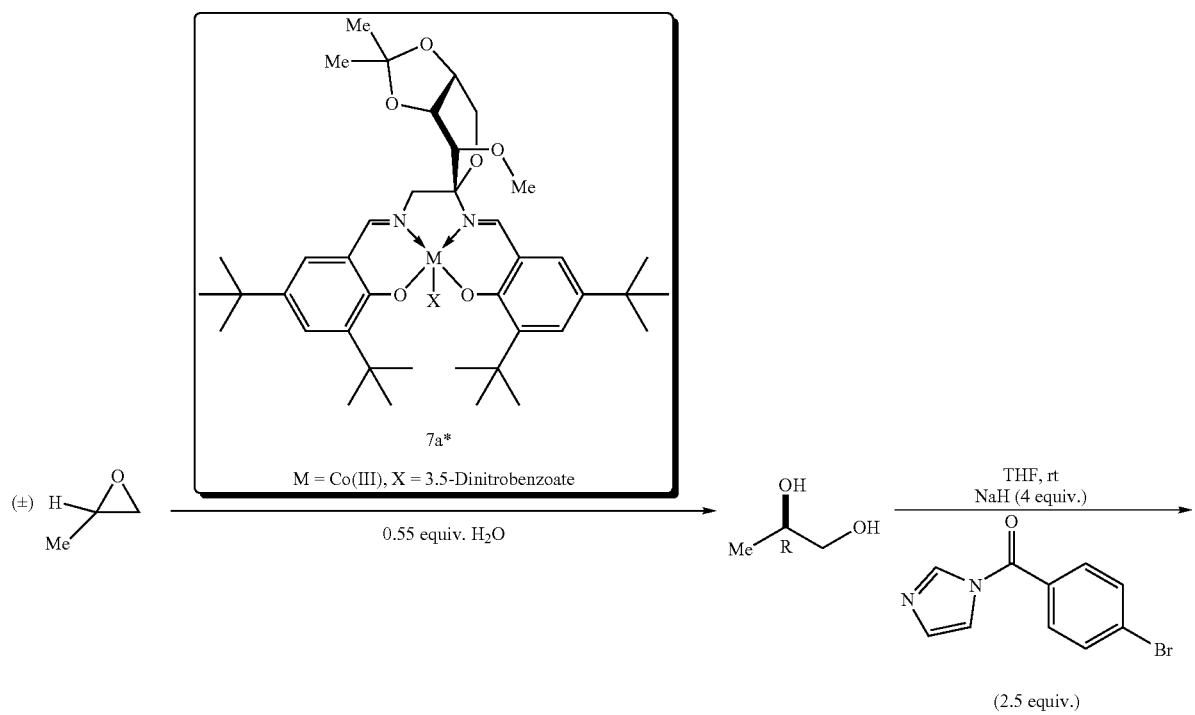
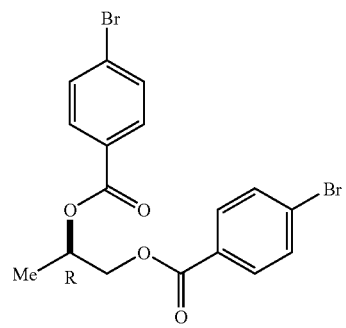
Solvent: i-PrOH/hexane (1:99); Flow Rate = 1 mL/min
Retention Time: 14.5 (R) and 16.6 (S)
Integration: 135.1:29.2 (64% ee)

-continued
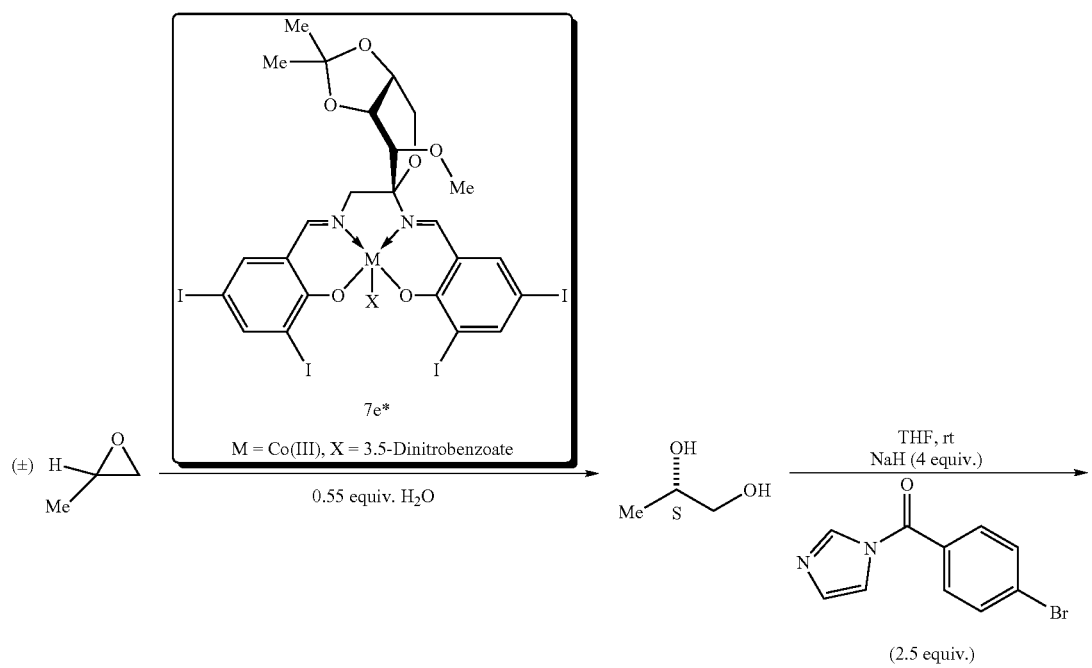
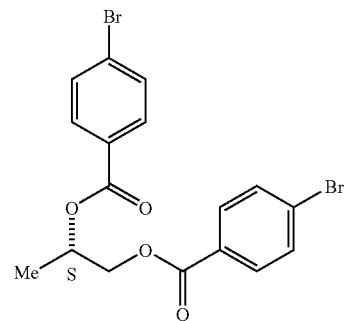
Solvent: i-PrOH/hexane (1:99); Flow Rate = 1 mL/min
Retention Time: 14.5 (R) and 16.4 (S)
Integration: 10.1:135.3 (86% ee)

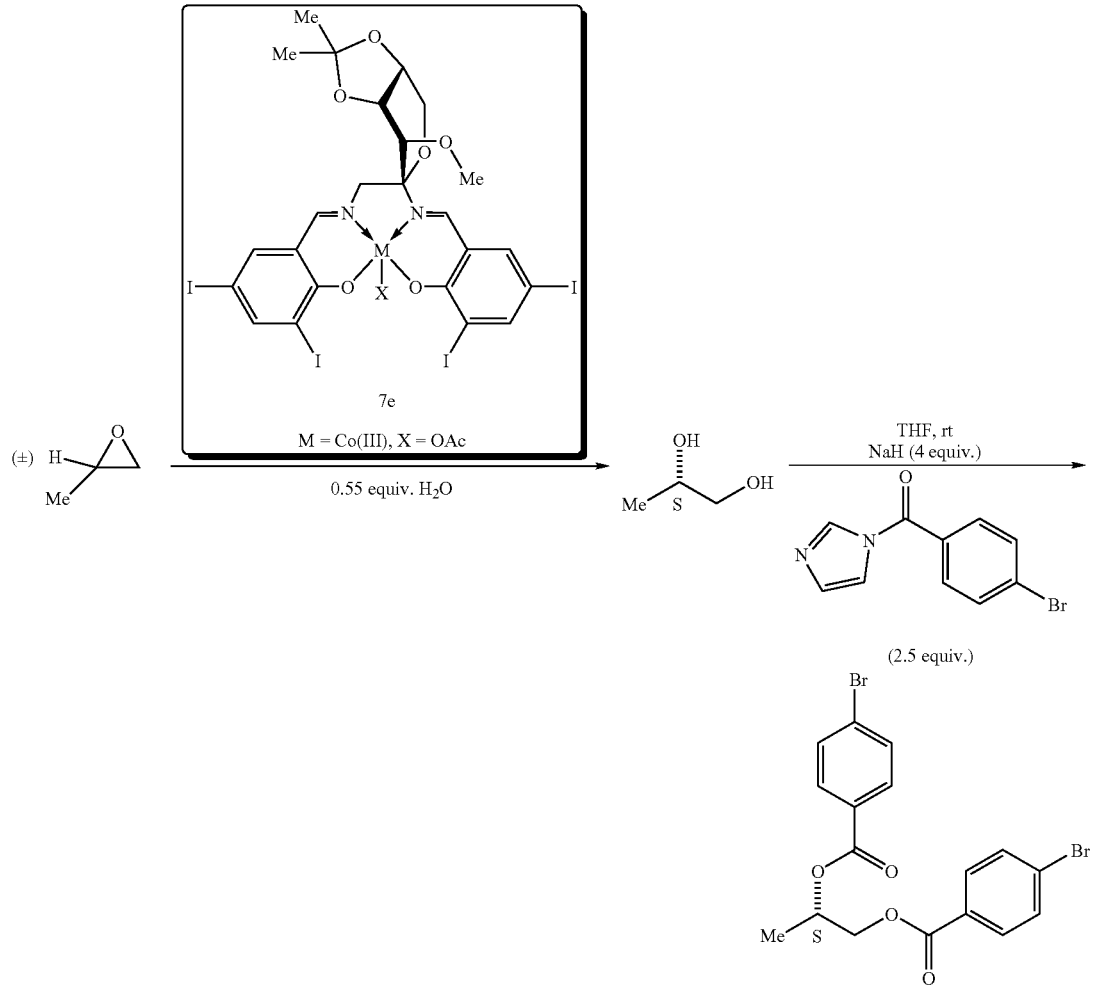

Solvent: i-PrOH/hexane (1:99); Flow Rate = 1 mL/min
Retention Time: 13.7 (R) and 15.6 (S)
Integration: 12.5:152.2 (85% ee)

A tabulation of observed ee's (chiral HPLC), percent conversions (NMR), isolated yields (Kugelrohr distallation) is presented in Table S4, below. Representative chiral HPLC traces are provided below

TABLE S4

HKR Under Standard 'Jacobsen Conditions' with Co(III)-Salen Catalyst 'Hits'

| Salen | Loading (mol %) | NMR conv. (time) | % Yield (time) | % ee (HPLC) |
|---|---|---|---|---|
| 1a | 0.25 | 12 (3 h) | 14 (3 h) | +72 (S) |
| 2a | 0.25 | 17 (3 h) | 24 (5 h) | −93 (R) |
| 3a | 0.25 | 46 (3 h) | 39 (3 h) | +55 (S) |
| 4a | 0.25 | 35 (3 h) | 26 (3 h) | +76 (S) |
| 5a | 0.25 | 36 (3 h) | 30 (3 h) | +66 (S) |
| 6a* | 0.25 | 12 (3 h) | 16 (3 h) | +69 (S) |
| 7a* | 0.25 | 7 (3 h) | 6 (3 h) | −59 (R) |
| 1b | 0.25 | n.d. | 35 (3 h) | +75 (S) |
| 2b | 0.25 | 26 (3 h) | 29 (3 h) | −75 (R) |
| 3b | 0.25 | n.d. | 17 (3 h) | +57 (S) |
| 4b | 0.25 | 50 (3 h) | 32 (3 h) | +59 (S) |
| 5b | 0.25 | 45 (3 h) | 36 (3 h) | +68 (S) |

TABLE S4-continued

HKR Under Standard 'Jacobsen Conditions' with Co(III)-Salen Catalyst 'Hits'

| Salen | Loading (mol %) | NMR conv. (time) | % Yield (time) | % ee (HPLC) |
|---|---|---|---|---|
| 6b* | 0.25 | 11 (3 h) | 12 (3 h) | +42 (S) |
| 7b* | 0.25 | 9 (3 h) | 13 (3 h) | −40 (R) |
| 3c | 0.25 | none obs | | |
| 7c | 0.25 | none obs | | |
| 1d | 0.25 | n.d. | 21 (1 h), 33 (3 h) | +81@1 h, +67@3 h (S) |
| 2d | 0.25 | 19 (22 h) | 15 (22 h) | −54 (R) |
| 3d | 0.25 | 10 (3 h) | 7 (3 h) | −30 (R) |
| 5d | 0.25 | 10 (3 h) | 9 (3 h) | +11 (S) |
| 1e | 0.25 | n.d. | 36 (3 h) | +28 (S) |
| 2e | 0.25 | 26 (3 h) | 18 (3 h) | −41 (R) |
| 4e | 0.25 | 6 (24 h) | 6 (24 h) | +14 (S) |
| 5e | 0.25 | 3 (3 h) | 3 (3 h) | −5 (R) |
| 7e | 0.25 | 33 (3 h) | 12 (3 h) | +81 (S) |
| 7e* | 0.05 | 10 (3 h) | 16 (3 h) | +83 (S) |
| 4f | 0.25 | 24 (21 h) | 23 (21 h) | +51 (S) |

TABLE S4-continued

HKR Under Standard 'Jacobsen Conditions' with Co(III)-Salen Catalyst 'Hits'

| Salen | Loading (mol %) | NMR conv. (time) | % Yield (time) | % ee (HPLC) |
|---|---|---|---|---|
| 2g | 0.25 | n.d. | 1 (3 h), 4 (20 h) | −71@3 h, −65@20 h (R) | n.d. = not determined;
*Indicates that the Co(III)-3,5-dinitrobenzoate catalyst was used. All other entries are for Co(III)-salen-acetate catalysts.

B. Catalyst Performance in the ISES Cuvette

For several catalysts, control experiments were run to assess whether running the HKR under biphasic conditions influences the enantioselectivity of these Co(III)-salen HKR catalysts. In such cases, parallel duplicate 'double-cuvette' runs were chosen (i.e. two HLADH cuvettes and two TBADH cuvettes for a single catalyst). Following the ISES runs, the contents of all four reporting cuvettes were merged. Unreacted epoxide was rapidly removed under Ar stream. Following dilution with $CH_2Cl_2$ (~50 mL), sodium sulfate was added to adsorb remaining water. The resulting organic solution was filtered and the filter cake washed with $CH_2Cl_2$ (2×20 mL). Following evaporation of the solvent, the crude diols were derivatized directly with p-bromobenzoyl imidazole to yield the 1,2-propanediol bis(pbromobenzoate) esters, which were then purified by silica gel chromatography to estimate diol yields. Enantiomeric excesses were determined using chiral HPLC, as before. As can be seen from Table S5, there is no appreciable erosion of ee seen in running these HKR experiments under biphasic conditions. Indeed, the ee's seen from diol isolated directly out of the cuvette generally appear slightly higher than those obtained under 'Jacobsen conditions,' probably reflecting the shorter reaction times employed in the ISES experiment.

TABLE S5

Biphasic vs. 'Jacobsen Conditions'

| Co(III)-salen (indexed by salen) | % Yield (isolated) | % $ee_{measured}$ biphasic conds. | % $ee_{measured}$ neat 'Jacobsen conditions' | % $ee_{predicted}$ double cuvet-ISES |
|---|---|---|---|---|
| 1a | 1 | 87 | 72 | 56 |
| 4a | 1.6 | 82 | 76 | 77 |
| 7a* | <1 | −55 | −59 | −33 |
| 7e | 0.4 | 85 | 81 | 87 |

*denotes that the Co(III)-salen-3,5-dinitrobenzoate catalyst was used in this case. All other entries refer to runs with Co(III)-salen-acetate catalysts.

The concentration of 1,2-propanediol in the aqueous layer was estimated under typical ISES conditions using 1H NMR spectroscopy. The bilayer was prepared as usual for double cuvette-ISES (Section V), but for the substitution of $D_2O$ for $H_2O$ in the buffer, and the elimination of the dehydrogenase enzymes. After 15 min, the aqueous layer (300 μL of 500 μL total) was withdrawn and mixed with a fresh solution of imidazole of known concentration (also 300 μL in D2O), as an internal concentration standard. Accumulation of the 1H NMR spectrum, followed by integration and quantitation, provided an experimental measure of [total diol] in the aqueous reporting layer at t=15 minutes for the catalyst under investigation. The observed diol concentrations for ten catalysts examined in this way are collected in Table S6, below. These have been normalized to the value for the catalyst derived from salen 3b (arbitrarily assigned a rate of 1.0).

TABLE S6

Co(III)-salen-Mediated HKR: [total 1,2-Propanediol] by NMR (aqueous ISES layer)

| | Salen | | | | | | | | | |
|---|---|---|---|---|---|---|---|---|---|---|
| | 1a | 2a | 2b | 1d | 3b | 4b | 7e | 5a | 5b | 5d |
| [diol] (mM) @ 15 min | 19 | 27.5 | 22 | 91 | 96 | 98 | 37 | 52.5 | 75.5 | 54 |
| Norm. | 0.20 | 0.29 | 0.23 | 0.95 | 1.0 | 1.02 | 0.39 | 0.55 | 0.79 | 0.56 |

The following examples illustrate the invention with respect to an in situ enzymatic screening (ISES) method to predict the enantioselectivity of chiral catalysts for the hydrolytic kinetic resolution (HKR) of (±) hexene oxide. Above, it was shown that the method of the invention may be employed to predict the enantioselectivity and relative rate of a catalyst library for HKR of (±)-propylene oxide using horse liver alcohol dehydrogenase (HLADH) and *Thermoalaerobium brockii* alcohol dehydrogenase (TBADH). This example demonstrates that an HKR substrate with a considerably larger R group, hexene oxide, can also be screened by ISES using a different enzyme couple. Specifically, *Lactobacillus kefir* alcohol dehydrogenase (LKADH) shows a high (S)-selectivity for the oxidation of 1,2-hexenediol and HLADH shows a modest (S)-selectivity.

This example demonstrates greater breadth of the technique, in terms of substrate structure. Indeed, taken together, the propylene oxide and hexene oxide cases, show that a catalyst may be screened in a "cassette fashion" across more than one substrate, at once, in parallel, to give information about substrate selectivity, as well as, enantioselectivity.

This example also shows that good ee predictions can be made when using two reporting enzymes with the same enantiomeric preference, but with a significantly different magnitude of enantioselectivity.

In the experiment, each Co(III)-salen catalyst was mixed with (±)-hexene oxide and dichloromethane and placed in a lower organic layer in each of two parallel cuvettes. Aqueous reporting layers, containing LKADH/NADP+ (cuvette 1) HLADH/NAD+ (cuvette 2), were then added (Scheme 1). The hexenediol product diffuses from the (lower) organic layer into the (upper) aqueous layer, where the HLADH and LKADH enzymes act as sensors, oxidizing the product, and producing the NAD(P)H signal. The increase of absorbance at 340 nm is monitored in parallel by a UV-vis spectrophotometer. Alternatively, the NAD(P)H fluorescence may be monitored (emission wavelength is typically set at a fixed value in the 460-470 nm), either in a cuvette or in a plate format.

chloride and 2M 2-propanol in $H_2O$. Enzyme units were calculated by measuring the rate of formation of NADH at 340 nm for both dehydrogenases (vide infra). In each case, one S.I. unit is taken as the amount of enzyme catalyzing the formation of one µmol of NAD(P)H per minute.

Standardization of HLADH: The assay cuvette contained the following components: 7.2 mM (33 µL) of β-$NAD^+$, 2 µL

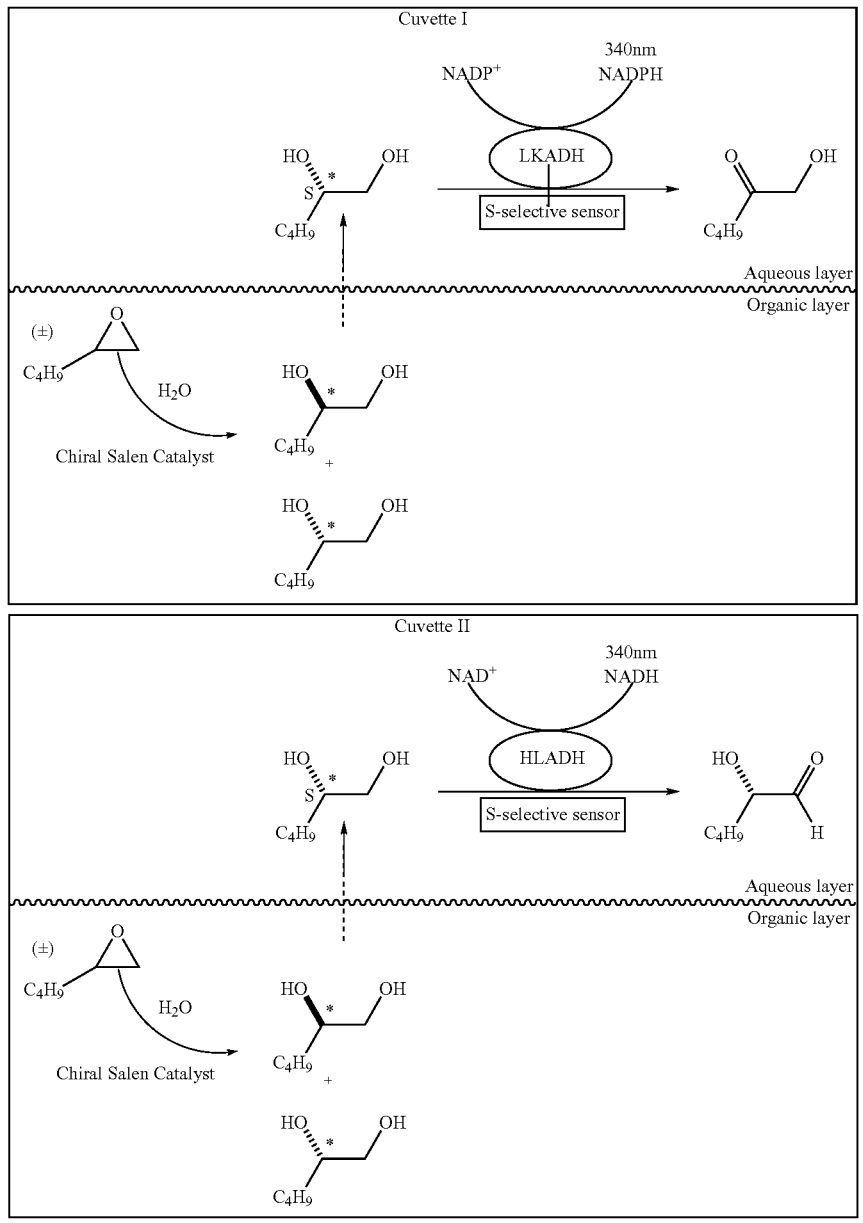

Scheme 1: Double Cuvette-ISES of the HKR of Hexene Oxide

Standardization of Reporting Enzymes

The following stock solutions were made for enzyme standardization: 220 mM β-$NAD^+$, 220 mM β⁻-$NADP^+$, alcohol dehydrogenases from horse liver (HLADH) (0.01-0.02 U/µL) and *Lactobacillus kefir* (LKADH) (0.05-0.07 U/µL) in 25 mM sodium phosphate buffer, pH 7.0, 150 mM magnesium (or 20 µL of a 1:10 dilution) of HLADH stock solution, 865 µL of 50 mM sodium pyrophosphate buffer, pH 8.8, and 200 mM (100 µL) of 2-propanol. The reaction was initiated by the addition of 2-propanol, which typically gave a rate of 0.12±0.01 abs/min at 25° C., 340 nm. This was indicative of 0.010 U of HLADH per µL of the stock solution.

Standardization of LKADH: The assay cuvette contained the following components: 2.2 mM (10 μL) β-NADP$^+$, 1.5 mM (10 μL)MgCl$_2$, 2 μL (or 20 μL of 1:10 dilution) of LKADH stock solution, 878 μL of 50 mM sodium pyrophosphate buffer, pH 8.8, and 200 mM (100 μL) of 2-propanol. The reaction was initiated by the addition of 2-propanol, which typically gave a rate of 0.110±0.001 abs/min at 25° C., 340 nm. This was indicative of 0.009 U of LKADH per μL of the stock solution.

Double Cuvette ISES Procedure for HKR of Hexene Oxide

A general procedure for the 'double cuvette ISES' to estimate the enantiomeric excess of the 1,2-hexenediol product from the hydrolytic kinetic resolution (HKR) of racemic hexene oxide is described below. Quartz cuvettes with a 1 cm light path and with a nominal 1 mL volume were used. For every catalyst, a two cuvette screen was performed, with cuvette A containing HLADH, and cuvette B containing LKADH. As indicated above, both enzymes are (S)-selective, but differ in degree of selectivity.

Organic Layer: Both cuvettes A and B had the following composition: 140 μL of (±)-hexene oxide (116 mg, 1.16 mmols) 160 μL of CH$_2$Cl$_2$ (Amylene stabilized, purchased) and 2.0 mol % Co(III)-salen-acetate catalyst. The total organic layer volume was maintained as 300 μL in all catalyst screens.

Aqueous Layer in Cuvette A: 5.0 μL (0.05 U with 2-propanol) of HLADH stock solution, (0.01 U/μL), 16.5 μL (7.2 mM) of β-NAD$^+$ stock and 478.5 μL of 50 mM sodium pyrophosphate buffer, pH 8.8.

Aqueous Layer in Cuvette B: 16.7 μL (0.15 U with 2-propanol) of LKADH stock (0.009 U/μL), 5 μL (2.2 mM) of β-NADP$^+$ stock, 5 μL (1.5 mM) of MgCl$_2$ and 473.5 μL of 50 mM sodium pyrophosphate buffer, pH 8.8.

The total volume of the aqueous layer was maintained as 500 μL in both cuvettes in all ISES experiments. For each cuvette, 23 micromol of catalyst was dissolved in 160 μL of water saturated CH$_2$Cl$_2$ in a 1.5 ml microcentrifuge tube. This catalyst solution was kept at rt for 20-30 min. After that the catalyst solution was stored in an ice bath along with (±)-hexene oxide separately. Every catalyst screen was done in duplicate (i.e. two runs of cuvette A and two of cuvette B per screen). Then the aqueous layers were prepared first in 1.5 mL microcentrifuge tubes at 25° C. and drawn into 1 mL disposable syringes fitted with 19 gauge stainless steel needles. This was done about 2 min before layering.

Following this, the organic layers were prepared in 1.5 mL microcentrifuge tubes by briefly mixing the catalyst solution with 140 μL (1.16 mmols) of (±)-hexene oxide in an ice bath. Immediately, they were loaded in 1 ml quartz cuvettes, using 1 mL disposable syringes. The aqueous layer was then added carefully along the walls of the cuvette. A reversed loading method (aqueous layer was loaded first inside the cuvette, then the organic layer was loaded on the bottom by injecting it slowly at the bottom of the cuvette through the aqueous layer.) was adopted for the catalysts derived from 1-hydrdoxy-2-naphthaldehyde to improve solubility. This was followed by the parallel observation of continuous NAD(P)H formation at 340 nm in both reporting cuvettes, using a UV/vis spectrophotometer with six cell positioner at 25° C.

The enantiomeric ratio was predicted using the rate of change of absorption (i.e. ΔAbs/time) from the 0-10 min window for all catalysts. No prediction was attempted for very slow catalysts (i.e., ≦15 mAbs/min in 0-10 min time window for HLADH cuvettes).

Hydrolytic Kinetic Resolution of (±)-Hexene Oxide

Co(III)-salen (acetate) catalysts were evaluated for HKR of (±)-hexene oxide, under neat conditions, similar to those described by Jacobsen and co-workers (Schaus, S. E.; Brandes, B. D.; Larrow, J. F.; Tokunaga, M.; Hansen, K. B.; Gould, A. E.; Furrow, M. E.; Jacobsen, E. N. *J. Am. Chem. Soc.* 2002, 124, 1307-1315). Reactions were stopped after 0.5 h, to obtain the enantiopurity of the 1,2-hexenediol produced at relatively early reaction times, for comparison with biphasic ISES predictions.

A typical procedure follows: To the Co(III)-salen catalyst derived from 1e (16.6 mg, 23.2 μmol, 2.0 mol %) at rt was added (±)-hexene oxide (116 mg, 1.16 mmols). The mixture was cooled to 0° C. Then water (11.4 μL, 0.64 mmols, 0.55 equiv.) was added and the flask was capped tightly and stirred 25° C. for 30 min. The progress of the reaction was estimated by $^1$H NMR, the reaction mixture was cooled to 0° C., an aliquot was then withdrawn and dissolved in CDCl$_3$ at 0° C. bath. After distilling over the unreacted epoxide, the diol product was collected, and then itself distilled again by Kugelrohr. When the reaction conversion was more than 50% in 30 min, 15 min reaction time was used (for catalyst 1e) to get the product diol.

To determine ee, the isolated diol was derivatized using p-bromobenzoyl imidazole (2.2 equiv.) in THF in the presence of NaH (4 equiv.) at rt for 5 min. The bis(p-bromobenzoate) obtained following sequential washes with 1 N HCl and bicarbonate (sat'd aqueous), was of sufficient purity to be used directly for chiral HPLC analysis [Chiralcel OD, (99:1 hexanes/2-PrOH; 1 mL/min)].

Figure 5:
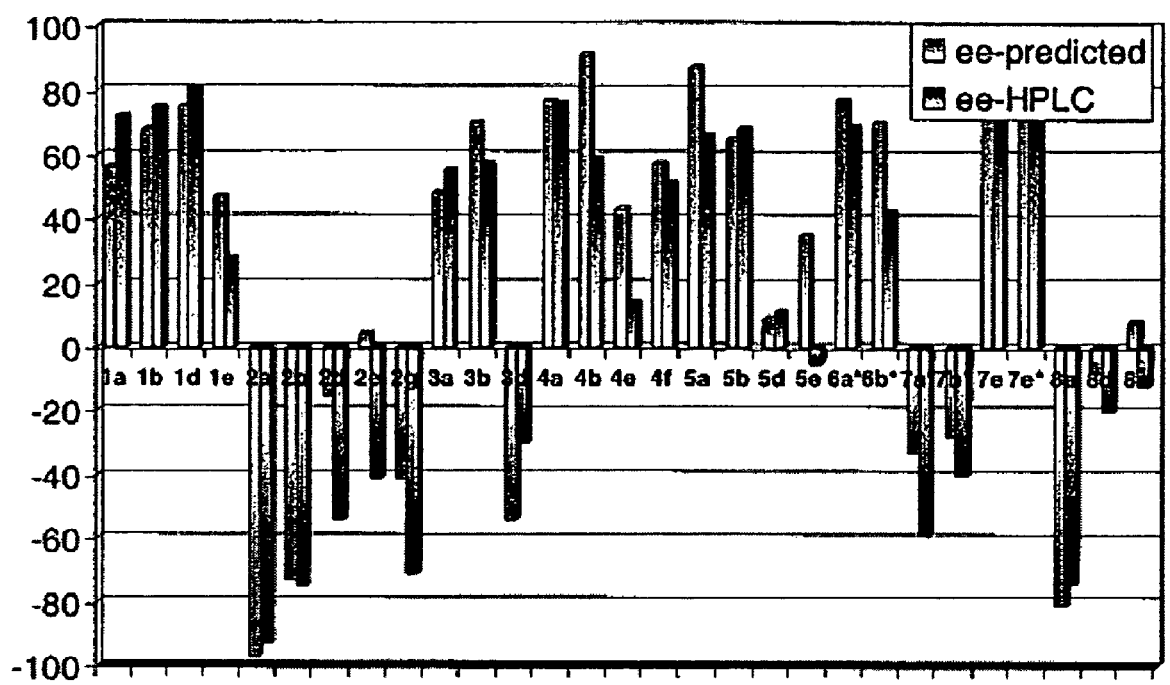
FIG. 5 shows a comparison of predicted and observed ee's for the HKR of ±propylene oxide.
Figure 7:
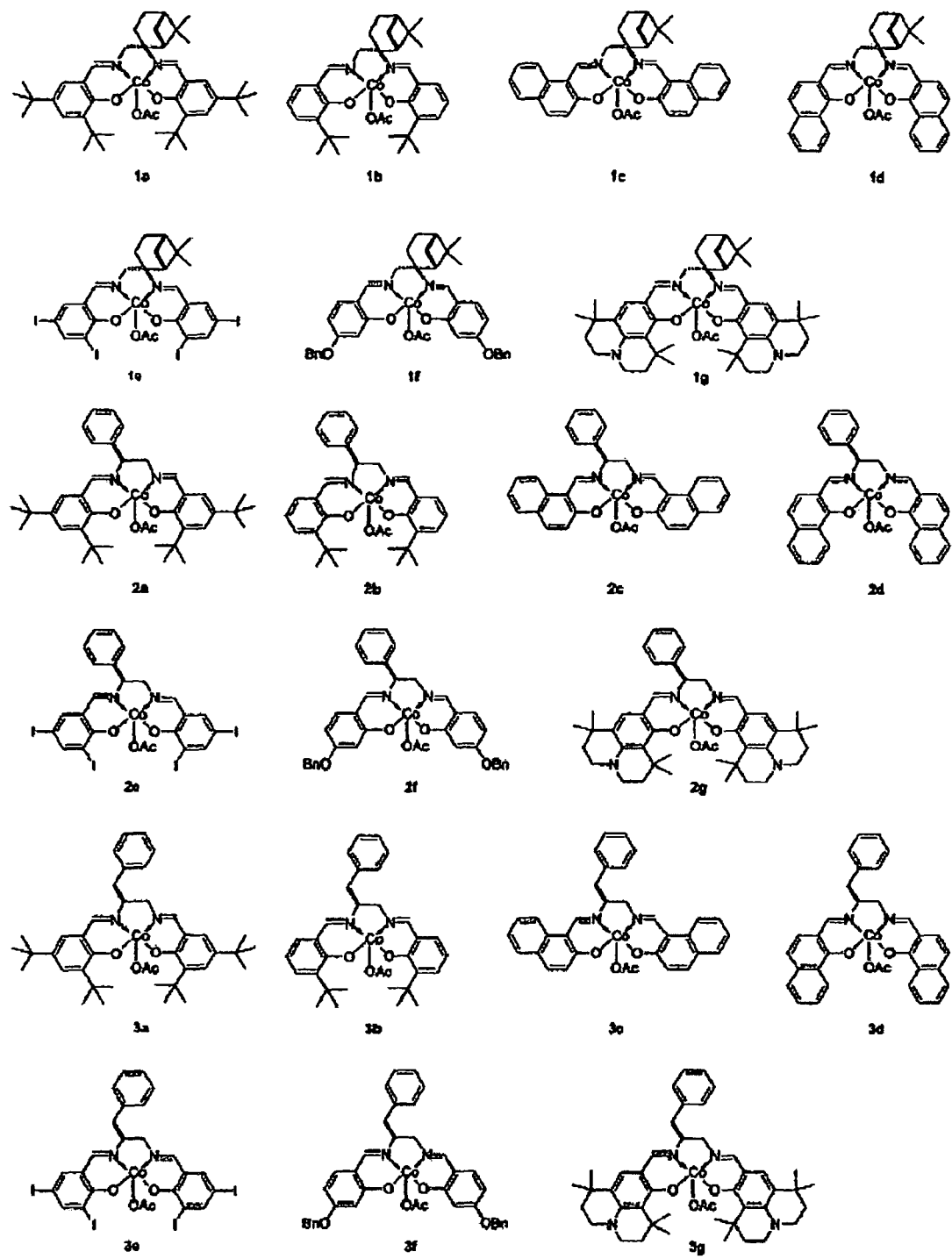
FIGS. 7-7C show representative Co(III)-salen catalysts utilized in the examples below (salens and the Co catalysts prepared therefrom are numbered identically throughout the specification)
Figure 7A:
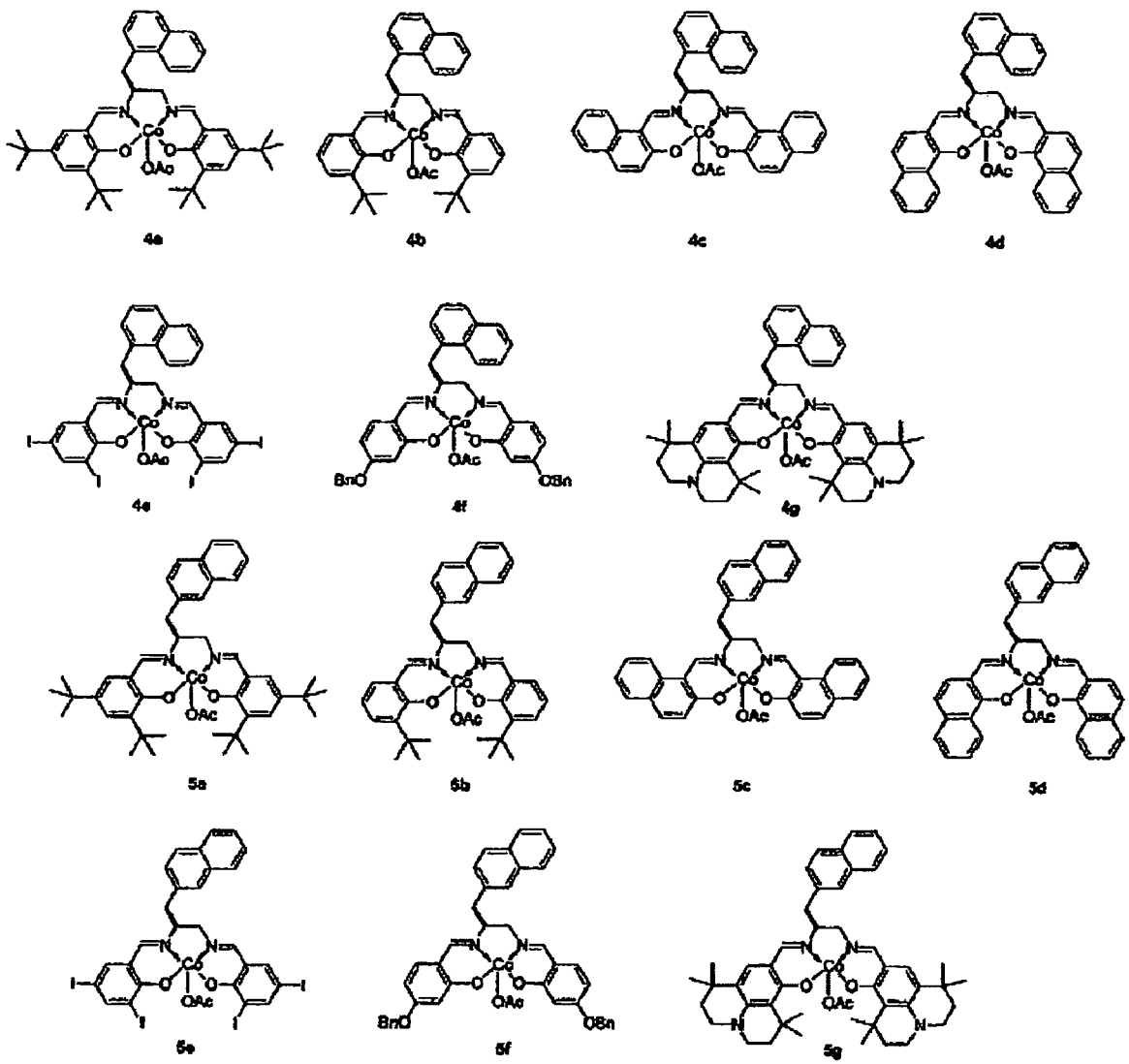
Figure 7B:
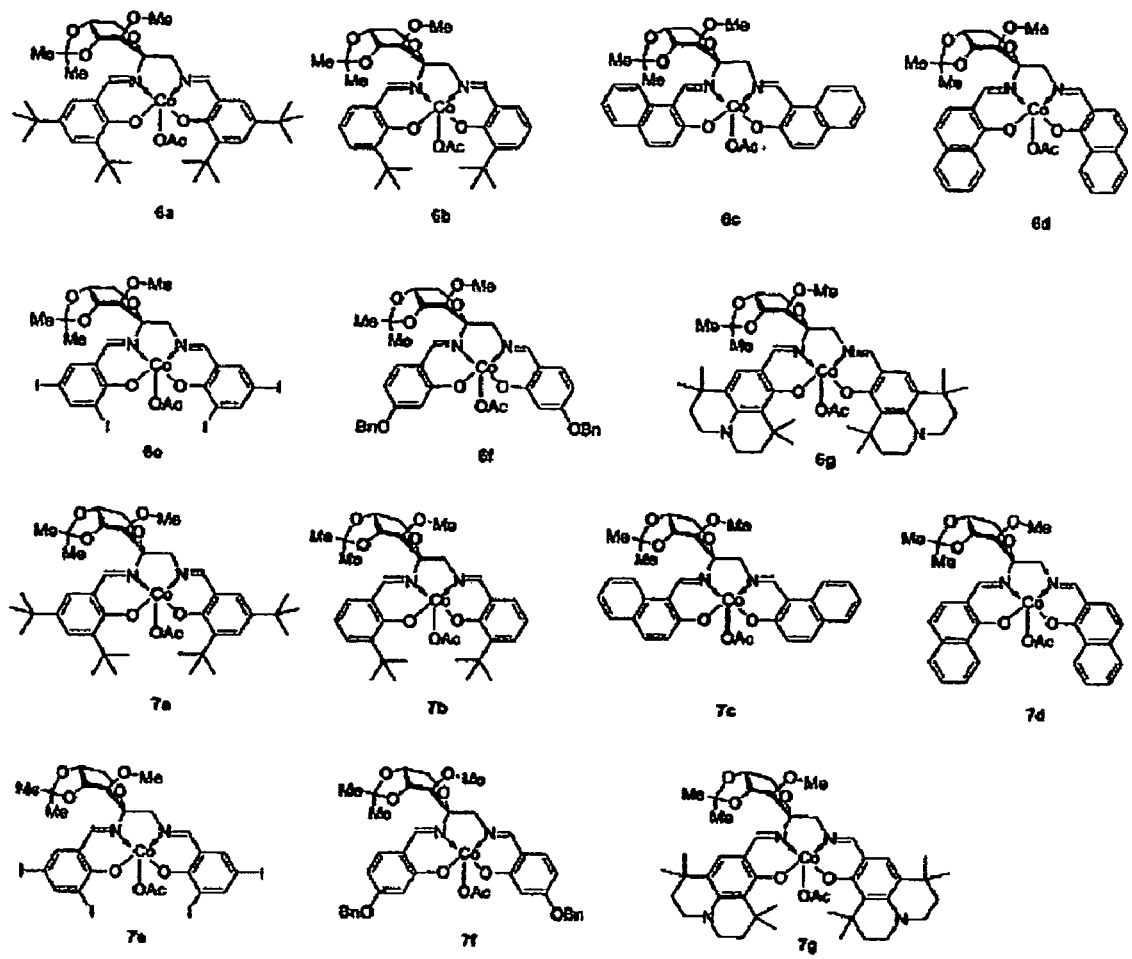
Figure 7C:
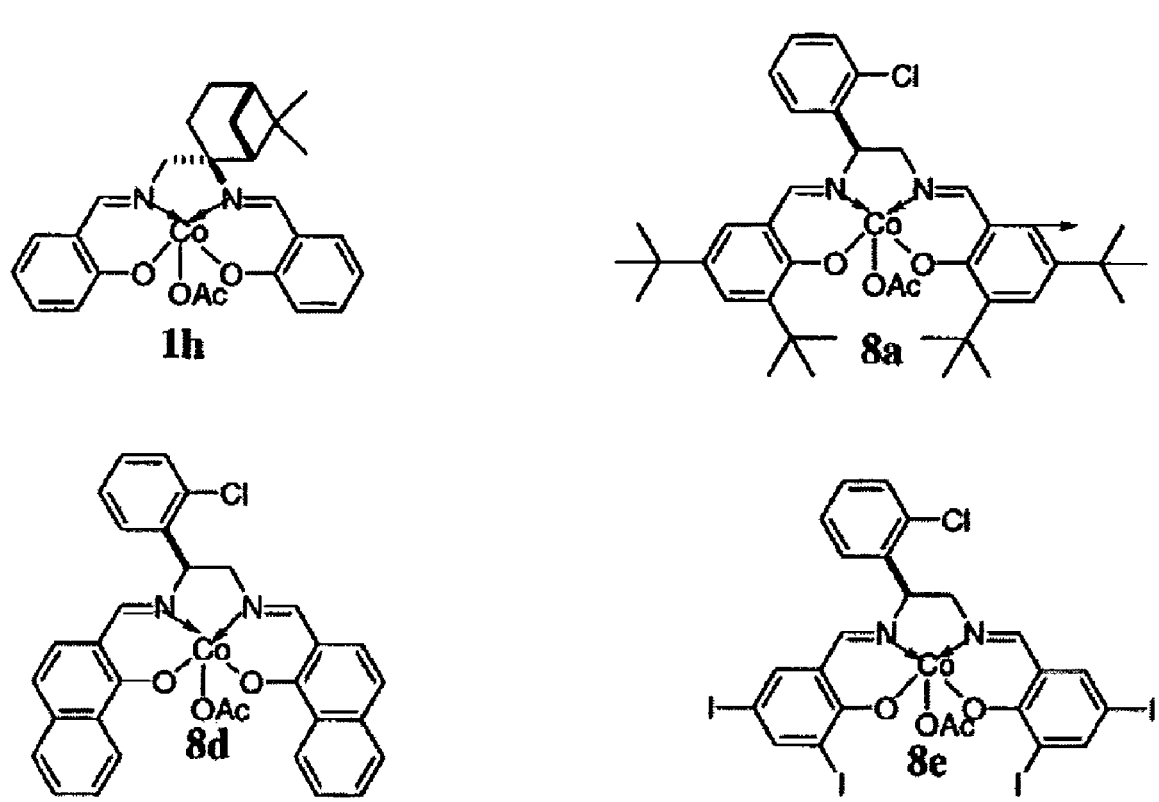

A number of "Co(III)-salen" catalysts (FIGS. 7-7C) were subjected to "cassette screening" for the HKR of both (±)-propylene oxide and (±)-hexene oxide, using UV/vis spectroscopy. A comparison between the predicted and the measured ee's for the HKR of (±)-propylene oxide is presented in FIG. 5. Above a 50% ee threshold, in either direction, ISES found 5 of 5 hits (within a 21% ee margin). For the HKR of (±)-hexene oxide, a comparison between the predicted and the measured ee's is presented in FIG. 6. Above a 50% threshold in either direction, ISES finds 7 of 7 hits within a 24% ee margin. Note that this is particularly good since the biphasic ISES conditions are being used to predict ee's measured under Jacobsen's HKR conditions ("neat" epoxide, containing 0.55 equivalents of water).

While the invention has been described with respect to specific examples including presently preferred modes of carrying out the invention, those skilled in the art will appreciate that there are numerous variations and permutations of the above described systems and techniques that fall within the spirit and scope of the invention as set forth in the appended claims.

We claim:

1. A method for monitoring the stereoselectivity of at least one organic chemical reaction and the relative rate of at least one organic chemical reaction, wherein the reaction produces a product that can exist as at least two stereoisomers, the process comprising:

providing a first reaction zone containing (1) an organic phase comprising the reaction mixture for producing said product and (2) an aqueous phase adjacent to, but substantially immiscible with said organic phase, said aqueous phase containing at least one first sensing agent that preferentially acts on a first stereoisomer in said product to produce a monitorable change, said product being diffusible into said aqueous phase (2);

providing a second reaction zone containing (A) an organic phase also comprising the reaction mixture for producing said product and (B) an aqueous phase adjacent to, but substantially immiscible with said organic phase, said aqueous phase containing at least one second sensing agent that is different from said first sensing agent and
- [i] preferentially acts on the first stereoisomer in the product, but with a different stereoselectivity for the stereoisomers formed in the product than the first sensing agent to produce a monitorable change or
- [ii] acts at equal rates on both formed stereoisomers of the product to produce a monitorable change or
- [iii] preferentially acts on a second stereoisomer in the product to produce a monitorable change, said product being diffusible into said aqueous phase (B), conducting said reactions in said organic phases (1) and (A) to produce said product, allowing said product to diffuse into said aqueous phases (2) and (B) and react with said first and second sensing agents, monitoring the changes caused by said reactions with said first and second sensing agents and correlating said changes to determine the relative rate and stereoselectivity of said organic chemical reaction in said organic phases (1) and (A).

2. The method of claim 1 wherein said first and second sensing agents are enzymes.

3. The method of claim 1 wherein said monitorable changes produced in aqueous phases (2) and (B) are spectroscopic.

4. The method of claim 1 wherein said monitorable changes produced in aqueous phases (2) and (B) are visible to the human eye, and are recorded photographically and quantitated by analyzing image pixel density.

5. The method of claim 1 wherein said monitorable changes produced in aqueous phases (2) and (B) are determined by measurement of absorbance in the UV or visible region of the spectrum.

6. The method of claim 1 wherein said monitorable changes produced in aqueous phases (2) and (B) are determined by measurement of fluorescence.

7. The method of claim 1 wherein said monitorable changes produced in aqueous phases (2) and (B) are visible to the human eye and are measured visibly or photographically in a microtitre plate format.

8. The method of claim 1 wherein said monitorable changes produced in aqueous phases (2) and (B) are visible to the human eye and are measured visibly or photographically in a reaction vessel or a multimicrocell.

9. The method of claim 1 wherein said monitorable changes produced in aqueous phases (2) and (B) are measured by UV/visible spectroscopy in cuvettes or a multimicrocell, using a spectrophotometer equipped with an automated cell positioner or with multimicrocell-reading capability.

10. The method of claim 1 wherein said monitorable changes produced in aqueous phases (2) and (B) are measured by UV/visible spectroscopy in a microtitre plate format.

11. The method of claim 1 wherein said monitorable changes produced in aqueous phases (2) and (B) are determined by measurement of fluorescence in the visible region using the human eye or photography.

12. The method of claim 1 wherein said monitorable changes produced in aqueous phases (2) and (B) are determined by measurement of fluorescence in the UV or visible region using a fluorescence spectrophotometer.

13. The method of claim 1 wherein said monitorable changes produced in aqueous phases (2) and (B) are determined by measurement of fluorescence in the UV or visible region using a plate-reading fluorescence spectrophotometer.

14. The method of claim 1 wherein said reaction mixture contains at least one catalyst for said reaction.

15. The method of claim 14 wherein said at least one catalyst is a Co(III)-salen complex.

16. The method of claim 15 wherein said Co(III)-salen complex is selected from the group consisting of:

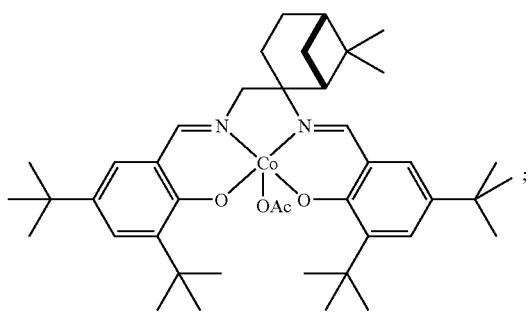

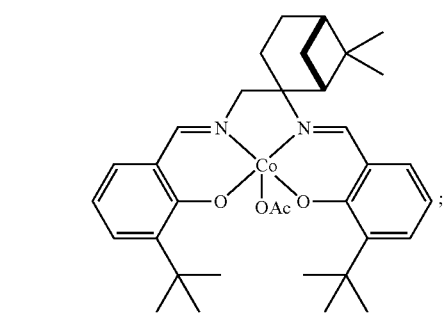

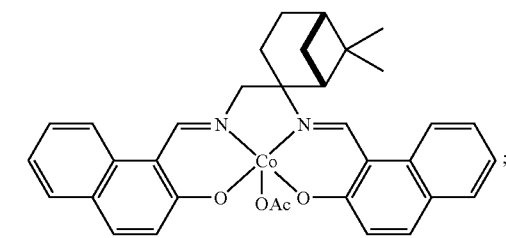

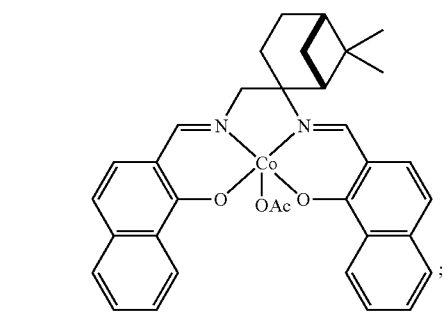

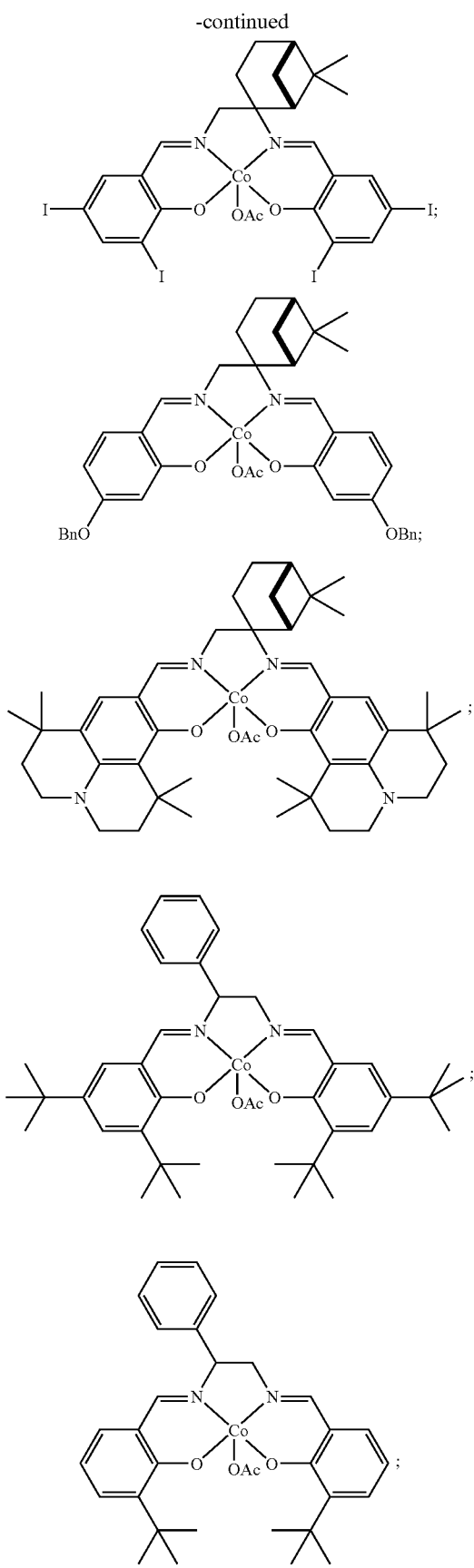
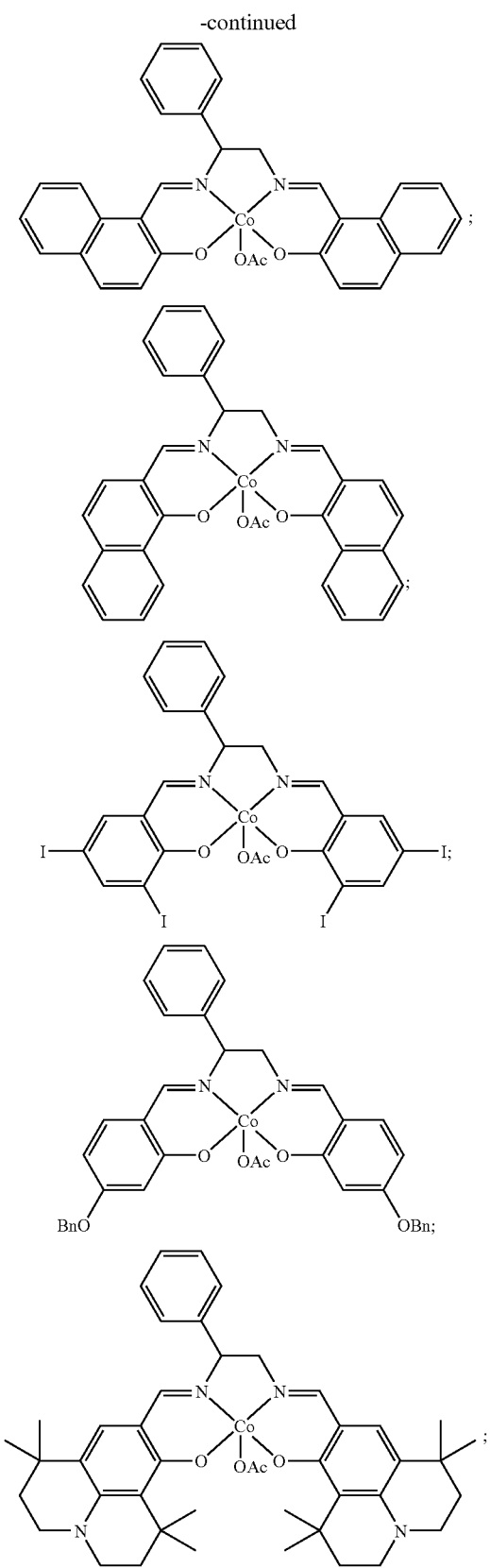

-continued
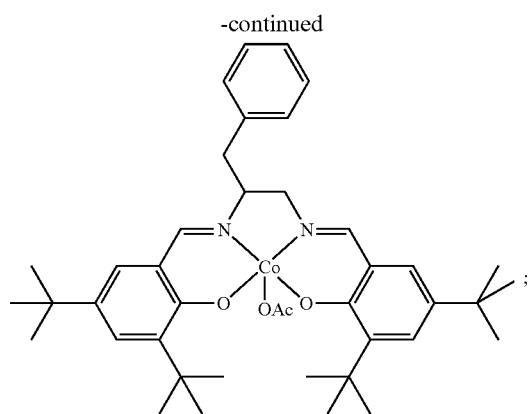
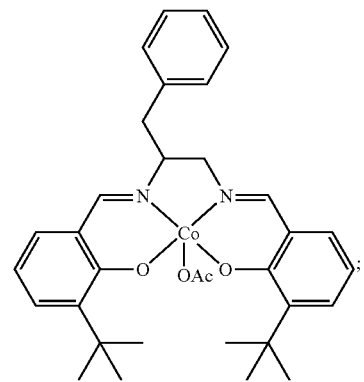
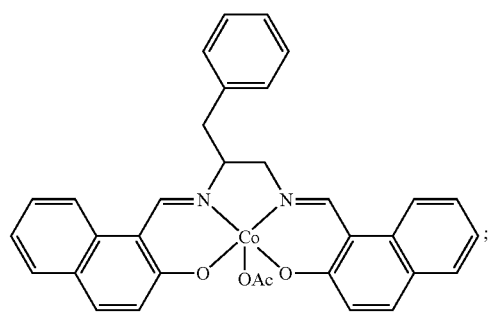
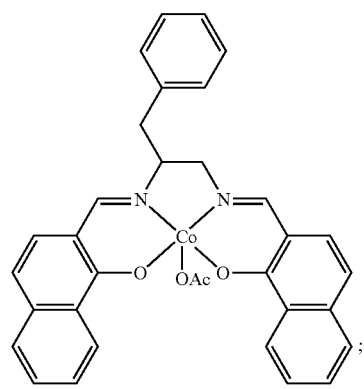
-continued
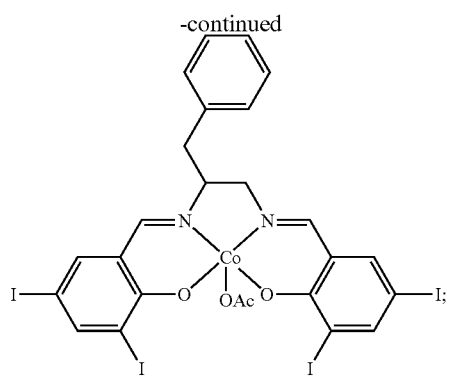
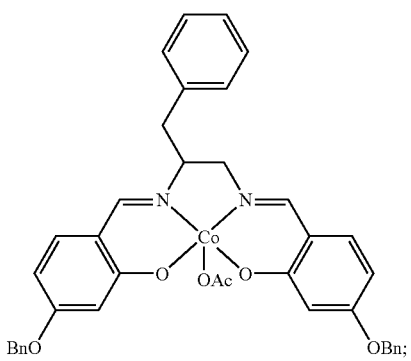
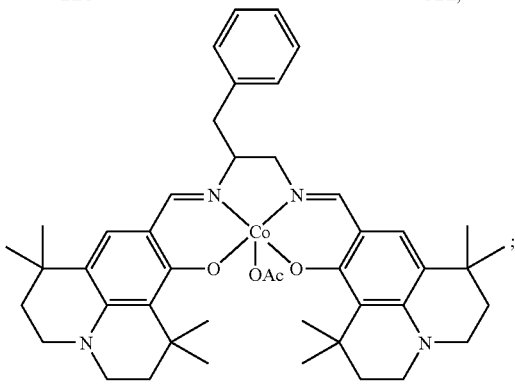
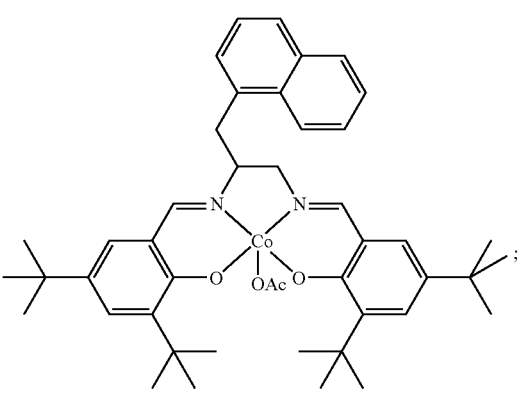

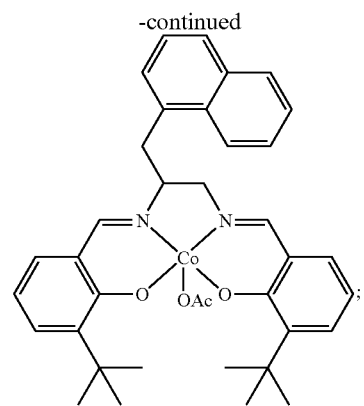
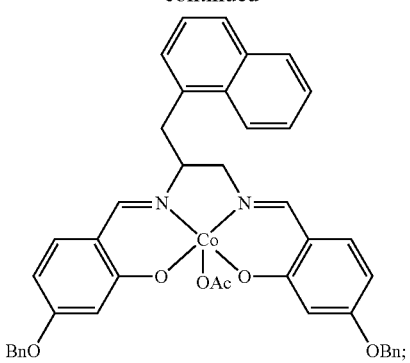
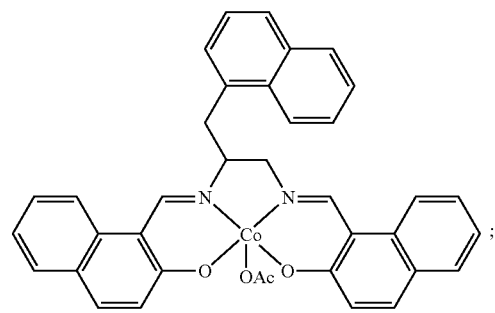
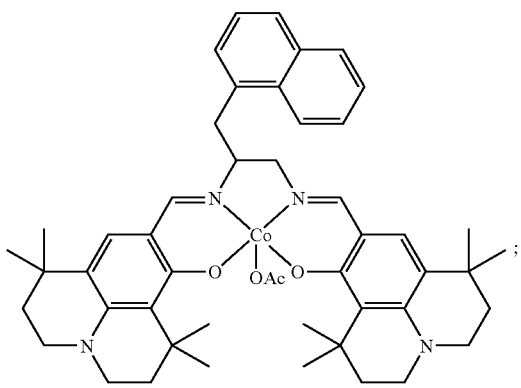
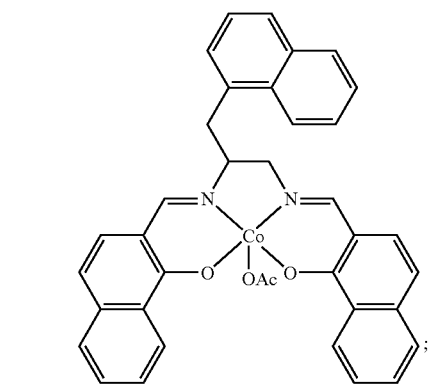
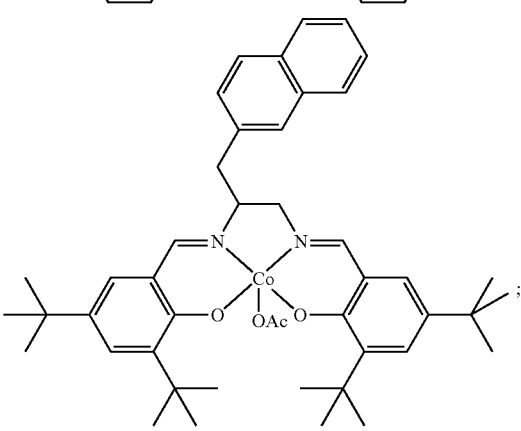
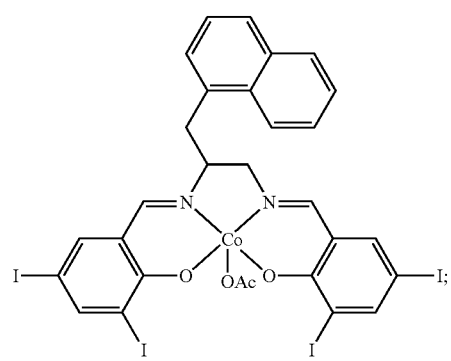
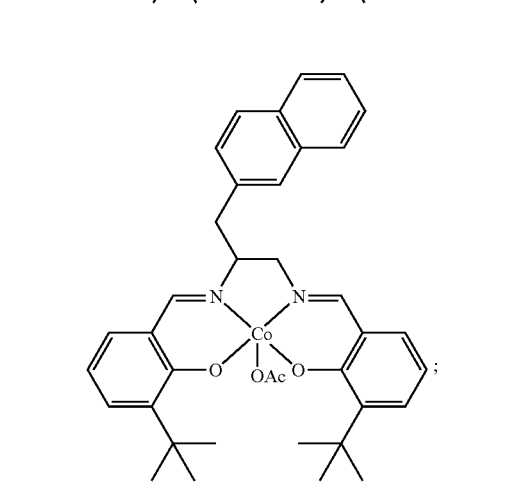

-continued
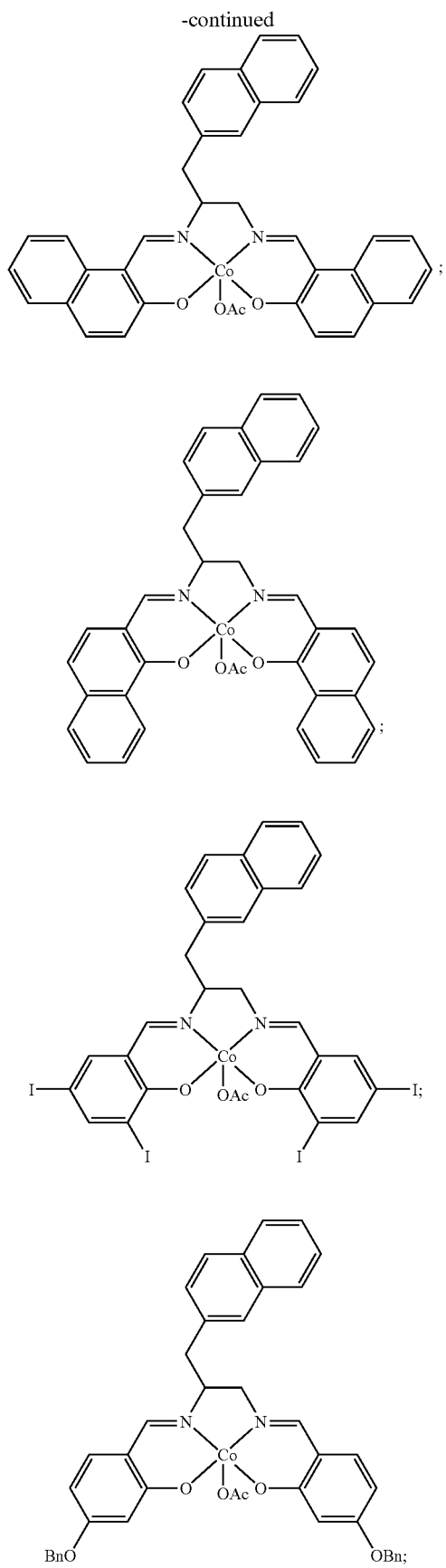
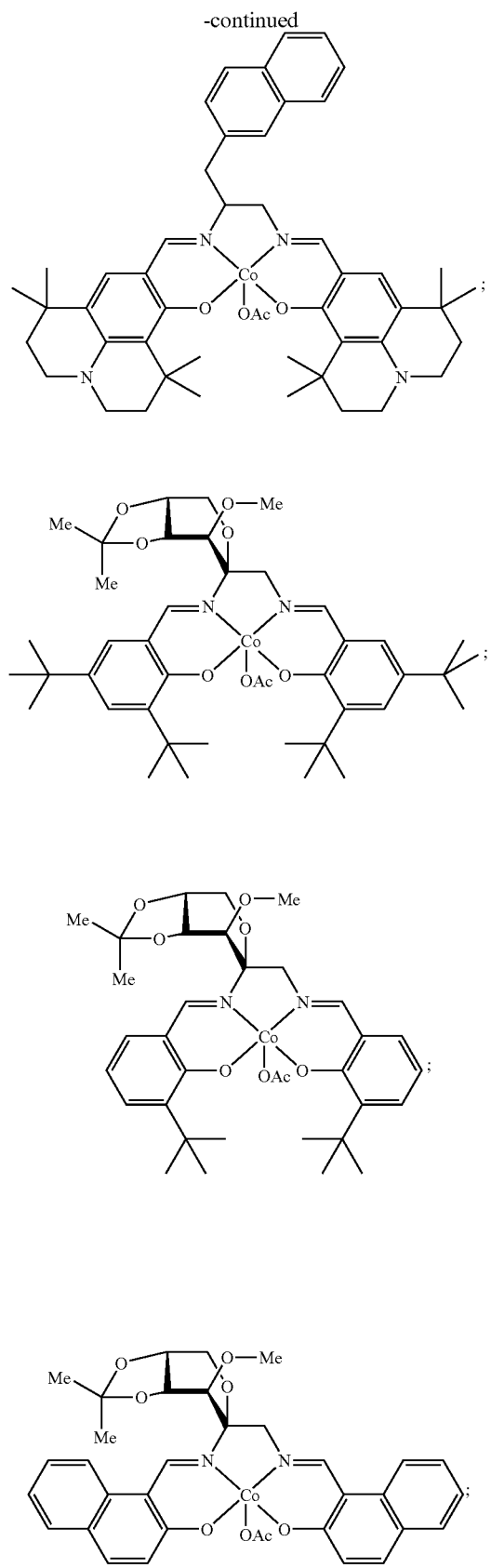

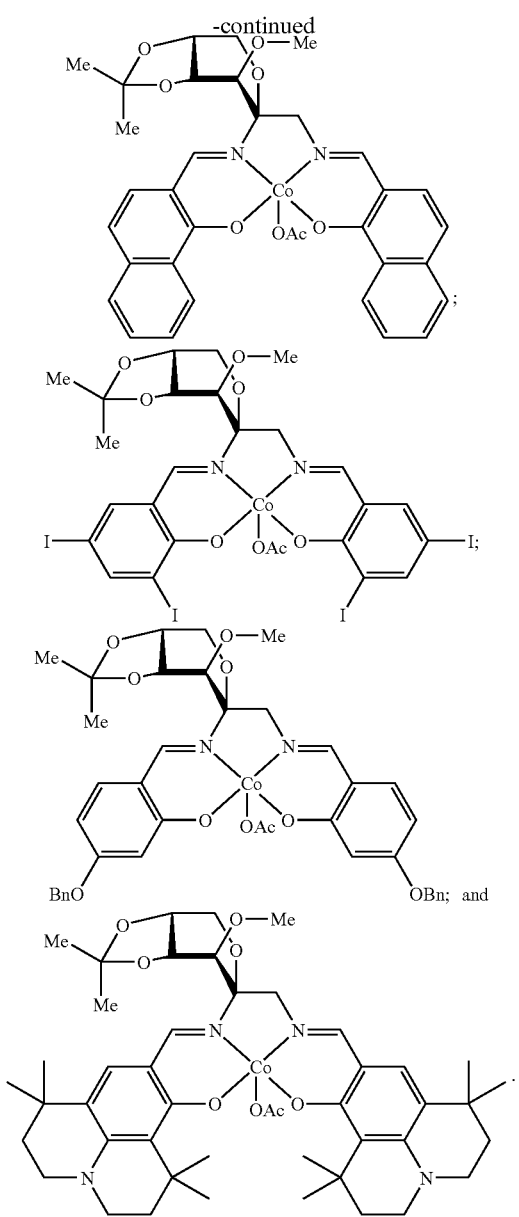

17. The method of claim 1 wherein said product is an alcohol and said sensing agents in aqueous phases (2) and (B) are alcohol dehydrogenase or oxidase enzymes that oxidize said product.

18. The method of claim 17 wherein said alcohol product is a diol.

19. The method of claim 18 wherein said diol is a 1,2-diol.

20. The method of claim 19 wherein said diol is propane-1,2-diol or hexene-1,2-diol.

21. The method of claim 17 wherein the sensing agents are Horse Liver Alcohol Dehydrogenase (HLADH) and *Thermoanaerobium brocki* Dehydrogenase (TBADH).

22. The method of claim 17 wherein the sensing agents are Horse Liver Alcohol Dehydrogenase (HLADH) and *Lactobacillus kefir* Dehydrogenase (LKADH).

23. The method of claim 17 wherein said alcohol is a halohydrin, a β-azido alcohol, a β-cyanalcohol, a β-alkoxy alcohol, a β-aryloxy alcohol, a β-thioalkyl alcohol, or a β-amino alcohol.

24. The method of claim 17 wherein said alcohol is the product of an aldol-type condensation, wherein a carbon acid having a proton alpha to one or more electron-withdrawing groups is condensed with an aldehyde and is deprotonated in the course of the condensation.

25. The method of claim 17 wherein said alcohol is the product of a Morita-Baylis-Hillman reaction.

26. The method of claim 17 wherein said alcohol is the product of a carbonyl reduction reaction.

27. The method of claim 17 wherein said alcohol is a cyanohydrin.

28. The method of claim 1 wherein said product is an amine and said sensing agents in aqueous phases (2) and (B) are amine dehydrogenase or amine oxidase enzymes that oxidize said product.

29. The method of claim 1 wherein said product is an aldehyde or hemiacetal and said sensing agents in aqueous phases (2) and (B) are aldehyde or alcohol dehydrogenase enzymes that oxidize said product.

* * * * *

UNITED STATES PATENT AND TRADEMARK OFFICE
CERTIFICATE OF CORRECTION

| | |
|---|---|
| PATENT NO. | : 7,767,388 B2 |
| APPLICATION NO. | : 11/434247 |
| DATED | : August 3, 2010 |
| INVENTOR(S) | : David B. Berkowitz |

It is certified that error appears in the above-identified patent and that said Letters Patent is hereby corrected as shown below:

Column 62, line 14 (Claim 21), please delete "brocki" and insert --brockii-- therefor;

Column 62, line 20 (Claim 23), please delete "β-cyanalcohol" and insert --β-cyanoalcohol-- therefor.

Signed and Sealed this
Eighth Day of March, 2011

David J. Kappos
*Director of the United States Patent and Trademark Office*